US010927083B2

(12) United States Patent
Derbyshire et al.

(10) Patent No.: US 10,927,083 B2
(45) Date of Patent: *Feb. 23, 2021

(54) SUBSTITUTED BENZIMIDAZOLES AS INHIBITORS OF TRANSFORMING GROWTH FACTOR-β KINASE

(71) Applicant: Duke University, Durham, NC (US)

(72) Inventors: Emily Derbyshire, Durham, NC (US); Timothy A. J. Haystead, Chapel Hill, NC (US); Philip F. Hughes, Chapel Hill, NC (US)

(73) Assignee: Duke University, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/273,786

(22) Filed: Feb. 12, 2019

(65) Prior Publication Data

US 2019/0263759 A1    Aug. 29, 2019

Related U.S. Application Data

(63) Continuation-in-part of application No. 15/720,731, filed on Sep. 29, 2017, now Pat. No. 10,207,998.

(60) Provisional application No. 62/649,923, filed on Mar. 29, 2018, provisional application No. 62/401,733, filed on Sep. 29, 2016.

(51) Int. Cl.
| | |
|---|---|
| C07D 235/30 | (2006.01) |
| A61P 33/06 | (2006.01) |
| A61P 1/00 | (2006.01) |
| C07D 403/14 | (2006.01) |
| A61P 29/00 | (2006.01) |
| C07D 401/14 | (2006.01) |
| A61P 35/00 | (2006.01) |

(52) U.S. Cl.
CPC .............. *C07D 235/30* (2013.01); *A61P 1/00* (2018.01); *A61P 29/00* (2018.01); *A61P 33/06* (2018.01); *A61P 35/00* (2018.01); *C07D 401/14* (2013.01); *C07D 403/14* (2013.01)

(58) Field of Classification Search
CPC .................................................. C07D 235/30
USPC ..................................................... 548/307.7
See application file for complete search history.

(56) References Cited

U.S. PATENT DOCUMENTS

| 5,260,291 A | 11/1993 | Lunt et al. |
| 5,747,498 A | 5/1998 | Schnur et al. |
| 7,132,438 B2 | 11/2006 | Frenkel et al. |
| 2008/0139587 A1 | 6/2008 | Huang et al. |

FOREIGN PATENT DOCUMENTS

| EP | 0520722 A1 | 12/1992 |
| EP | 0564409 A1 | 10/1993 |
| EP | 0566226 A1 | 10/1993 |
| EP | 0787722 A1 | 8/1997 |
| EP | 0837063 A1 | 4/1998 |
| WO | WO 96/33980 A1 | 10/1996 |
| WO | WO 97/02266 A1 | 1/1997 |
| WO | WO 97/30034 A1 | 8/1997 |
| WO | WO 97/38983 A1 | 10/1997 |
| WO | WO 97/49688 A1 | 12/1997 |
| WO | WO 98/10767 A1 | 3/1998 |
| WO | WO 99/03854 A1 | 1/1999 |
| WO | WO 02/22577 A1 | 3/2002 |
| WO | WO 03/013541 A1 | 2/2003 |

OTHER PUBLICATIONS

"McCutcheon's vol. 1, Emulsifiers & Detergents," North American ed., 1994, pp. 236-239.
"Remington's Pharmaceutical Sciences," 15th ed., 1975, Meade Publishing Co., Easton, Pa., pp. 335-337.
"Periodic Table of the Elements," CRC Handbook of Chemistry and Physics, 75th Edition, 1994.
Adams et al., "PHENIX: a comprehensive Python-based system for macromolecular structure solution," Acta Crystallogr D Biol Crystallogr., 2010, 66(Pt 2):213-221.
Ahmed et al., "The E3 ligase Itch and deubiquitinase Cyld cooperative regulate Tak1 and inflammation," Nat Immunol, 2011, 12(12):1176-1183.
Alam et al., "Phosphoproteomics reveals malaria parasite Protein Kinase G as a signalling hub regulating egress and invasion," Nature Communications, 2015, 6:7285, 15 pages.
Alexander et al., "bcl::Cluster: A method for clustering biological molecules coupled with visualization in the Pymol Molecular Graphics System," IEEE Int Conf Comput Adv Bio Med Sci, 2011, 13-18.

(Continued)

*Primary Examiner* — Douglas M Willis
(74) *Attorney, Agent, or Firm* — Michael Best & Friedrich LLP

(57) ABSTRACT

The present invention provides inhibitors of TAK1 having formula (II), affinity resins, and fluorescent dyes and methods of using such compounds to treat various diseases or in protein isolation or purification.

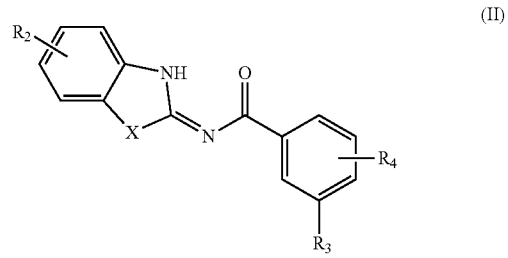

13 Claims, 17 Drawing Sheets

Specification includes a Sequence Listing.

(56) References Cited

OTHER PUBLICATIONS

Alwarawrah et al., "Fasnall, a Selective FASN Inhibitor, Shows Potent Anti-tumor Activity in the MMTV-Neu Model of HER2+ Breast Cancer," Cell Chem Biol, 2016, 23(6):678-688.
Aminake et al., "The proteasome of malaria parasites: A multi-stage drug target for chemotherapeutic intervention?" International Journal for Parasitology, Drugs and Drug Resistance, 2012, 2:1-10.
Anamika et al., "A genomic perspective of protein kinases in Plasmodium falciparum," Proteins, 2005, 58(1):180-189.
Angel et al., "The role of Jun, Fos and the AP-1 complex in cellproliferation and transformation," Biochim Biophys Acta, 1991, 1072(2-3):129-157.
Ansel, "Introduction to Pharmaceutical Dosage Forms", 2nd ed., 1976, Lea & Febiger, Philadelphia.
Bain et al., "The selectivity of protein kinase inhibitors: a further update," The Biochemical Journal, 2007, 408(3):297-315.
Balkwill et al., "Tumor necrosis factor or tumor promoting factor?" Cytokine Growth Factor Rev, 2002, 13(2):135-41.
Bang et al., "GSK-3alpha promotes oncogenic KRAS function in pancreatic cancer via TAK1-TAB stabilization and regulation of non-canonical NF-kappaB," Cancer Discov, 2013, 3(6):690-703.
Banker et al., "Modern Pharmaceutics," 1979, Marcel Dekker, Inc., New York, pp. 329-427.
Bantscheff et al., "Quantitative chemical proteomics reveals mechanisms of action of clinical ABL kinase inhibitors," Nat Biotechnol, 2007, 25(9):1035-1044.
Barrott et al., "Tethered Hsp90 inhibitors carrying optical or radioiodinated probes reveal selective internalization of ectopic Hsp90 in malignant breast tumor cells," Chemistry & Biology, 2013, 20(9):1187-1197.
Becker et al., "TGF-beta suppresses tumor progression in colon cancer by inhibition of IL-6 trans-signaling," Immunity, 2004, 21(4):491-501.
Beis et al., "The contents of adenine nucleotides, phosphagens and some glycolytic intermediates in resting muscles from vertebrates and invertebrates," Biochem J, 1975, 152(1):23-32.
Berge et al., "Pharmaceutical Salts," J. Pharm. Sci., 1977, 66(1):1-19.
Bertrand et al., "cIAP1 and cIAP2 facilitate cancer cell survival by functioning as E3 ligases that promote RIP1 ubiquitination," Molecular Cell, 2008, 30(6):689-700.
Bettermann et al., "TAK1 suppresses a 167 NEMO-dependent but NF-kappaB-independent pathway to liver cancer," Cancer Cell, 2010, 17(5):481-496.
Bhoj et al., "Ubiquitylation in innate and adaptive immunity," Nature, 2009, 458(7237):430-437.
Bira et al., "Transforming growth factor beta stimulates rheumatoid synovial fibroblasts via the type II receptor," Mod Rheumatol, 2005, 15(2):108-113.
Bonafede et al., "Cost of tumor necrosis factor blockers per patient with rheumatoid arthritis in a multistate Medicaid population," ClinicoEconomics and Outcomes Research, 2014, 6:381-388.
Bondeson et al., "Catalytic in vivo protein knockdown by small-molecule PROTACs," Nat Chem Biol, 2015, 11(8):611-617.
Bosman et al., "The TAK1-NF-kappaB axis as therapeutic target for AML," Blood, 2014, 124(20):3130-3140.
Bradford, "A rapid and sensitive method for the quantitation of microgram quantities of protein utilizing the principle of protein-dye binding," Anal Biochem, 1976, 72:248-254.
Bradley et al., "TNF-mediated inflammatory disease," J Pathol, 2008, 214(2):149-60.
Broglie et al., "Transforming Growth Factor beta-activated Kinase 1 (TAK1) Kinase Adaptor, TAK1-binding Protein 2, Plays Dual Roles in TAK1 Signaling by Recruiting Both an Activator and an Inhibitor of TAK1 Kinase in Tumor Necrosis Factor Signaling Pathway," Journal of Biological Chemistry, 2010, 285(4):2333-2339.

Brown et al., "Structural basis for the interaction of TAK1 kinase with its activating protein TAB1," J Mol Biol, 2005, 354(5):1013-1020.
Buglio et al., "Essential role of TAK1 in regulating mantle cell lymphoma survival," Blood, 2012, 120(2):347-355.
Bulinski et al., "Overexpression of MAP4 inhibits organelle motility and trafficking in vivo," J. Cell Sci., 1997, 110:3055-3064.
Cai et al., "Elevated TAK1 augments tumor growth and metastatic capacities of ovarian cancer cells through activation of NF-κB signaling," Oncotarget, 2014, 5(17):7549-7562.
Cailleau et al., "Breast tumor cell lines from pleural effusions," J Natl Cancer Inst, 1974, 53(3):661-674.
Carlson et al., "Fluorescence linked enzyme chemoproteomic strategy for discovery of a potent and selective DAPK1 and ZIPK inhibitor," ACS Chem Biol, 2013, 8(12):2715-2723.
Carruthers, "Some Modern Methods of Organic Synthesis," 3rd ed., 1987, Cambridge University Press, Cambridge.
Carter et al., "Purification, cloning, expression and biological characterization of an interleukin-1 receptor antagonist protein," Nature, 1990, 344(6267):633-638.
CAS Registry No. 1111556-37-6 (2009).
Catz et al., "Transcriptional regulation of bcl-2 by nuclear factor kappaB and its significance in prostate cancer," Oncogene, 2001, 20, 7342-51.
Cerami et al., "The cBio cancer genomics portal: an open platform for exploring multidimensional cancer genomics data," Cancer Discov, 2012, 2(5):401-404.
Chan et al., "A domain in TNF receptors that mediates ligand-independent receptor assembly and signaling," Science, 2000, 288(5475):2351-2354.
Choo et al., "TAK1-mediated stress signaling pathways are essential for TNF-alpha-promoted pulmonary metastasis of murine colon cancer cells," Int J Cancer, 2006, 118(11):2758-2764.
Church et al., "Rilonacept in cryopyrin-associated periodic syndromes: the beginning of longer-acting interleukin-1 antagonism," Nat Clin Pract Rheumatol, 2009, 5(1):14-15.
Coussens et al., "Inflammation and cancer," Nature, 2002, 420(6917):860-867.
Davis et al., "Associations of toll-like receptor (TLR)-4 single nucleotide polymorphisms and rheumatoid arthritis disease progression: an observational cohort study," Int Immunopharmacol, 2015, 24(2):346-352.
Denton et al., "Recombinant human anti-transforming growth factor beta1 antibody therapy in systemic sclerosis," Arthritis Rheum, 2007, 56(1):323-333.
Derbyshire et al., "Chemical interrogation of the malaria kinome," Chembiochem, 2014, 15(13):1920-1930.
Derbyshire et al., "Liver-stage Malaria parasites vulnerable to diverse chemical scaffolds," Proc Natl Acad Sci USA, 2012, 109(22):8511-8516.
Deroose et al., "Treatment modifications in tumour necrosis factor-alpha (TNF) based isolated limb perfusion in patients with advanced extremity soft tissue sarcomas," Eur J Cancer, 2015, 51(3):367-373.
Devry et al., "RDP58, a novel immunomodulatory peptide, ameliorates clinical signs of disease in the Lewis rat model of acute experimental autoimmune encephalomyelitis," J Neuroimmunol, 2004, 152(1-2):33-43.
Dodson et al., "A kinetic test characterizes kinase intramolecular and intermolecular autophosphorylation mechanisms," Sci Signal, 2013, 6(282):ra54.
Doerig et al., "Protein kinases of malaria parasites: an update," Trends in Parasitology, 2008, 24(12)570-577.
Dondelinger et al., "RIPK3 contributes to TNFR1-mediated RIPK1 kinase-dependent apoptosis in conditions of cIAP1/2 depletion or TAK1 kinase inhibition," Cell Death Differ, 2013, 20(10):1381-1392.
Drutskaya et al., "Experimental Models of Arthritis in Which Pathogenesis Is Dependent on TNF Expression," Biochemistry—Moscow, 2014, 79(12):1349-1357.
Dunne et al. "IRAK1 and IRAK4 promote phosphorylation, ubiquitination, and degradation of MyD88 adaptor-like (Mal)," The Journal of Biological Chemistry, 2010, 285(24):18276-18282.

(56) References Cited

OTHER PUBLICATIONS

Elliott et al., "Repeated therapy with monoclonal antibody to tumour necrosis factor alpha (cA2) in patients with rheumatoid arthritis," Lancet, 1994, 344(8930):1125-1127.
Emsley et al., "Coot: model-building tools for molecular graphics," Acta Crystallogr D Biol Crystallogr, 2004, D60:2126-32.
Esposito et al., "TNF-Alpha as a Therapeutic Target in Inflammatory Diseases, Ischemia-Reperfusion Injury and Trauma," Current Medicinal Chemistry, 2009, 16(24):3152-3167.
Fadden et al., "Application of chemoproteomics to drug discovery: identification of a clinical candidate targeting Hsp90," Chem Biol, 2010, 17(7):686-694.
Fechtner et al., "Transforming growth factor beta activated kinase 1: a potential therapeutic target for rheumatic diseases," Rheumatology, 2016, 56(7):1060-1068.
Fieser et al., "Fieser and Fieser's Reagents for Organic Synthesis," 1994, John Wiley & Sons, New York.
Finckh et al., "Evidence for differential acquired drug resistance to anti-tumour necrosis factor agents in rheumatoid arthritis," Ann Rheum Dis, 2006, 65(6):746-52.
Francini et al., "Identification of Aminoimidazole and Aminothiazole Derivatives as Src Family Kinase Inhibitors," Chemmedchem, 2015, 10(12):2027-2041.
Fuller et al., "Cardiac protein kinases: the cardiomyocyte kinome and differential kinase expression in human failing hearts," Cardiovasc Res, 2015, 108(1):87-98.
Furniss et al., "Vogel's Textbook of Practical Organic Chemistry," 5th ed., 1989, Essex CM20 2JE, England.
Fuyuno et al., "Genetic characteristics of inflammatory bowel disease in a Japanese population," J Gastroenterol, 2016, 51(7):672-681.
Gao et al., "Integrative Analysis of Complex Cancer Genomics and Clinical Profiles Using the cBioPortal," Science Signaling, 2013, 6(269):pl1.
Garuti et al., "Benzimidazole derivatives as kinase inhibitors," Current Medicinal Chemistry, 2014, 21(20):2284-2298.
Genovese, "Inhibition of p38: has the fat lady sung?" Arthritis Rheum, 2009, 60(2):317-320.
Göbel et al., "RNA Cleavage Catalyzed by Amphoteric Bis(acyl)guanidinium Derivatives," Helvetica Chimica Acta, 2014, 97(2): 215-227.
Gooljarsingh et al., "A biochemical rationale for the anticancer effects of Hsp90 inhibitors: slow, tight binding inhibition by geldanamycin and its analogues," Proceedings of the National Academy of Sciences of the United States of America, 2006, 103(20):7625-7630.
Grell et al., "The Transmembrane Form of Tumor-Necrosis-Factor Is the Prime Activating Ligand of the 80 Kda Tumor-Necrosis-Factor Receptor," Cell, 1995, 83(5):793-802.
Gudey et al., "TRAF6 Stimulates the Tumor-Promoting Effects of TGFβ Type I Receptor Through Polyubiquitination and Activation of Presenilin 1," Science Signaling, 2014, 7(307):ra2.
Guo et al., "TAK1 regulates caspase 8 activation and necroptotic signaling via multiple cell death checkpoints," Cell Death Dis, 2016, 7(9):e2381.
Hackam et al., "Translation of Research Evidence From Animals to Humans," JAMA, 2006, 296(14): 1731-1732.
Hamidi et al., "Polyubiquitination of transforming growth factor beta (TGFbeta)-associated kinase 1 mediates nuclear factor-kappaB activation in response to different inflammatory stimuli," J Biol Chem, 2012, 287(1):123-133.
Hanwell et al., "Avogadro: an advanced semantic chemical editor, visualization, and analysis platform," J Cheminform, 2012, 4(1):17.
Hastie et al., "Assay of protein kinases using radiolabeled ATP: a protocol," Nature Protocols, 2006, 1(2):968-971.
Hayashi et al., "Clinical significance of CYLD downregulation in breast cancer," Breast Cancer Res Treat, 2014, 143(3):447-457.
Haystead et al., "The purinome, a complex mix of drug and toxicity targets," Current Topics in Medicinal Chemistry, 2006, 6(11):1117-1127.
Hinz et al., "Constitutive NF-kappaB maintains high expression of a characteristic gene network, including CD40, CD86, and a set of antiapoptotic genes in Hodgkin/Reed-Sternberg cells," Blood, 2001, 97(9):2798-2807.
Hirata et al., "Post-Translational Modifications of the TAK1-TAB Complex," Int J Mol Sci, 2017, 18(1):205.
Hoffman et al., "Efficacy and safety of rilonacept (interleukin-1 Trap) in patients with cryopyrin-associated periodic syndromes," Arthritis Rheum, 2008, 58(8):2443-2452.
Hopkins et al., "The druggable genome," Nat Rev Drug Discov, 2002, 1(9):727-730.
Hornberger et al., "Discovery of 7-aminofuro[2,3-c]pyridine inhibitors of TAK1: optimization of kinase selectivity and pharmacokinetics," Bioorg Med Chem Lett, 2013, 23(16):4511-4516.
Hornef et al., "Intracellular recognition of lipopolysaccharide by toll-like receptor 4 in intestinal epithelial cells," J Exp Med, 2003, 198(8):1225-1235.
Howe et al., "Identification of an allosteric small molecule inhibitor selective for the inducible form of heat shock protein 70," Chem Biol, 2014, 21, 1648-59.
Hsu et al., "TNF-dependent recruitment of the protein kinase RIP to the TNF receptor-1 signaling complex," Immunity, 1996, 4, 387-96.
Hsu et al., "TRADD-TRAF2 and TRADD-FADD interactions define two distinct TNF receptor 1 signal transduction pathways," Cell, 1996, 84, 299-308.
Huang et al., "Targeting of TGF-beta-activated protein kinase 1 inhibits chemokine (C-C motif) receptor 7 expression, tumor growth and metastasis in breast cancer," Oncotarget, 2015, 6, 995-1007.
Hughes et al., "A highly selective Hsp90 affinity chromatography resin with a cleavable linker," Bioorganic and medicinal Chemistry, 2012, 20(10):3298-3305.
Iademarco et al., "Characterization of the promoter for vascular cell adhesion molecule-1 (VCAM-1)," J Biol Chem, 1992, 267, 16323-9.
Inokuchi et al., "Disruption of TAK1 in hepatocytes causes hepatic injury, inflammation, fibrosis, and carcinogenesis," Proc Natl Acad Sci USA, 2010, 107, 844-9.
Johnson et al., "The epidemiology of osteoarthritis," Best Pract & Res Clin Rheumatol, 2014, 28, 5-15.
Jones et al., "Profiling drugs for rheumatoid arthritis that inhibit synovial fibroblast activation," Nature Chemical Biology, 2017, 13, 38-45.
Jordan, "Tamoxifen: A Most Unlikely Pioneering Medicine," Nature Reviews: Drug Discovery, 2, 2003, 205.
Jostins et al., "Host-microbe interactions have shaped the genetic architecture of inflammatory bowel disease," Nature, 2012, 491, 119-124.
Kajino-Sakamoto et al., "TAK 1 signaling maintains intestinal integrity by preventing accumulation of reactive oxygen species in the intestinal epithelium," J Immunol, 2010, 185, 4729-37.
Kamiyama et al., "Epoxyquinol B, a naturally occurring pentaketide dimer, inhibits NF-kappaB signaling by crosslinking TAK1," Biosci Biotechnol Biochem, 2008, 72, 1894-900.
Kemp et al., "Design and use of peptide substrates for protein kinases," Methods Enzymol, 1991, 200, 121-34.
Kilty et al., "TAK1 inhibition in the DFG-out conformation," Chem Biol Drug Des, 2013, 82, 500-5.
Kilty et al., "TAK1 selective inhibition: state of the art and future opportunities," Future Med Chem, 2015, 7, 23-33.
Kim et al., "TGF-beta-activated kinase-1: New insights into the mechanism of TGF-beta signaling and kidney disease," Kidney Res Clin Pract, 2012, 31(2): 94-105.
Kishimoto et al., "TAK1 mitogen-activated protein kinase kinase kinase is activated by autophosphorylation within its activation loop," Journal of Biological Chemistry, 2000, 275, 7359-7364.
Koenders et al., "Novel therapeutic targets in rheumatoid arthritis," Trends Pharmacol Sci, 2015, 36, 189-95.
Komaki et al., "Efficacy, safety and pharmacokinetics of biosimilars of anti-tumor necrosis factor-alpha agents in rheumatic diseases; A systematic review and meta-analysis," J Autoimmun, 2017, 79:4-16.

(56) References Cited

OTHER PUBLICATIONS

Komatsu et al., "Targeted disruption of the Tab1 gene causes embryonic lethality and defects in cardiovascular and lung morphogenesis," Mech Dev, 2002, 119, 239-49.
Kreuz et al., "NF-kappaB inducers upregulate cFLIP, a cycloheximide-sensitive inhibitor of death receptor signaling," Mol Cell Biol, 2001, 21, 3964-73.
Kristensen et al., "Localization of tumour necrosis factor-alpha (TNF-alpha) and its receptors in normal and psoriatic skin: epidermal cells express the 55-kD but not the 75-kD TNF receptor," Clinical and Experimental Immunology, 1993, 94, 354-362.
Kuei et al., "Pulmonary toxicity of recombinant human tumor necrosis factor," Chest, 1989, 96, 334-8.
Kurzrock et al., "Phase I study of a combination of recombinant tumor necrosis factor-alpha and recombinant interferon-gamma in cancer patients," J Interferon Res, 1989, 9, 435-44.
Larock, "Comprehensive Organic Transformations," 1989, VCH Publishers, Inc., New York.
Leverson et al., "Potent and selective small-molecule MCL-1 inhibitors demonstrate on-target cancer cell killing activity as single agents and in combination with ABT-263 (navitoclax)," Cell Death Dis, 2015, 6, e1590.
Levinson et al., "A conserved water-mediated hydrogen bond network defines bosutinib's kinase selectivity," Nat Chem Biol, 2014, 10, 127-32.
Li et al., "A TAK1 Signaling Pathway Critically Regulates Myocardial Survival and Remodeling," Circulation, 2014, 130(24):2162-2172.
Lieberman et al., "Pharmaceutical Dosage Forms: Tablets," 1981, Marcel Dekker, Inc., New York.
Limenitakis et al., "Functional genetics in Apicomplexa: potentials and limits," FEBS Lett., 2011, 585:1579-1588.
Lin et al., "The role of TAK1 expression in thyroid cancer," Int J Clin Exp Pathol, 2015, 8, 14449-56.
Liu et al., "Activation of TGF-beta activated kinase 1 promotes colon mucosal pathogenesis in inflammatory bowel disease," Physiol Rep, 2017, 5(7): e13181.
Loog et al., "Bi-substrate analogue ligands for affinity chromatography of protein kinases," FEBS Lett, 2000, 480, 244-8.
Lopez-Barragan et al., "Directional gene expression and antisense transcripts in sexual and asexual stages of Plasmodium falciparum," BMC Genomics, 2011, 12:587.
Lu et al., "Hijacking the E3 Ubiquitin Ligase Cereblon to Efficiently Target BRD4," Chem Biol, 2015, 22, 755-63.
Madelian et al., "Affinity chromatography of creatine kinase," Anal Biochem, 1975, 64, 517-20.
Main et al., "Therapeutic efficacy of multiple intravenous infusions of anti-tumor necrosis factor alpha monoclonal antibody combined with low-dose weekly methotrexate in rheumatoid arthritis," Arthritis Rheum, 1998, 41, 1552-63.
Manning et al., "The protein kinase complement of the human genome," Science, 2002, 298, 1912-34.
Maroulakou et al., Prostate and mammary adenocarcinoma in transgenic mice carrying a rat C3(1) simian virus 40 large tumor antigen fusion gene. Proc Natl Acad Sci USA, 1994, 91, 11236-40.
Maxwell et al., "TNF-alpha inhibitors for ankylosing spondylitis," Cochrane Database Syst Rev, 2015, (4):CD005468.
McNamara et al., "Targeting Plasmodium PI(4)K to eliminate malaria," Nature, 2013, 504(7479):248-253.
Meng et al., "Identification of TGF-beta-activated kinase 1 as a possible novel target for renal cell carcinoma intervention," Biochemical and Biophysical Research Communications, 2014, 453, 106-111.
Minor et al., "HKL-3000: the integration of data reduction and structure solution—from diffraction images to an initial model in minutes," Acta Crystallogr D Biol Crystallogr, 2006, 62, 859-66.
Miura et al., "Identification of a selective inhibitor of transforming growth factor beta-activated kinase 1 by biosensor-based screening of focused libraries," Bioorg Med Chem Lett, 2017, 27, 1031-1036.
Moll et al., "Methods in Malaria Research," 6th ed., 2013, Glasgow.

Moore et al., "Mice deficient in tumor necrosis factor-alpha are resistant to skin carcinogenesis," Nat Med, 1999, 5, 828-31.
Mori et al., "Transactivation of the interleukin-1alpha promoter by human T-cell leukemia virus type I and type II Tax proteins," Blood, 1996, 87, 3410-7.
Morioka et al., "TAK1 regulates hepatic lipid homeostasis through SREBP," Oncogene, 2016, 35, 3829-38.
Muhlradt et al., "Epothilone B stabilizes microtubuli of macrophages like taxol without showing taxol-like endotoxin activity," Cancer Res., 1997, 57(16):3344-3346.
Muraoka et al., "Discovery of a potent and highly selective transforming growth factor beta receptor-associated kinase 1 (TAK1) inhibitor by structure based drug design (SBDD)," Bioorg Med Chem, 2016, 24, 4206-17.
Murshudov et al., "REFMAC5 for the refinement of macromolecular crystal structures," Acta Crystallogr D Biol Crystallogr, 2011, 67, 355-67.
Nagar et al., "Structural basis for the autoinhibition of c-Abl tyrosine kinase," Cell, 2003, 112, 859-71.
Neil et al., "Altered TAB1:IKK interaction promotes TGF-beta-mediated NF-kappaB activation during breast cancer progression," Cancer Res, 2008, 68, 1462-70.
Neklesa et al., "Targeted protein degradation by PROTACs," Pharmacol Ther, 2017, 174, 138-144.
Neubert et al., "Acute inhibition of TAK1 protects against neuronal death in cerebral ischemia," Cell Death Differ, 2011, 18, 1521-30.
Neuzillet et al., "Targeting the TGFbeta pathway for cancer therapy," Pharmacol Ther, 2015, 147, 22-31.
Nicolaou et al., "Synthesis of epothilones A and B in solid and solution phase," Nature, 1997, 387:268-272.
Nikolaou et al., "Inactivation of the deubiquitinase CYLD in hepatocytes causes apoptosis, inflammation, fibrosis, and cancer," Cancer Cell, 2012, 21, 738-50.
Nweke et al., "Mechanical characterisation of agarose-based chromatography resins for biopharmaceutical manufacture," Journal of Chromatography A, 2017, 1530: 129-137.
Omori et al., "TAK1 is a master regulator of epidermal homeostasis involving skin inflammation and apoptosis," J Biol Chem, 2006, 281, 19610-7.
Omori et al., "TAK1 regulates reactive oxygen species and cell death in keratinocytes, which is essential for skin integrity," J Biol Chem, 2008, 283, 26161-8.
Onuora, "Rheumatoid arthritis: JAK-ing up inadequate RA therapy," Nature Reviews Rheumatology, 2017, advance online publication.
Panda et al., "Differential effects of vinblastine on polymerization and dynamics at opposite microtubule ends," J. Biol. Chem., 1996, 271(47):29807-29812.
Panda et al., "Stabilization of microtubule dynamics by estramustine by binding to a novel site in tubulin: A possible mechanistic basis for its antitumor action," Proc. Natl. Acad. Sci. USA, 1997, 94(20):10560-10564.
Pap et al., "Cartilage damage in osteoarthritis and rheumatoid arthritis—two unequal siblings," Nat Rev Rheumatol, 2015, 11, 606-15.
Paquette, "Encyclopedia of Reagents for Organic Synthesis," 1995, John Wiley & Sons, New York.
Peppel et al., "A Tumor-Necrosis-Factor (Tnf) Receptor-Igg Heavy-Chain Chimeric Protein as a Bivalent Antagonist of Tnf Activity," Journal of Experimental Medicine, 1991, 174, 1483-1489.
Philip et al., "Characterization of a UBC13 kinase in Plasmodium falciparum," Proceedings of the National Academy of Sciences of the United States of America, 2007, 104(19):7845-7850.
Phong et al., "P38 Mitogen-Activated Protein Kinase Promotes Cell Survival in Response to DNA Damage but Is Not Required for the G2 DNA Damage Checkpoint in Human Cancer Cells," Molecular and Cellular Biology, 2010, 30, 3816-3826.
Powers et al., "Discovery and initial SAR of inhibitors of interleukin-1 receptor-associated kinase-4," Bioorg Med Chem Lett, 2006, 16, 2842-5.
Powrie et al., "Inhibition of Th1 responses prevents inflammatory bowel disease in scid mice reconstituted with CD45RBhi CD4+ T cells," Immunity, 1994, 1, 553-62.

(56) References Cited

OTHER PUBLICATIONS

Qian et al., "IRAK-mediated translocation of TRAF6 and TAB2 in the interleukin-1-induced activation of NFkappa B," J Biol Chem, 2001, 276, 41661-7.

Radfar et al., "Synchronous culture of Plasmodium falciparum at high parasitemia levels," Nature protocols, 2009, 4(12):1899-1915.

Reiley et al., "Negative regulation of JNK signaling by the tumor suppressor CYLD," J Biol Chem, 2004, 279, 55161-7.

Rhyasen et al., "IRAK signalling in cancer," Br J Cancer, 2015, 112, 232-7.

Roe et al., "Structural basis for inhibition of the Hsp90 molecular chaperone by the antitumor antibiotics radicicol and geldanamycin," Journal of Medicinal Chemistry, 1999, 42(2):260-266.

Roelofs et al., "The Expression of toll-like receptors 3 and 7 in rheumatoid arthritis synovium is increased and costimulation of toll-like receptors 3, 4, and 7/8 results in synergistic cytokine production by dendritic cells," Arthritis and Rheumatism, 2005, 52, 2313-2322.

Roh et al., "TAK1 regulates hepatic cell survival and carcinogenesis," J Gastroenterol, 2014, 49, 185-94.

Ryall et al., "Identifying kinase dependency in cancer cells by integrating high-throughput drug screening and kinase inhibition data," Bioinformatics, 2015, 31, 3799-806.

Safina et al., "TAK1 is required for TGF-beta 1-mediated regulation of matrix metalloproteinase-9 and metastasis," Oncogene, 2008, 27, 1198-1207.

Safina et al., "TAK1-TAB2 signaling contributes to bone destruction by breast carcinoma cells," Mol Cancer Res, 2011, 9, 1042-53.

Sakamoto et al., "Protacs: chimeric molecules that target proteins to the Skp1-Cullin-F box complex for ubiquitination and degradation," Proc Natl Acad Sci USA, 2001, 98, 8554-9.

Sakamoto, "Chimeric molecules to target proteins for ubiquitination and degradation," Methods Enzymol, 2005, 399, 833-47.

Sakurai, "Targeting of TAK1 in inflammatory disorders and cancer," Trends Pharmacol Sci, 2012, 33, 522-30.

Sanjo et al., "TAB2 is essential for prevention of apoptosis in fetal liver but not for interleukin-1 signaling," Mol Cell Biol, 2003, 23, 1231-1238.

Sato et al., "Essential function for the kinase TAK1 in innate and adaptive immune responses," Nat Immunol, 2005, 6, 1087-95.

Sayama et al., "Transforming growth factor-beta-activated kinase 1 is essential for differentiation and the prevention of apoptosis in epidermis," J Biol Chem, 2006, 281, 22013-20.

Schett et al., "Interleukin-1 function and role in rheumatic disease," Nat Rev Rheumatol, 2016, 12, 14-24.

Scholz et al., "Autoactivation of Transforming Growth Factor beta-activated Kinase 1 Is a Sequential Bimolecular Process," Journal of Biological Chemistry, 2010, 285, 25753-25766.

Shim et al., "TAK1, but not TAB1 or TAB2, plays an essential role in multiple signaling pathways in vivo," Genes & Development, 2005, 19, 2668-2681.

Sidiropoulos et al., "Differential drug resistance to anti-tumour necrosis factor agents in rheumatoid arthritis," Ann Rheum Dis, 2006, 65, 701-3.

Singh et al., "Regulation of TAK1 Activation by Epigallocatechin-3-Gallate in Rheumatoid Arthritis Synovial Fibroblasts: Suppression of K(63)-Linked Autoubiquitination of Tumor Necrosis Factor Receptor-Associated Factor 6," Arthritis Rheumatol, 2016, 68, 347-58.

Singh et al., "TAK1 inhibition promotes apoptosis in KRAS-dependent colon cancers," Cell, 2012, 148, 639-50.

Smith et al., "March's Advanced Organic Chemistry," 5th ed., 2001, John Wiley & Sons, Inc., New York.

Solyakov et al., "Global kinomic and phospho-proteomic analyses of the human malaria parasite *Plasmodium falciparum*," Nature Communications, 2011, 2:565.

Sorrell, "Organic Chemistry," 2nd ed., 1999, University Science Books, Sausalito.

Sorrentino et al., "The type I TGF-beta receptor engages TRAF6 to activate TAK1 in a receptor kinase-independent manner," Nat Cell Biol, 2008, 10, 1199-207.

Soucy et al., "An inhibitor of NEDD8-activating enzyme as a new approach to treat cancer," Nature, 2009, 458(7239):732-736.

Spadaro et al., "Remission in ankylosing spondylitis treated with anti-TNF-alpha drugs: a national multicentre study," Rheumatology (Oxford), 2013, 52, 1914-9.

St Clair et al., "The relationship of serum infliximab concentrations to clinical improvement in rheumatoid arthritis: results from ATTRACT, a multicenter, randomized, double-blind, placebo-controlled trial," Arthritis and Rheum, 2002, 46, 1451-9.

Strippoli et al., "p38 maintains E-cadherin expression by modulating TAK1-NF-kappa B during epithelial-to-mesenchymal transition," J Cell Sci, 2010, 123, 4321-31.

Takaesu et al., "Interleukin-1 (IL-1) receptor-associated kinase leads to activation of TAK1 by inducing TAB2 translocation in the IL-1 signaling pathway," Mol Cell Biol, 2001, 21, 2475-84.

Takahashi et al., "MUC1-C activates the TAK1 inflammatory pathway in colon cancer," Oncogene, 2015, 34, 5187-97.

Talevich et al., "Structural and evolutionary divergence of eukaryotic protein kinases in Apicomplexa," BMC Evolutionary Biology, 2011, 11:321.

Tan et al., "Discovery of type II inhibitors of TGFbeta-activated kinase 1 (TAK1) and mitogen-activated protein kinase kinase kinase 2 (MAP4K2)," J Med Chem, 2015, 58, 183-96.

Tewari et al., "The systematic functional analysis of Plasmodium protein kinases identifies essential regulators of mosquito transmission," Cell Host & Microbe, 2010, 8(4):377-387.

Tokunaga et al., "Involvement of linear polyubiquitylation of NEMO in NF-kappaB activation," Nat Cell Biol, 2009, 11, 123-32.

Totzke, "Targeting Transforming Growth Factor Beta-Activated Kinase 1 as a Therapeutic Strategy in Cancer and Immune Disease," Thesis, Mar. 20, 2018 (207 pages).

Totzke, "Targeting Transforming Growth Factor Beta-Activated Kinase 1 as a Therapeutic Strategy in Cancer and Immune Disease," Dissertation, Sep. 8, 2017 (86 pages).

Totzke et al., "Takinib, a Selective TAK1 Inhibitor, Broadens the Therapeutic Efficacy of TNF-α Inhibition for Cancer and Autoimmune Disease," Cell Chem. Biol., 2017, 24(8):1029-1039.e7.

Tran et al., "Molecular interactions between T cells and fibroblast-like synoviocytes: role of membrane tumor necrosis factor-alpha on cytokine-activated T cells," Am J Pathol, 2007, 171(5): 1588-1598.

Uhlen et al., "Proteomics. Tissue-based map of the human proteome," Science, 2015, 347, 1260419.

Uhlen, "Affinity as a tool in life science," Biotechniques, 2008, 44, 649-654.

Vaiopoulos et al., "NF-κB in colorectal cancer," Journal of Molecular Medicine, 2013, 91, 1029-1037.

Van Eden, "XToll, a recombinant chaperonin 10 as an anti-inflammatory immunomodulator," Curr Opin Investig Drugs, 2008, 9(5):523-33.

Van Schouwenburg et al., "Adalimumab elicits a restricted anti-idiotypic antibody response in autoimmune patients resulting in functional neutralisation," Ann Rheum Dis, 2013, 72, 104-9.

Vasanthi et al., "Role of tumor necrosis factor-alpha in rheumatoid arthritis: a review," APLAR Journal of Rheumatology, 2007, 10, 270-274.

Vasquez et al., "Nanomolar concentrations of nocodazole alter microtubule dynamic instability in vivo and in vitro," Mol. Biol. Cell., 1997, 8(6):973-985.

Verhoef et al., "Isolated limb perfusion with melphalan and TNF-alpha in the treatment of extremity sarcoma," Curr Treat Options Oncol, 2007, 8, 417-27.

Vince et al., "TRAF2 Must Bind to Cellular Inhibitors of Apoptosis for Tumor Necrosis Factor (TNF) to Efficiently Activate NF-kappa B and to Prevent TNF-induced Apoptosis," Journal of Biological Chemistry, 2009, 284, 35906-35915.

Wajant et al., "The TNF-receptor-associated factor family—Scaffold molecules for cytokine receptors, kinases and their regulators," Cellular Signalling, 2001, 13, 389-400.

Wajant et al., "Tumor necrosis factor signaling," Cell Death Differ, 2003, 10, 45-65.

(56) References Cited

OTHER PUBLICATIONS

Wan et al., "The kinase TAK1 integrates antigen and cytokine receptor signaling for T cell development, survival and function," Nat Immunol, 2006, 7, 851-8.
Wang et al., "Belinostat-induced apoptosis and growth inhibition in pancreatic cancer cells involve activation of TAK1-AMPK signaling axis," Biochem Biophys Res Commun, 2013, 437, 1-6.
Wang et al., "TAK1 inhibitor NG25 enhances doxorubicin-mediated apoptosis in breast cancer cells," Sci Rep, 2016, 6, 32737.
Wang et al., "TAK1 is a ubiquitin-dependent kinase of MKK and IKK," Nature, 2001, 412, 346-351.
Wang et al., "Transforming growth factor beta-activated kinase 1 (TAK1)-dependent checkpoint in the survival of dendritic cells promotes immune homeostasis and function," Proc Natl Acad Sci U S A, 2012, 109, E343-52.
Ward et al., "Protein kinases of the human malaria parasite *Plasmodium falciparum*: the kinome of a divergent eukaryote," BMC Genomics, 2004, 5:79.
Wenninger et al., "CTFA Cosmetic Ingredient Handbook," 2nd ed., 1992, The Cosmetic, Toiletry, and Fragrance Association, Washington, D.C., pp. 587-592.
Winter et al., "Phthalimide conjugation as a strategy for in vivo target protein degradation," Science, 2015, 348, 1376-1381.
Woodgett, "Use of Peptide-Substrates for Affinity Purification of Protein Serine Kinases," Analytical Biochemistry, 1989, 180, 237-241.
Wrana et al., "TGFβ signals through a heteromeric protein kinase receptor complex," Cell, 1992, 71, 1003-1014.
Wu et al., "Mechanism and in vitro pharmacology of TAK1 inhibition by (5Z)-7-Oxozeaenol," ACS Chem Biol, 2013, 8, 643-50.
Wu et al., "TAK1 as the mediator in the protective effect of propofol on renal interstitial fibrosis induced by ischemia/reperfusion injury," Eur J Pharmacol, 2017, 811, 134-140.
Wu et al., "Ubiquitin-conjugating enzyme Ubc13 controls breast cancer metastasis through a TAK1-p38 MAP kinase cascade," Proceedings of the National Academy of Sciences of the United States of America, 2014, 111(38):13870-13875.
Greene and Wuts et al., "Greene's Protective Groups in Organic Synthesis," 2nd ed., 1991, John Wiley & Sons, New York.
Greene and Wuts et al., "Greene's Protective Groups in Organic Synthesis," 3rd ed., 1999, John Wiley & Sons, New York.
Wuts et al., "Greene's Protective Groups in Organic Synthesis," 4th ed., 2007, John Wiley & Sons, New York.
Xia et al., "Direct activation of protein kinases by unanchored polyubiquitin chains," Nature, 2009, 461, 114-9.
Xu et al., "The ubiquitin-activating enzyme E1 as a therapeutic target for the treatment of leukemia and multiple myeloma," Blood, 2010, 115(11):2251-2259.
Yan et al., "Cellular localization of tumor necrosis factor-alpha following acute spinal cord injury in adult rats," J Neurotrauma, 2001, 18, 563-8.
Ying et al., "Inhibition of ovarian cancer cell growth by a novel TAK1 inhibitor LYTAK1," Cancer Chemother Pharmacol, 2015, 76, 641-50.
Yu et al., "RNA sequencing of pancreatic circulating tumour cells implicates WNT signalling in metastasis," Nature, 2012, 487, 510-3.
Zer et al., "Identification of genomic targets downstream of p38 mitogen-activated protein kinase pathway mediating tumor necrosis factor-α signaling," Physiological genomics, 2007, 31, 343-351.
Zhang et al., "Confirmation of primary active substances from high throughput screening of chemical and biological populations: a statistical approach and practical considerations," Journal of Combinatorial Chemistry, 2000, 2(3):258-265.
Zhang et al., "Targeting cancer with small molecule kinase inhibitors," Nature Reviews—Cancer, 2009, 9(1):28-39.
Zhang et al., "Transforming growth factor beta-activated kinase 1 inhibitor suppresses the proliferation in triple-negative breast cancer through TGFbeta/TGFR pathway," Chem Biol Drug Des, 2017, 90(3):450-455.
Zhou et al., "LYTAK1, a novel TAK1 inhibitor, suppresses KRAS mutant colorectal cancer cell growth in vitro and in vivo," Tumour Biol, 2015, 36, 3301-8.
Zhu et al., "Expression of TAK1/TAB1 expression in non-small cell lung carcinoma and adjacent normal tissues and their clinical significance," International Journal of Clinical and Experimental Pathology, 2015, 8, 15801-15807.
Zink et al., "Treatment continuation in patients receiving biological agents or conventional DMARD therapy," Ann Rheum Dis, 2005, 64, 1274-9.
Wang et al., "Discovery of potent, selective, and orally bioavailable inhibitors of interleukin-1 receptor-associate kinase-4," Bioorganic & Medicinal Chemistry Letters, 2015, 25: 5546-5550.

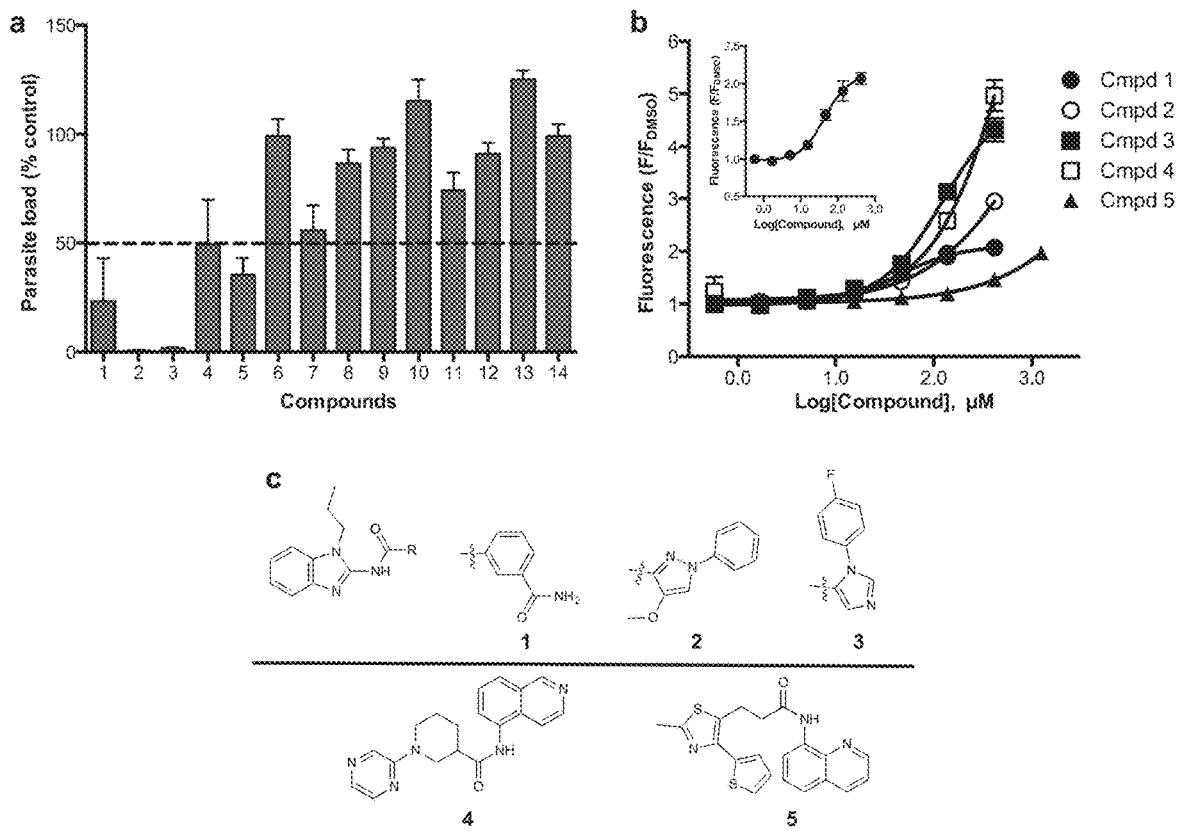
FIG. 2A-C
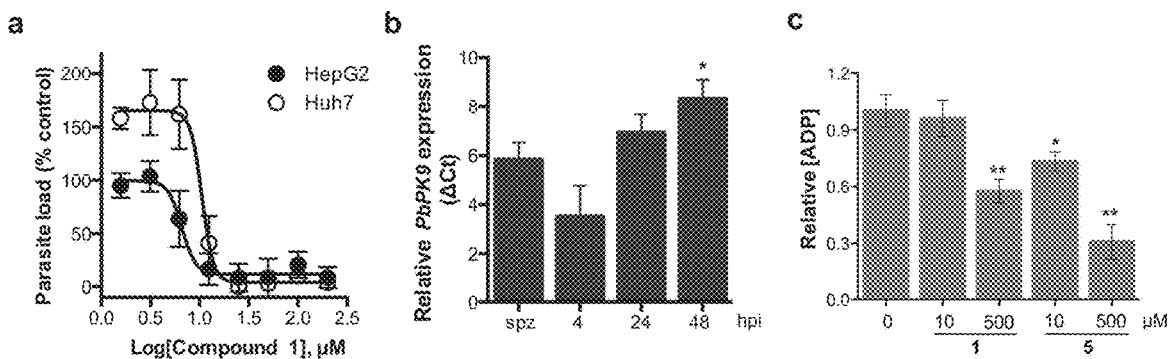
FIG. 3A-C

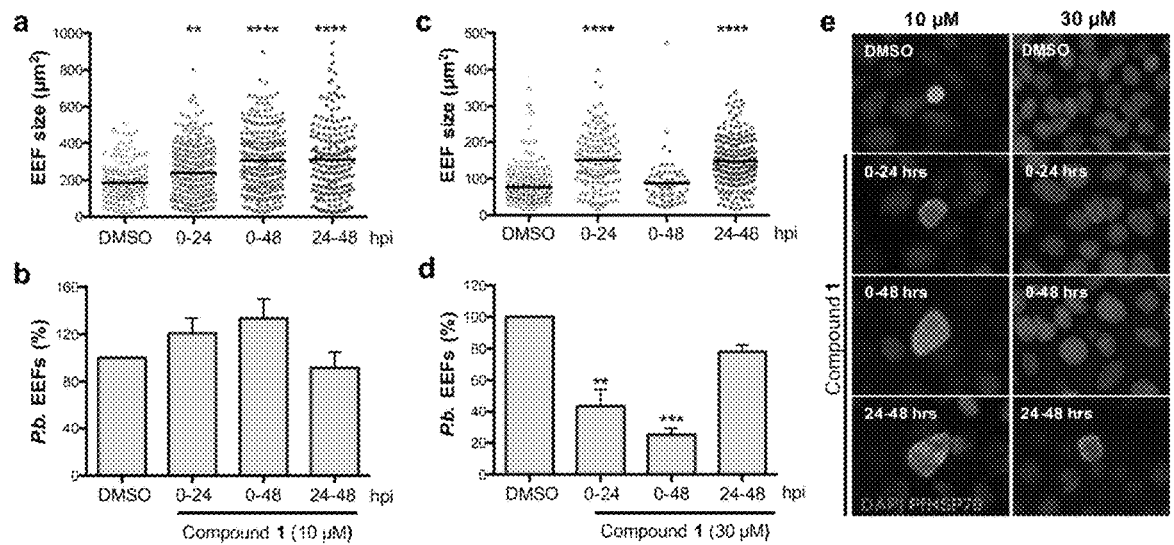
FIG. 4A-E
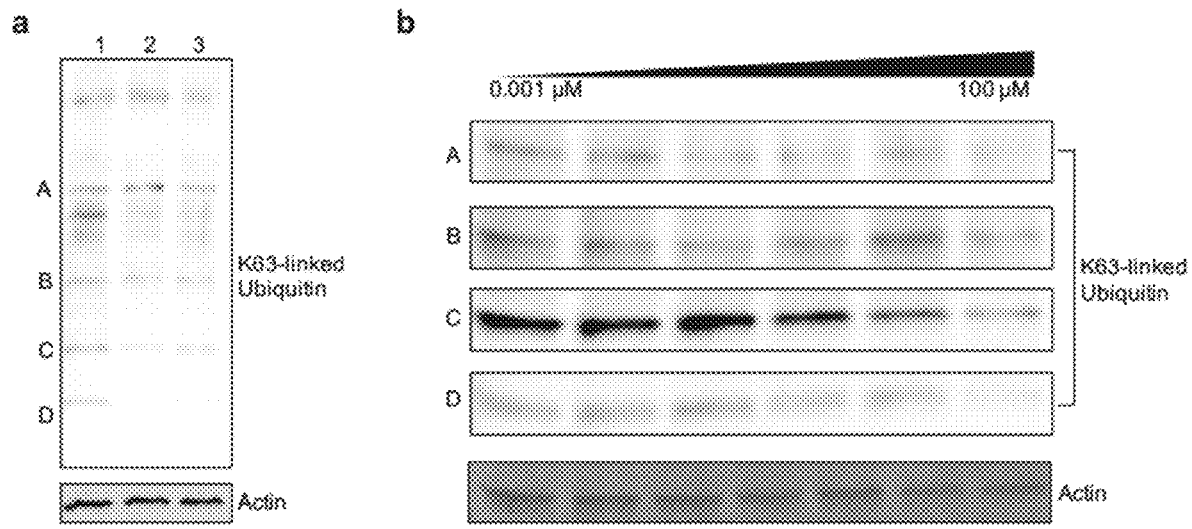
FIG. 5A-B

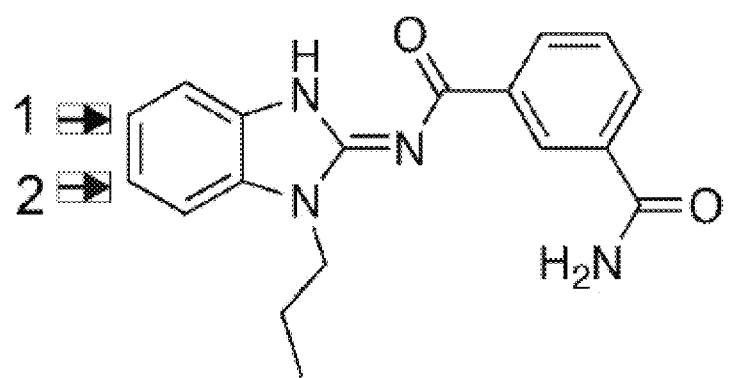
FIG. 13

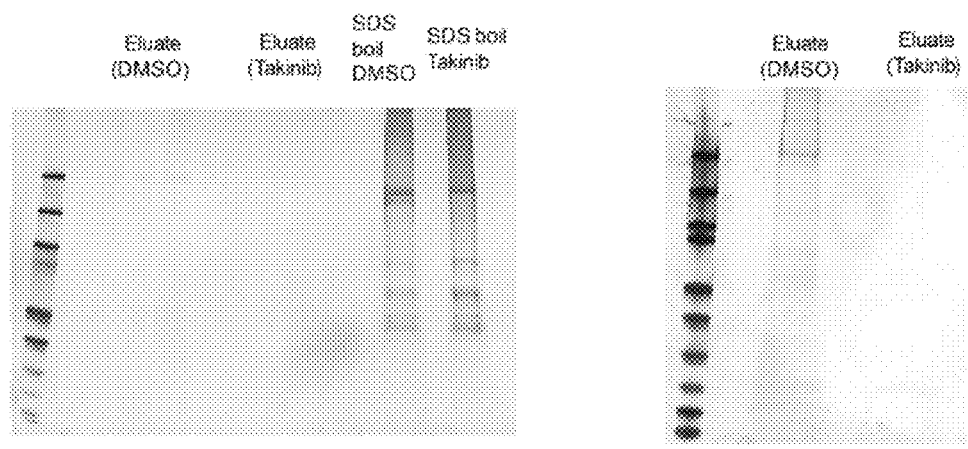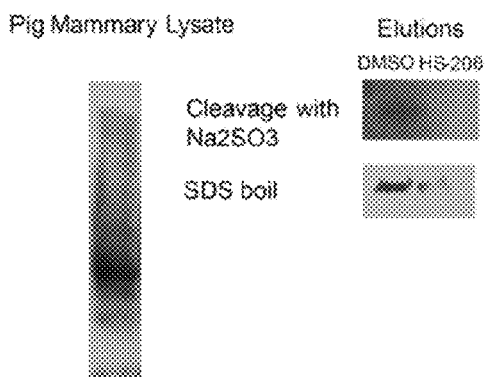
FIG. 16

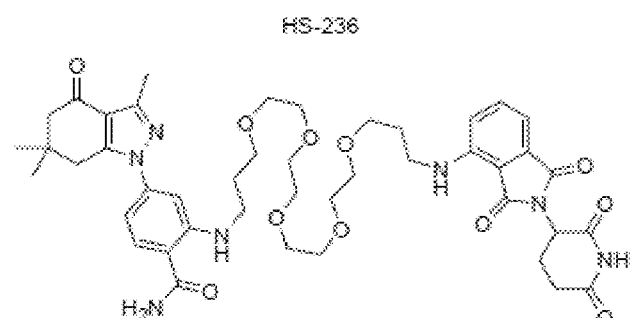
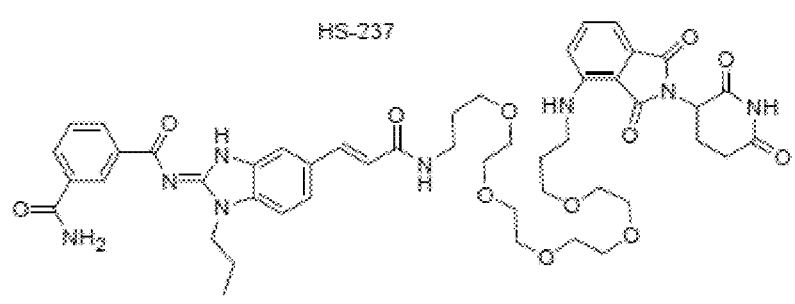
FIG. 20

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Synthetic

<400> SEQUENCE: 1
aattatgggc cgcttattgg                                              20

<210> SEQ ID NO 2
<211> LENGTH: 20
<212> TYPE: DNA
<213> ORGANISM: Artificial Sequence
<220> FEATURE:
<223> OTHER INFORMATION: Synthetic

<400> SEQUENCE: 2
tgactcaagg ttacccacca                                              20

<210> SEQ ID NO 3
<211> LENGTH: 23
<212> TYPE: DNA
<213> ORGANISM: Artificial Sequence
<220> FEATURE:
<223> OTHER INFORMATION: Synthetic

<400> SEQUENCE: 3
ggttttgacg tttatgtggg cat                                          23

<210> SEQ ID NO 4
<211> LENGTH: 21
<212> TYPE: DNA
<213> ORGANISM: Artificial Sequence
<220> FEATURE:
```

```
<223> OTHER INFORMATION: Synthetic

<400> SEQUENCE: 4
ggcatgtcgt aaacgcaaga a                                            21

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
cgggcgcggt cggtaaagtt                                              20

<210> SEQ ID NO 6
<211> LENGTH: 20
<212> TYPE: DNA
<213> ORGANISM: Artificial Sequence
<220> FEATURE:
<223> OTHER INFORMATION: Synthetic

<400> SEQUENCE: 6
gtcgggaaga cctgccacgc                                              20
```

SUBSTITUTED BENZIMIDAZOLES AS INHIBITORS OF TRANSFORMING GROWTH FACTOR-β KINASE

RELATED APPLICATIONS

This application claims the benefit of U.S. provisional application Ser. No. 62/649,923, filed Mar. 29, 2018, and is a continuation-in-part of U.S. application Ser. No. 15/720,731, filed Sep. 29, 2017, which claims the benefit of U.S. provisional application Ser. No. 62/401,733, filed Sep. 29, 2016. The entire contents of these applications are incorporated herein by reference.

TECHNICAL FIELD

This application relates to inhibitors of transforming growth factor β-activated kinase 1 and uses in the treatment of inflammatory conditions, autoimmune conditions, and cancer.

SEQUENCE LISTING

The sequence listing is filed with the application in electronic format only and is incorporated by reference herein. The sequence listing text file "028193-9243-US01_As_Filed_Sequence_Listing.txt" was created on Dec. 7, 2017, and is 1,406 bytes in size.

BACKGROUND

Transforming growth factor β-activated kinase 1 (TAK1, MAP3K7) is a member of the MAP3K family and plays a key role in the signaling pathways of inflammation and cell survival. TAK1 is activated by a number of pro-inflammatory signals including TGFβ3, TNFα, Toll-like receptor ligands and IL-1, resulting in the induction of key inflammatory and pro-survival genes such as NFκB and c-Jun-N-terminal kinases (JNKs). TAK1 inhibition induces death of cancer cells and thus, TAK1 has emerged as a potential therapeutic target for cancer and inflammatory diseases.

Prior screens by others for inhibitors of TAK1 identified the fungal metabolite 5(Z)-7-oxozeanol. However, this molecule has selectivity issues such that it targets members of the MAP2K family. Medicinal chemistry groups used the chemical scaffold of 5(Z)-7-oxozeanol as a lead molecule to generate more selective inhibitors of TAK1. Their efforts identified additional molecules namely, LYTAK1, PF-04358168, and AZ-TAK1. None of these inhibitors have been advanced clinically, largely due to selectivity issues in vivo.

SUMMARY

In one aspect, provided is a compound according to Formula (I):

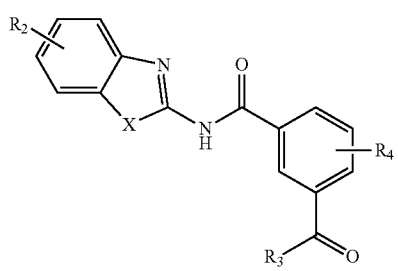

(I)

or a stereoisomer or salt thereof;
wherein
X is $NR_1$ or S;
$R_1$ is H, $C_{1-4}$ alkyl, $C_{1-4}$ carbonyl, or $C_{1-4}$ carboxyl;
$R_2$ is H, $C_{1-4}$ alkyl, $C_{1-4}$ alkoxy, or halogen;
$R_3$ is OH, $C_{1-4}$ alkoxy, or amino; and
$R_4$ is H, $C_{1-4}$ alkyl, $C_{1-4}$ alkoxy, or halogen;
wherein each $C_{1-4}$ alkyl may be independently substituted by halo, hydroxy, or amino;
wherein if X is $NR_1$, $R_1$ is not propyl when $R_3$ is $NH_2$.

In an aspect, provided is a method of treating a disease modulated by transforming growth factor β activated kinase 1 (TAK1), comprising administering to a subject in need thereof a therapeutically effective amount of compound according to Formula (I):

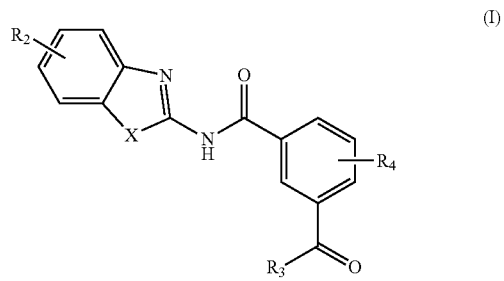

(I)

or a stereoisomer or salt thereof;
wherein
X is $NR_1$ or S;
$R_1$ is H, $C_{1-4}$ alkyl, $C_{1-4}$ hydroxy alkyl, $C_{1-4}$ carbonyl, $C_{1-4}$ carboxyl, or $C_{1-4}$ aminoalkyl;
$R_2$ is H, $C_{1-4}$ alkoxy, or halogen;
$R_3$ is OH, $C_{1-4}$ alkoxy, or amino;
$R_4$ is H, $C_{1-4}$ alkyl, $C_{1-4}$ alkoxy, or halogen.

In an aspect, provided is a pharmaceutical composition comprising a compound according to Formula (I) or a stereoisomer or salt thereof and pharmaceutically acceptable excipient.

In another aspect are provided compounds of Formula (I), or a tautomer or salt thereof; wherein
X is $NR_1$ or S;
$R_1$ is H, $C_{1-6}$ alkyl, $C_{1-4}$ carbonyl, or $C_{1-4}$ carboxyl;
$R_2$ is H, $C_{1-4}$ alkyl, $C_{1-4}$ alkoxy, or halogen;
$R_3$ is OH, $C_{1-4}$ alkoxy, $NH_2$, $NH(C_{1-4}$ alkyl), or $N(C_{1-4}$ alkyl)($C_{1-4}$ alkyl); and
$R_4$ is H, $C_{1-4}$ alkyl, $C_{1-4}$ alkoxy, or halogen;
wherein the $C_{1-4}$ alkyl and $C_{1-6}$ alkyl of $R_1$, $R_2$, and $R_4$ are optionally independently substituted by halo, hydroxy, $NH_2$, $NH(C_{1-4}$ alkyl), or $N(C_{1-4}$ alkyl)($C_{1-4}$ alkyl);
wherein the compound of Formula (I) is not

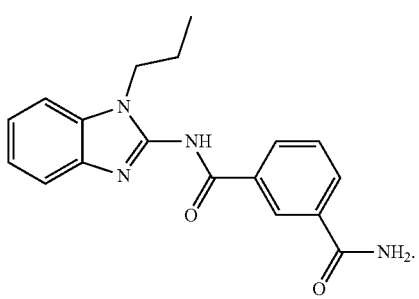 [SMILES: CCCn1c(NC(=O)c2cccc(C(N)=O)c2)nc2ccccc21]

Another aspect provides a method of treating a disease modulated by transforming growth factor β activated kinase 1 (TAK1), comprising administering to a subject in need thereof a therapeutically effective amount of a compound according to Formula (I), or a tautomer or salt thereof, wherein X is $NR_1$ or S;
$R_1$ is H, $C_{1-6}$ alkyl, $C_{1-4}$ carbonyl, or $C_{1-4}$ carboxyl;
$R_2$ is H, $C_{1-4}$ alkyl, $C_{1-4}$ alkoxy, or halogen;
$R_3$ is OH, $C_{1-4}$ alkoxy, $NH_2$, $NH(C_{1-4}$ alkyl), or $N(C_{1-4}$ alkyl)($C_{1-4}$ alkyl); and
$R_4$ is H, $C_{1-4}$ alkyl, $C_{1-4}$ alkoxy, or halogen;
wherein the $C_{1-4}$ alkyl and $C_{1-6}$ alkyl of $R_1$, $R_2$, and $R_4$ are optionally independently substituted by halo, hydroxy, $NH_2$, $NH(C_{1-4}$ alkyl), or $N(C_{1-4}$ alkyl)($C_{1-4}$ alkyl).

Another aspect provides a pharmaceutical composition comprising a compound according to Formula (I), or a tautomer or pharmaceutically acceptable salt thereof, and a pharmaceutically acceptable carrier, wherein X is $NR_1$ or S;
$R_1$ is H, $C_{1-6}$ alkyl, $C_{1-4}$ carbonyl, or $C_{1-4}$ carboxyl;
$R_2$ is H, $C_{1-4}$ alkyl, $C_{1-4}$ alkoxy, or halogen;
$R_3$ is OH, $C_{1-4}$ alkoxy, $NH_2$, $NH(C_{1-4}$ alkyl), or $N(C_{1-4}$ alkyl)($C_{1-4}$ alkyl); and
$R_4$ is H, $C_{1-4}$ alkyl, $C_{1-4}$ alkoxy, or halogen;
wherein the $C_{1-4}$ alkyl and $C_{1-6}$ alkyl of $R_1$, $R_2$, and $R_4$ are optionally independently substituted by halo, hydroxy, $NH_2$, $NH(C_{1-4}$ alkyl), or $N(C_{1-4}$ alkyl)($C_{1-4}$ alkyl).

In another aspect, provided is a compound according to Formula (II):

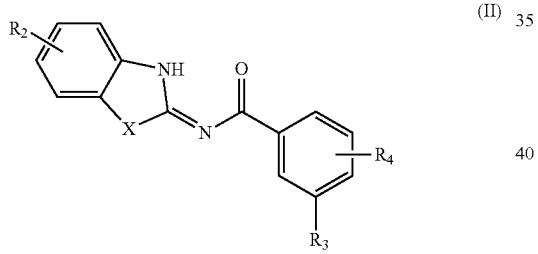

(II)

or a tautomer or salt thereof;
wherein
X is $NR_1$ or S;
$R_1$ is H, $C_{1-6}$ alkyl, $C_{1-4}$ carbonyl, $C_{1-4}$ carboxyl, or $-L_1-G_1$;
$L_1$ is

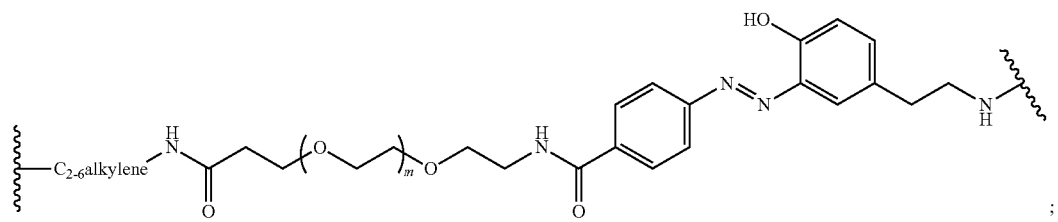

;

G$_1$ is H, —C(O)OC$_{1-4}$alkyl, or —C(NH)O-agarose resin;
m is 1, 2, 3, 4, or 5;
R$_2$ is H, C$_{1-4}$ alkyl, C$_{1-4}$ alkoxy, halogen, or L$_2$-R$_6$;
L$_2$ is —CH═CH— or —CH$_2$CH$_2$—;
R$_6$ is C(O)OH, C(O)OC$_{1-4}$alkyl, C(O)NH$_2$, C(O)NHC$_{1-4}$alkyl, C(O)N(C$_{1-4}$alkyl)$_2$, C(O)NH—C$_{2-6}$alkylene-N(C$_{1-4}$alkyl)$_2$, C(O)NH—C$_{2-6}$alkylene-NH(C$_{1-4}$alkyl), C(O)NH—C$_{2-6}$alkylene-NH$_2$, C(O)N(C$_{1-4}$alkyl)-C$_{2-6}$alkylene-N(C$_{1-4}$alkyl)$_2$, C(O)N(C$_{1-4}$alkyl)-C$_{2-6}$alkylene-NH(C$_{1-4}$alkyl), C(O)N(C$_{1-4}$alkyl)-C$_{2-6}$alkylene-NH$_2$, C(O)NH-L$_3$-G$_2$, or C(O)NH-L$_4$-G$_3$;
L$_3$ is

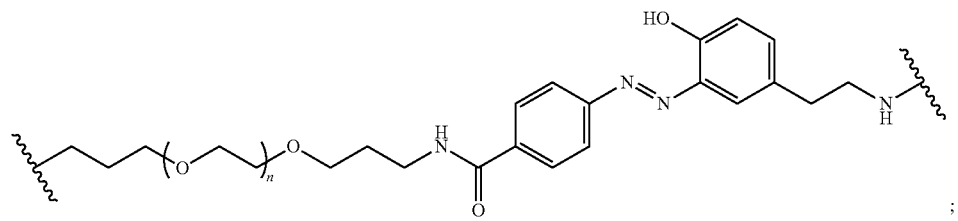

G$_2$ is H, —C(O)OC$_{1-4}$alkyl, or —C(NH)O-agarose resin;
L$_4$ is

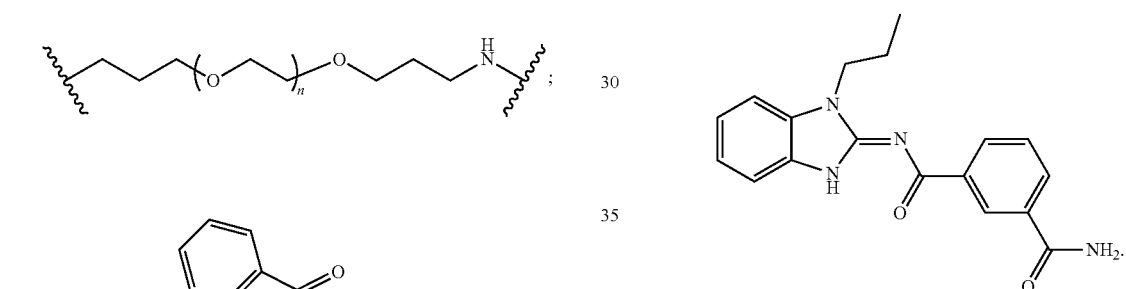

G$_3$ is H,
n is 1, 2, 3, 4, or 5;
R$_3$ is cyano, nitro, or C(O)R$_5$;
R$_4$ is H, C$_{1-4}$ alkyl, C$_{1-4}$ alkoxy, or halogen; and
R$_5$ is OH, C$_{1-4}$ alkoxy, NH$_2$, NH(C$_{1-4}$ alkyl), or N(C$_{1-4}$ alkyl)(C$_{1-4}$ alkyl);

wherein the C$_{1-4}$ alkyl and C$_{1-6}$ alkyl of R$_1$, R$_2$, and R$_4$ are optionally independently substituted by halo, hydroxy, NH$_2$, NH(C$_{1-4}$ alkyl), or N(C$_{1-4}$ alkyl)(C$_{1-4}$ alkyl); and wherein the compound of Formula (II) is not In another aspect, the invention provides a composition comprising a compound of formula (II), or a tautomer or salt thereof, and a carrier.

In another aspect, the invention provides a method of treating a disease modulated by transforming growth factor β activated kinase 1 (TAK1), comprising administering to a subject in need thereof, a therapeutically effective amount of a TAK1 modulator of formula (II), or a tautomer, salt, or pharmaceutical composition thereof.

In another aspect, the invention provides a TAK1 modulator compound of formula (II), or a tautomer, salt, or pharmaceutical composition thereof, for use in the treatment of a disease modulated by transforming growth factor β activated kinase 1.

In another aspect, the invention provides the use of a TAK1 modulator compound of formula (II), or a tautomer, salt, or pharmaceutical composition thereof, for the manufacture of a medicament in the treatment of a disease modulated by transforming growth factor β activated kinase 1.

In a further aspect, the invention provides a kit comprising a compound of formula (II), or tautomer, salt thereof, or composition thereof, and instructions for treating a disease modulated by transforming growth factor β activated kinase 1.

Other aspects will become apparent by consideration of the detailed description and accompanying drawings.

BRIEF DESCRIPTION OF THE DRAWINGS

FIG. 2A-2C show (A) Inhibition of liver stage parasite load by screening actives at 30 μM. Dash line indicates 50% inhibition. Data are normalized to DMSO, vehicle control, and are shown as mean±SEM. (B) Dose-responses of screening actives performed in the ATP pull-down assay. The inset shows the full dose-response for compound 1. n=2 biological experiments. (C) Chemical structures of hit compounds exhibiting liver stage activity.

FIG. 3A-C show the effects of compound 1 on liver stage and cell viability assessment. (A) Dose-response experiments of liver stage inhibition of parasite load in HepG2 and Huh7 cells by compound 1. (B) Quantitative RT-PCR analysis of the expression of P. berghei PK9 transcripts at different time points post-infection in HepG2 cells. Data are mean±SEM in transcript levels relative to sporozoites (0 h post-infection), using Pb 18S rRNA and luc as reference genes. n=4 independent experiments. Statistical analysis was performed using one-way ANOVA (P<0.05) and Tukey's multiple comparison test. *P<0.05 when compared to 4 hours post-infection. (C) Autophosphorylation activity of recombinant PfPK9 is significantly reduced by compound 1 (500 μM) and compound 5 (10, 500 μM). *P<0.01, **P<0.001 versus DMSO challenged reaction. Abbreviation: spz, sporozoites; hpi, hour post-infection.

FIG. 4A-E show that compound 1 treatment leads to increased EEF size. (A, B) (A) Size distribution and (B) percentage of P. b. EEFs in Huh7 cells that were treated with DMSO or 10 μM compound 1 at different time points post-infection. (C, D) (C) Size distribution and (D) percentage of P. b. EEFs in Huh7 cells that were treated with DMSO or 30 μM compound 1 at different time points post-infection. (E) Representative immunofluorescence images of P. b. EEFs in Huh7 cells treated with DMSO, 10 μM or 30 μM compound 1 at various times post-infection. Labelling was performed with anti-HSP70 antibodies (green) and DAPI (blue). Image J software was used to determine the area of EEFs taken from images with the same magnification (10×). Merged images are shown. Data are represented as mean±SEM. n=2 biological replicates. P<0.01, *P<0.001, ****P<0.0001; one-way ANOVA with Dunn's multiple comparisons test. Abbreviation: EEF, exo-erythrocytic form; hpi, hour post-infection.

FIG. 5A-B shows K63-linked ubiquitination in *Plasmodium* parasites treated with novel compounds. (A) Western blot of K63-linked ubiquitin in treated samples. Lane 1; DMSO, lane 2; 30 μM compound 5 and lane 3; 30 μM compound 1. Some proteins appear to be unaffected while others are dramatically less ubiquitinated (K63-linked) in the presence of small molecule compounds, particularly compound 1. (B) Western blot of K63-linked ubiquitin in *Plasmodium* parasite protein extracts treated in dose-dependent concentrations of compound 1, ranging from 0.001 to 100 μM. Further exploration of compound 1 effects on K63-linked ubiquitin revealed several proteins at varying molecular weights exhibiting dose-dependent response, such as protein A, C and D. Others remain unaffected even at 100 μM, such as protein B.

FIG. 13 shows the solvent-exposed regions of Takinib.

FIG. 16 shows affinity chromatography results with TAK1 resin 0.

FIG. 20 shows Hsp90 and TAK1 PROTAC structures.

DETAILED DESCRIPTION

Figure 1:
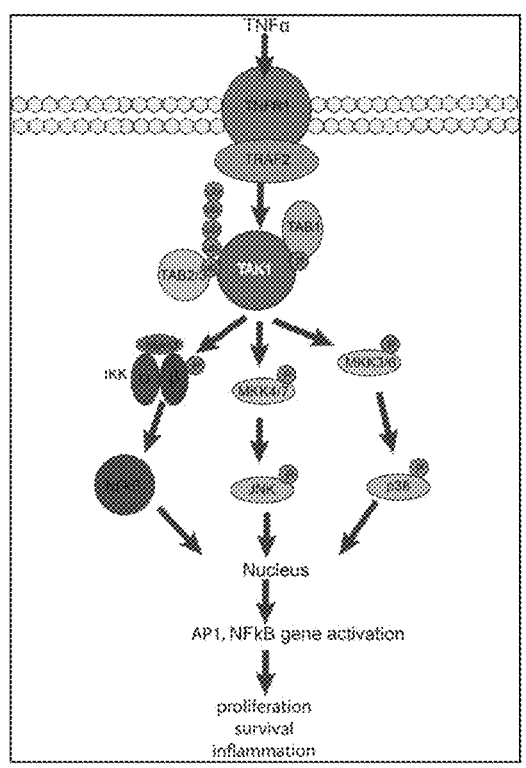
FIG. 1 shows TAK1 dependent signaling events following TNFα stimulation.

In one aspect, provided are novel inhibitors of TAK1. TAK1 is an evolutionarily conserved member of the mitogen-activating kinase family and is involved in pro survival signaling in several cancer types. TAK1 requires interaction with TAK1 binding proteins 1,2,3 (TAB1-3) for its functional activation. Stimulation of cancer cells with the proinflammatory cytokine tumor necrosis factor α (TNFα) leads to TAK1-dependent activation of NFκB, cJun, and p38 MAPK (FIG. 1). The assembly of the TNF-Receptor 1 (TNFR1) complex leads to recruitment of Inhibitor of κB kinase (IKK). TAK1 phosphorylates IKK, which leads to phosphorylation of inhibitor of κB kinase (IκB) and allows translocation of NFκB to the nucleus and transcription of pro survival genes, such as IAP and Bcl-Xl. p38 MAPK signaling gets transiently activated after TNFα stimulation. TAK1 phosphorylates MKK3/4/6, which leads to p38 and cJun activation and subsequent translocation to the nucleus to activate transcription of pro survival genes.

Several studies demonstrated the critical role of TAK1 in survival in KRAS-driven colorectal cancer. RNAi knockdown studies have demonstrated that TAK1 inhibition had the most potent and selective effect on viability in KRAS-dependent versus KRAS independent colorectal cancer cell lines, demonstrating that differential treatment with a TAK1 inhibitor could have beneficial outcomes. A similar therapeutic potential for TAK1 inhibition was found in metastatic breast cancer models, which are also confounded in knockdown studies as opposed to pharmacological inhibition. In both in vitro and in vivo models, downregulation of TAK1 decreased transcription and activity of matrix proteolysis genes and demonstrated the role of TAK1 in angiogenesis and metastasis.

Kinase inhibitors bind in various ways. Some kinase inhibitors target the structurally conserved ATP-binding pocket, which is called Type 1 binding. Such molecules are designed to target the kinase in its active conformation, which is innately challenging due to highly conserved and rigid nature of this conformation. The inactive conformation of kinases is distinct for each kinase, which allows for higher specificity of small molecule therapeutics. Due to the specific amino acids changing their special orientation, this conformation is called "DFG-out", or type 2 binding, which involves a rearrangement of the conserved tripeptide $Mg^{2+}$-binding motif DFG that induces an allosteric binding pocket. Recent structural-activity relationship studies identified structural elements that could induce binding of kinases in the DFG-out conformation.

Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

Section headings as used in this section and the entire disclosure herein are not intended to be limiting.

For the recitation of numeric ranges herein, each intervening number there between with the same degree of precision is explicitly contemplated. For example, for the range 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9 and 7.0 are explicitly contemplated.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4."

The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

The terms "administer", "administering", "administered" or "administration" refer to any manner of providing a compound or a pharmaceutical composition (e.g., one described herein), to a subject or patient. Routes of administration can be accomplished through any means known by those skilled in the art. Such means include, but are not limited to, oral, buccal, intravenous, subcutaneous, intramuscular, transdermal, by inhalation and the like.

"Contacting" as used herein, e.g., as in "contacting a sample" refers to contacting a sample directly or indirectly in vitro, ex vivo, or in vivo (i.e. within a subject as defined herein). Contacting a sample may include addition of a compound to a sample (e.g., a sample comprising cells that contain TAK1), or administration to a subject. Contacting encompasses administration to a solution, cell, tissue, mammal, subject, patient, or human. Further, contacting a cell includes adding an agent to a cell culture.

"Effective amount," as used herein, refers to a dosage or an amount of a compound or a composition effective for eliciting a desired effect. This term as used herein may also refer to an amount effective at bringing about a desired in vivo effect in an animal, e.g., a mammal, e.g., a human. For example, in methods of treating cancer, an effective amount may be an amount sufficient to treat the disorder.

"Member atom" as used herein refers to a polyvalent atom (e.g., a C, O, N, or S atom) in a chain or ring system that constitutes a part of the chain or ring. For example, in pyridine, five carbon atoms and one nitrogen atom are member atoms of the ring. In diethyl ether, four carbon atoms and one oxygen atom are member atoms of the chain. Member atoms will be substituted up to their normal valence. For example, in pyridine, the five carbon atoms will each be further substituted with a hydrogen or another substituent.

As used herein, the term "subject" is intended to include human and non-human animals. Exemplary human subjects include a human patient having a disorder, e.g., cancer, or a normal subject. The term "non-human animals" includes all vertebrates, e.g., non-mammals (such as chickens, amphibians, reptiles) and mammals, such as non-human primates, domesticated and/or agriculturally useful animals (such as sheep, dogs, cats, cows, pigs, etc.), and rodents (such as mice, rats, hamsters, guinea pigs, etc.).

As used herein, the term "treat" or "treating" a subject having a disorder refers to administering a compound or a composition described herein to the subject, such that at least one symptom of the disorder is cured, healed, alleviated, relieved, altered, remedied, ameliorated, or improved. Treating includes administering an amount effective to alleviate, relieve, alter, remedy, ameliorate, cure, improve or affect the disorder or the symptoms of the disorder. The treatment may inhibit deterioration or worsening of a symptom of a disorder.

Definitions of specific functional groups and chemical terms are described in more detail below. For purposes of this disclosure, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March March's Advanced Organic Chemistry, 5th Edition, John Wiley & Sons, Inc., New York, 2001; Larock, Comprehensive Organic Transformations, VCH Publishers, Inc., New York, 1989; Carruthers, Some Modern Methods of Organic Synthesis, 3rd Edition, Cambridge University Press, Cambridge, 1987; the entire contents of each of which are incorporated herein by reference.

The term "alkyl" refers to a straight or branched saturated hydrocarbon chain. Alkyl groups may include a specified number of carbon atoms. For example, $C_1$-$C_{12}$ alkyl indicates that the alkyl group may have 1, 2, 3, 4, 5, 6, 7, 8, 9, 10, 11 or 12 carbon atoms. An alkyl group may be, e.g., a $C_1$-$C_{12}$ alkyl group, a $C_1$-$C_{10}$ alkyl group, a $C_1$-$C_8$ alkyl group, a $C_1$-$C_6$ alkyl group or a $C_1$-$C_4$ alkyl group. For example, exemplary $C_1$-$C_4$ alkyl groups include methyl, ethyl, n-propyl, isopropyl, n-butyl, sec-butyl, isobutyl and tert-butyl groups. An alkyl group may be optionally substituted with one or more substituents.

The term "alkylenyl" refers to a divalent alkyl group, examples of which include but are not limited to —CH$_2$—, —CH$_2$CH$_2$—, —CH$_2$CH$_2$CH$_2$— and —CH$_2$CH(CH$_3$)CH$_2$—. An alkylenyl group may be optionally substituted with one or more substituents.

The term "alkenyl" refers to a straight or branched hydrocarbon chain having one or more double bonds. Alkenyl groups may include a specified number of carbon atoms. For example, C$_2$-C$_{12}$ alkenyl indicates that the alkenyl group may have 2, 3, 4, 5, 6, 7, 8, 9, 10, 11 or 12 carbon atoms. An alkenyl group may be, e.g., a C$_2$-C$_{12}$ alkenyl group, a C$_2$-C$_{10}$ alkenyl group, a C$_2$-C$_8$ alkenyl group, a C$_2$-C$_6$ alkenyl group or a C$_2$-C$_4$ alkenyl group. Examples of alkenyl groups include but are not limited to allyl, propenyl, 2-butenyl, 3-hexenyl and 3-octenyl groups. One of the double bond carbons may optionally be the point of attachment of the alkenyl substituent. An alkenyl group may be optionally substituted with one or more substituents.

The term "alkenylenyl" refers to a divalent alkenyl group, examples of which include but are not limited to —CH═CH—, —CH═CH—CH$_2$—, —CH═CH—CH$_2$—CH$_2$— and —CH$_2$—CH═CH—CH$_2$—. An alkenylenyl group may be optionally substituted with one or more substituents.

The term "alkynyl" refers to a straight or branched hydrocarbon chain having one or more triple bonds. Alkynyl groups may include a specified number of carbon atoms. For example, C$_2$-C$_{12}$ alkynyl indicates that the alkynyl group may have 2, 3, 4, 5, 6, 7, 8, 9, 10, 11 or 12 carbon atoms. An alkynyl group may be, e.g., a C$_2$-C$_{12}$ alkynyl group, a C$_2$-C$_{10}$ alkynyl group, a C$_2$-C$_8$ alkynyl group, a C$_2$-C$_6$ alkynyl group or a C$_2$-C$_4$ alkynyl group. Examples of alkynyl groups include but are not limited to ethynyl, propargyl, and 3-hexynyl. One of the triple bond carbons may optionally be the point of attachment of the alkynyl substituent. An alkynyl group may be optionally substituted with one or more substituents.

The term "alkynylenyl" refers to a divalent alkynyl group, examples of which include but are not limited to —C≡C—, —C≡C—CH$_2$—, —C≡C—CH$_2$—CH$_2$— and —CH$_2$—C≡C—CH$_2$—. An alkynylenyl group may be optionally substituted with one or more substituents.

The term "amino" as used herein refers to —NR$_{N1}$R$_{N2}$ wherein R$_{N1}$ and R$_{N2}$ independently may be H, alkyl, aryl, alkenyl, alkynyl, heteroalkyl, cycloalkyl, heteroaryl, or heterocyclyl.

The term "aryl" refers to an aromatic monocyclic, bicyclic, or tricyclic hydrocarbon ring system, wherein any ring atom capable of substitution can be substituted (e.g., with one or more substituents). Examples of aryl moieties include but are not limited to phenyl, naphthyl, and anthracenyl. Aryl groups may be optionally substituted with one or more substituents.

The term "arylalkyl" refers to an alkyl moiety in which at least one alkyl hydrogen atom is replaced with an aryl group. Arylalkyl includes groups in which more than one hydrogen atom has been replaced with an aryl group. Examples of arylalkyl groups include but are not limited to benzyl, 2-phenylethyl, 3-phenylpropyl, 9-fluorenyl, benzhydryl, and trityl groups. Arylalkyl groups may be optionally substituted with one or more substituents, on either the aryl moiety or the alkyl moiety.

The term "carbonyl" as used herein refers to a —C(O)R group, wherein R is alkyl, aryl, alkenyl, alkynyl, alkoxy, heteroalkyl, cycloalkyl, heteroaryl, heterocyclyl, or amino. The term "C$_{1-4}$ carbonyl" refers to a group that may be preceded by an alkyl group of up to 3 carbon atoms. It may also be called an "alkylcarbonyl". Examples of C$_{1-4}$ carbonyl include —C(O)R, —CH$_2$C(O)R, —CH$_2$CH$_2$C(O)R, and —CH$_2$CH$_2$CH$_2$C(O)R.

The term "carboxyl" as used herein refers to a —OC(O)R group, wherein R is alkyl, aryl, alkenyl, alkynyl, alkoxy, heteroalkyl, cycloalkyl, heteroaryl, heterocyclyl, or amino. The term "C$_{1-4}$ carboxyl" refers to a group that may be preceded by an alkyl group of up to 3 carbon atoms. It may also be called an "alkylcarboxyl". Examples of C$_{1-4}$ carbonyl include —OC(O)R, —CH$_2$OC(O)R, —CH$_2$CH$_2$OC(O)R, and —CH$_2$CH$_2$CH$_2$OC(O)R.

The term "cycloalkyl" as used herein refers to non-aromatic, saturated or partially unsaturated cyclic, bicyclic, tricyclic or polycyclic hydrocarbon groups having 3 to 12 carbons. Any ring atom can be substituted (e.g., with one or more substituents). Cycloalkyl groups can contain fused rings. Fused rings are rings that share one or more common carbon atoms. Examples of cycloalkyl groups include but are not limited to cyclopropyl, cyclobutyl, cyclopentyl, cyclohexyl, cyclohexenyl, cyclohexadienyl, methylcyclohexyl, adamantyl, norbornyl, norbornenyl, tetrahydronaphthalenyl and dihydroindenyl. Cycloalkyl groups may be optionally substituted with one or more substituents.

The term "cycloalkylalkyl", as used herein, refers to an alkyl group in which at least one hydrogen atom is replaced with a cycloalkyl group. Cycloalkylalkyl groups include those in which more than one hydrogen atom of the alkyl group is replaced with a cycloalkyl group. Examples of cycloalkylalkyl groups include but are not limited to cyclohexylmethyl, cyclopentylmethyl, cyclobutylmethyl and cyclopropylmethyl. Cycloalkylalkyl groups can be optionally substituted with one or more substituents, on either the cycloalkyl moiety or the alkyl moiety.

The term "halo" or "halogen" as used herein refers to any radical of fluorine, chlorine, bromine or iodine.

The term "haloalkyl" as used herein refers to an alkyl group as defined herein, in which one or more hydrogen atoms are replaced with halogen atoms, and includes alkyl moieties in which all hydrogens have been replaced with halogens (e.g., perfluoroalkyl such as CF$_3$).

"Heteroalkyl" refers to an alkyl, alkenyl or alkynyl group as defined herein, wherein at least one carbon atom of the alkyl group is replaced with a heteroatom. Heteroalkyl groups may contain from 1 to 18 non-hydrogen atoms (carbon and heteroatoms) in the chain, or 1 to 12 atoms, or 1 to 6 atoms, or 1 to 4 atoms. Heteroalkyl groups may be straight or branched, and saturated or unsaturated. Unsaturated heteroalkyl groups have one or more double bonds and/or one or more triple bonds. Heteroalkyl groups may be unsubstituted or substituted. Exemplary heteroalkyl groups include but are not limited to alkoxyalkyl (e.g., methoxymethyl), and aminoalkyl (e.g., alkylaminoalkyl and dialkylaminoalkyl). Heteroalkyl groups may be optionally substituted with one or more substituents.

The term "heteralkylenyl" refers to a divalent heteroalkyl group, examples of which include but are not limited to —CH$_2$OCH$_2$—, —CH$_2$NHCH$_2$—, polyethyleneglycol groups (e.g., —(CH$_2$CH$_2$O)$_n$—), polyethyleneimine groups (e.g., —(CH$_2$CH$_2$NH)$_n$—), and the like. A heteroalkylenyl group may be optionally substituted with one or more substituents.

The term "heteroaryl" as used herein refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms independently selected from O, N, S, P and Si (e.g., carbon atoms and 1-3, 1-6, or 1-9 heteroatoms independently selected from O, N, S, P and Si if monocyclic, bicyclic, or tricyclic, respectively). Any ring atom can be substituted (e.g., with one or more substituents). Heteroaryl groups can contain fused rings, which are rings that share one or more common atoms. Examples of heteroaryl groups include but are not limited to radicals of pyridine, pyrimidine, pyrazine, pyridazine, pyrrole, imidazole, pyrazole, oxazole, isoxazole, furan, thiazole, isothiazole, thiophene, quinoline, isoquinoline, quinoxaline, quinazoline, cinnoline, indole, isoindole, indolizine, indazole, benzimidazole, phthalazine, pteridine, carbazole, carboline, phenanthridine, acridine, phenanthroline, phenazine, naphthyridines and purines. Heteroaryl groups may be optionally substituted with one or more substituents.

The term "heteroarylalkyl" refers to an alkyl moiety in which at least one alkyl hydrogen atom is replaced with a heteroaryl group. Heteroarylalkyl includes groups in which more than one hydrogen atom has been replaced with a heteroaryl group. Examples of heteroarylalkyl groups include but are not limited to imidazolylmethyl (e.g., 1H-imidazol-2-ylmethyl and 1H-imidazol-4-ylmethyl), pyridinylmethyl (e.g., pyridin-3-ylmethyl and pyridin-4-ylmethyl), pyrimidinylmethyl (e.g., pyrimidin-5-ylmethyl), furylmethyl (e.g., fur-2-ylmethyl and fur-3-ylmethyl), and thienylmethyl (e.g., thien-2-ylmethyl and thien-3-ylmethyl) groups. Heteroarylalkyl groups may be optionally substituted with one or more substituents, on either the heteroaryl moiety or the alkyl moiety.

The term "heteroatom", as used herein, refers to a non-carbon or hydrogen atom such as a nitrogen, sulfur, oxygen, silicon or phosphorus atom. Groups containing more than one heteroatom may contain different heteroatoms.

The term "heterocyclyl", as used herein, refers to a nonaromatic, saturated or partially unsaturated 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, S, Si and P (e.g., carbon atoms and 1-3, 1-6, or 1-9 heteroatoms of O, N, S, Si and P if monocyclic, bicyclic, or tricyclic, respectively). Any ring atom can be substituted (e.g., with one or more substituents). Heterocyclyl groups can contain fused rings, which are rings that share one or more common atoms. Examples of heterocyclyl groups include but are not limited to radicals of tetrahydrofuran, tetrahydrothiophene, tetrahydropyran, oxetane, piperidine, piperazine, morpholine, pyrroline, pyrimidine, pyrrolidine, indoline, tetrahydropyridine, dihydropyran, thianthrene, pyran, benzopyran, xanthene, phenoxathiin, phenothiazine, furazan, lactones, lactams such as azetidinones and pyrrolidinones, sultams, sultones, and the like. Heterocyclyl groups may be optionally substituted with one or more substituents.

The term "heterocyclylalkyl" refers to an alkyl moiety in which at least one alkyl hydrogen atom is replaced with a heterocyclyl group. Heterocyclylalkyl includes groups in which more than one hydrogen atom has been replaced with a heterocyclyl group. Examples of heterocyclylalkyl groups include but are not limited to oxetanylmethyl, morpholinomethyl, and pyrrolidinylmethyl groups, and the like. Heterocyclylalkyl groups may be optionally substituted with one or more substituents, on either the heterocyclyl moiety or the alkyl moiety.

The term "hydroxy" refers to an —OH radical. The term "alkoxy" refers to an —O-alkyl radical. The term "aryloxy" refers to an —O-aryl radical.

The term "oxo" refers to an oxygen atom, which forms a carbonyl when attached to carbon, an N-oxide when attached to nitrogen, and a sulfoxide or sulfone when attached to sulfur (i.e. =O).

The term "mercapto" or "thiol" refers to an —SH radical. The term "thioalkoxy" or "thioether" refers to an —S-alkyl radical. The term "thioaryloxy" refers to an —S-aryl radical.

The term "substituents" refers to a group "substituted" on an alkyl, alkenyl, alkynyl, cycloalkyl, heterocyclyl, aryl, arylalkyl, heteroaryl or heteroarylalkyl group at any atom of that group. Any atom can be substituted. Suitable substituents include, without limitation: acyl, acylamido, acyloxy, alkoxy, alkyl, alkenyl, alkynyl, amido, amino, carboxy, cyano, ester, halo, hydroxy, imino, nitro, oxo (e.g., C=O), phosphonate, sulfinyl, sulfonyl, sulfonate, sulfonamino, sulfonamido, thioamido, thiol, thioxo (e.g., C=S), and ureido. In embodiments, substituents on a group are independently any one single, or any combination of the aforementioned substituents. In embodiments, a substituent may itself be substituted with any one of the above substituents.

The above substituents may be abbreviated herein. For example, the abbreviations Me, Et, Ph and Bn represent methyl, ethyl, phenyl and benzyl, respectively. A more comprehensive list of standard abbreviations used by organic chemists appears in a table entitled Standard List of Abbreviations of the Journal of Organic Chemistry. The abbreviations contained in said list are hereby incorporated by reference.

When used in the present application, the following abbreviations have the meaning set out below:

HBTU is (2-(1H-benzotriazol-1-yl)-1,1,3,3-tetramethyluronium hexafluorophosphate, also known as hexafluorophosphate benzotriazole tetramethyl uronium;

HOBT is hydroxybenzotriazole;

DMAP is 4-dimethylaminopyridine;

EDC is 1-ethyl-3-(3-dimethylaminopropyl)carbodiimide;

THF is tetrahydrofuran;

MeOH is methanol;

EtOAc is ethyl acetate;

DMSO is dimethyl sulfoxide;

RT is room temperature;

HPLC is high-performance liquid chromatography;

AcOH is acetic acid;

NaOAc is sodium acetate;

TRIS-HCl is a buffer of tris(hydroxymethyl)aminomethane and HCl;

TFA is trifluoroacetic acid;

TLC is thin layer chromatography;

EPA vials are vials that meet the requirements of the U.S. Environmental Protection Agency;

BOC is tert-butoxycarbonyl;

TEA is triethylamine;

Protac is a proteolysis targeting chimera;

COMU is (1-cyano-2-ethoxy-2-oxoethylidenaminooxy) dimethylamino-morpholino-carbenium hexafluorophosphate; and EtOH is ethanol.

For compounds described herein, groups and substituents thereof may be selected in accordance with permitted valence of the atoms and the substituents, and such that the selections and substitutions result in a stable compound, e.g., a compound that does not spontaneously undergo transformation such as by rearrangement, cyclization, elimination, etc.

Where substituent groups are specified by their conventional chemical formulae, written from left to right, they optionally encompass substituents resulting from writing the structure from right to left, e.g., —CH$_2$O— optionally also recites —OCH$_2$—.

In accordance with a convention used in the art, the group:

is used in structural formulae herein to depict the bond that is the point of attachment of the moiety or substituent to the core or backbone structure.

Compounds

In an aspect, the present invention provides a compound according to Formula (I):

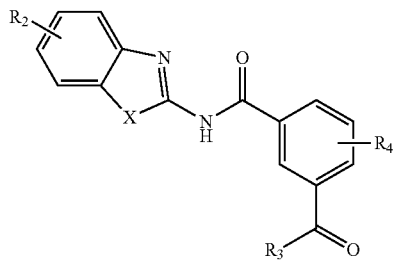

(I)

or a stereoisomer or salt thereof;
wherein X is NR$_1$ or S;
R$_1$ is H, C$_{1-4}$ alkyl, C$_{1-4}$ carbonyl, or C$_{1-4}$ carboxyl;
R$_2$ is H, C$_{1-4}$ alkyl, C$_{1-4}$ alkoxy, or halogen;
R$_3$ is OH, C$_{1-4}$ alkoxy, or amino; and
R$_4$ is H, C$_{1-4}$ alkyl, C$_{1-4}$ alkoxy, or halogen; and
wherein each C$_{1-4}$ alkyl may be independently substituted by halo, hydroxy, or amino.

In an embodiment, the compound of Formula (I) is not

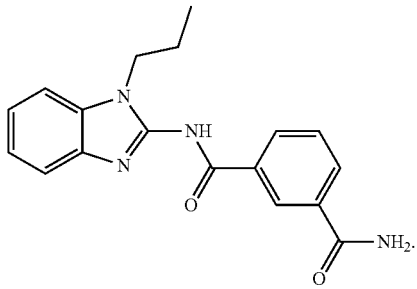

In an embodiment, if X is NR$_1$, R$_1$ is not propyl when R$_3$ is NH$_2$.

In an embodiment, R$_2$ is H, —OCH$_3$, or Br. In an embodiment, R$_3$ is —NH$_2$, —OH, —OCH$_3$, —NHCH$_3$, or —NHCH$_2$CH$_3$. In an embodiment, X is NR$_1$, wherein R$_1$ is H, methyl, or propyl. In an embodiment, X is S.

In an embodiment, the compound may be a compound of Formula (I):

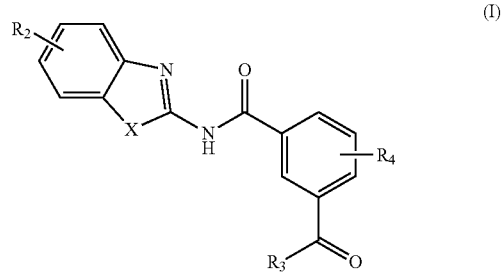

(I)

wherein

| Compound | X | R$_2$ | R$_3$ | R$_4$ |
|---|---|---|---|---|
| 1 | —N(CH$_2$CH$_2$CH$_3$)— | —H | —NH$_2$ | —H |
| 2 | —N(H)— | —H | —NH$_2$ | —H |
| 3 | —N(CH$_3$)— | —H | —NH$_2$ | —H |
| 4 | —N(CH$_2$CH=CHCH$_3$)— | —H | —NH$_2$ | —H |
| 5 | —N(CH$_2$CH(CH$_3$)$_2$)— | —H | —NH$_2$ | —H |
| 6 | —N(CH$_2$CH$_2$OH)— | —H | —NH$_2$ | —H |
| 7 | —N(CH$_2$CO$_2$CH$_3$)— | —H | —NH$_2$ | —H |
| 8 | —N(CH$_2$C(O)Ph)— | —H | —NH$_2$ | —H |
| 9 | —N(CH$_2$CH$_2$N(CH$_3$)$_2$)— | —H | —NH$_2$ | —H |
| 10 | —N(CH$_2$CONH$_2$)— | —H | —NH$_2$ | —H |
| 11 | —S— | —H | —NH$_2$ | —H |
| 12 | —S— | —OCH$_3$ | —NH$_2$ | —H |
| 13 | —S— | —Br | —NH$_2$ | —H |
| 14 | —N(CH$_2$CH$_2$CH$_3$)— | —H | —OH | —H |
| 15 | —N(CH$_2$CH$_2$CH$_3$)— | —H | —OCH$_3$ | —H |
| 16 | —N(CH$_2$CH$_2$CH$_3$)— | —H | —NHCH$_3$ | —H |
| 17 | —N(CH$_2$CH$_2$CH$_3$)— | —H | —NHCH$_2$CH$_3$ | —H |
| 18 | —N(CH$_2$CH$_2$CH$_3$)— | —H | —NHCH$_3$ | —CH$_3$ |
| 19 | —N(CH$_2$CH$_2$CH$_3$)— | —H | —NHCH$_3$ | —OCH$_3$ |
| 20 | —N(CH$_2$CH$_2$CH$_3$)— | —H | —NHCH$_3$ | —Cl |
| 21 | —S— | —H | —OH | —H |
| 22 | —S— | —Br | —OH | —H |
| 23 | —S— | —OCH$_3$ | —OCH$_3$ | —H |

In an embodiment, the compound may be a compound of Formula (I) selected from:

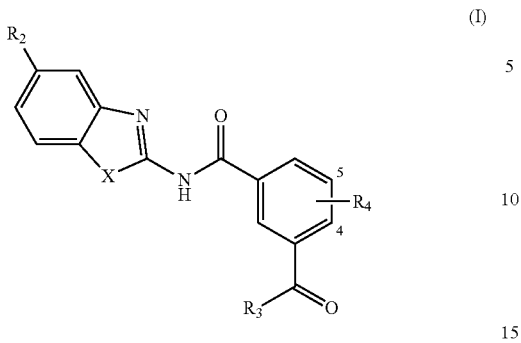

| Compound | X | $R_2$ | $R_3$ | $R_4$ |
|---|---|---|---|---|
| 2 | —N(H)— | —H | —$NH_2$ | —H |
| 3 | —N($CH_3$)— | —H | —$NH_2$ | —H |
| 4 | —N($CH_2$CH=$CHCH_3$)— | —H | —$NH_2$ | —H |
| 5 | —N($CH_2$CH($CH_3$)$_2$)— | —H | —$NH_2$ | —H |
| 6 | —N($CH_2CH_2$OH)— | —H | —$NH_2$ | —H |
| 7 | —N($CH_2CO_2CH_3$)— | —H | —$NH_2$ | —H |
| 8 | —N($CH_2$C(O)Ph)— | —H | —$NH_2$ | —H |
| 9 | —N($CH_2CH_2$N($CH_3$)$_2$)— | —H | —$NH_2$ | —H |
| 10 | —N($CH_2CONH_2$)— | —H | —$NH_2$ | —H |
| 11 | —S— | —H | —$NH_2$ | —H |
| 12 | —S— | —$OCH_3$ | —$NH_2$ | —H |
| 13 | —S— | —Br | —$NH_2$ | —H |
| 14 | —N($CH_2CH_2CH_3$)— | —H | —OH | —H |
| 15 | —N($CH_2CH_2CH_3$)— | —H | —$OCH_3$ | —H |
| 16 | —N($CH_2CH_2CH_3$)— | —H | —$NHCH_3$ | —H |
| 17 | —N($CH_2CH_2CH_3$)— | —H | —$NHCH_2CH_3$ | —H |
| 18 | —N($CH_2CH_2CH_3$)— | —H | —$NHCH_3$ | —$CH_3$ |
| 19 | —N($CH_2CH_2CH_3$)— | —H | —$NHCH_3$ | —$OCH_3$ |
| 20 | —N($CH_2CH_2CH_3$)— | —H | —$NHCH_3$ | —Cl |
| 21 | —S— | —H | —OH | —H |
| 22 | —S— | —Br | —OH | —H |
| 23 | —S— | —$OCH_3$ | —$OCH_3$ | —H |
| 24 | —N($CH_2CH_3$)— | —H | —$OCH_3$ | —H |
| 25 | —N($CH_2CH_3$)— | —H | —$NH_2$ | —H |
| 26 | —N($CH_2CH_3$)— | —H | —OH | —H |
| 27 | —N($CH_2CH_3$)— | —H | —$NHCH_3$ | —H |
| 28 | —N($CH_2(CH_2)_4NH_2$)— | —H | —$OCH_3$ | —H |
| 29 | —N($CH_2CH_2CH_3$)— | —H | —$NH_2$ | 4-Br |
| 30 | —N($CH_2CH_2CH_3$)— | —H | —$NH_2$ | 5-Br | or a tautomer thereof.

In another aspect, the present invention provides compounds according to Formula (II), wherein $R_2$, $R_3$, $R_4$, and X are as defined herein for Formula (II).

In some embodiments, $R_1$ is not -$L_1$-$G_1$ when $R_6$ is C(O)NH-$L_3$-$G_2$ or C(O)NH-$L_4$-$G_3$.

In some embodiments, X is $NR_1$; and $R_1$ is -$L_1$-$G_1$. In some embodiments, X is $NR_1$; $R_1$ is -$L_1$-$G_1$; and $R_2$ is hydrogen. In still further embodiments, and combinations thereof, $R_4$ is hydrogen.

In embodiments described herein $L_1$ is

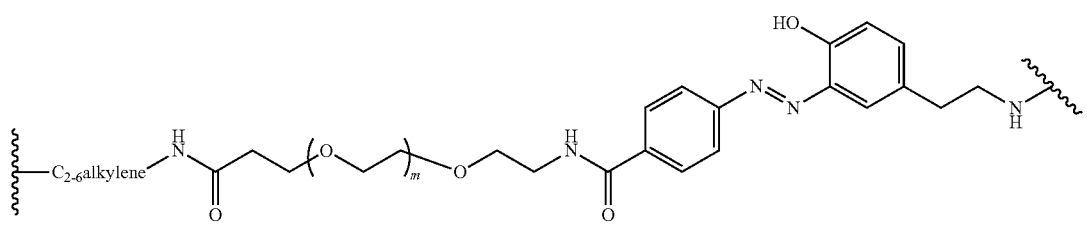

and m is as defined herein. In some embodiments, m is 5 and/or the $C_{2-6}$alkylene is $C_5$alkylene (e.g., n-pentylene).

In some embodiments, $R_2$ is -$L_2$-$R_6$. In some embodiments, $R_2$ is -$L_2$-$R_6$ and $R_6$ is C(O)OH, C(O)O$C_{1-4}$alkyl (e.g., C(O)O$C_2H_5$), C(O)$NH_2$, C(O)NH$C_{1-4}$alkyl, C(O)N($C_{1-4}$alkyl)$_2$, C(O)NH—$C_{2-6}$alkylene-N($C_{1-4}$alkyl)$_2$ (e.g., C(O)NH—$CH_2CH_2$—N($C_{1-4}$alkyl)$_2$), C(O)NH—$C_{2-6}$alkylene-NH($C_{1-4}$alkyl), C(O)NH—$C_{2-6}$alkylene-$NH_2$, C(O)N($C_{1-4}$alkyl)-$C_{2-6}$alkylene-N($C_{1-4}$alkyl)$_2$, C(O)N($C_{1-4}$alkyl)-$C_{2-6}$alkylene-NH($C_{1-4}$alkyl), or C(O)N($C_{1-4}$alkyl)-$C_{2-6}$alkylene-$NH_2$. In some embodiments, $R_2$ is -$L_2$-$R_6$ and $R_6$ is C(O)NH-$L_3$-$G_2$, wherein $L_3$ and $G_2$ are as defined herein.

In the embodiments described herein, $L_3$ is

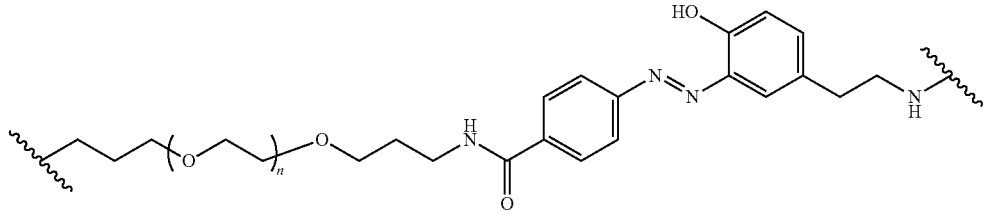

and n is as defined herein. In some embodiments, n is 4.

In some embodiments, $R_2$ is -$L_2$-$R_6$ and $R_6$ is C(O)NH-$L_4$-$G_3$, wherein $L_4$ and $G_3$ are as defined herein.

In the embodiments described herein, $L_4$ is

and n is as defined herein. In some embodiments, n is 4.

In some embodiments, $L_2$ is —CH=CH—

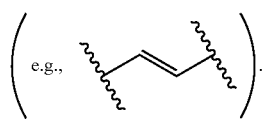

For example, in some embodiments, $R_2$ is -$L_2$-$R_6$; $L_2$ is —CH=CH—; and $R_6$ is C(O)OH, C(O)O$C_{1-4}$alkyl (e.g., C(O)O$C_2H_5$), C(O)$NH_2$, C(O)NH$C_{1-4}$alkyl, C(O)N($C_{1-4}$alkyl)$_2$, C(O)NH—$C_{2-6}$alkylene-N($C_{1-4}$alkyl)$_2$ (e.g., C(O)NH—$CH_2CH_2$—N($C_{1-4}$alkyl)$_2$), C(O)NH—$C_{2-6}$alkylene-NH($C_{1-4}$alkyl), C(O)NH—$C_{2-6}$alkylene-$NH_2$, C(O)N($C_{1-4}$alkyl)-$C_{2-6}$alkylene-N($C_{1-4}$alkyl)$_2$, C(O)N($C_{1-4}$alkyl)-$C_{2-6}$alkylene-NH($C_{1-4}$alkyl), or C(O)N($C_{1-4}$alkyl)-$C_{2-6}$alkylene-$NH_2$. In some embodiments, $R_2$ is -$L_2$-$R_6$; $L_2$ is —CH=CH—; and $R_6$ is C(O)NH-$L_3$-$G_2$. In some embodiments, $R_2$ is -$L_2$-$R_6$; $L_2$ is —CH=CH—; and $R_6$ is C(O)NH-$L_4$-$G_3$. In some embodiments, $R_2$ is -$L_2$-$R_6$; $L_2$ is —CH=CH—; and $R_6$ is C(O)OH, C(O)O$C_{1-4}$alkyl, C(O)NH—$C_{2-6}$alkylene-N($C_{1-4}$alkyl)$_2$, C(O)NH-$L_3$-$G_2$, or C(O)NH-$L_4$-$G_3$.

In some embodiments, X is $NR_1$; and $R_2$ is halogen. In further embodiments, $R_1$ is $C_{1-6}$ alkyl. In still further embodiments, and combinations thereof, $R_4$ is hydrogen.

In some embodiments, X is $NR_1$; and $R_1$ is $C_{1-6}$ alkyl.

In some embodiments, compounds of formula (II) as described in the embodiments herein have formula (II-A)

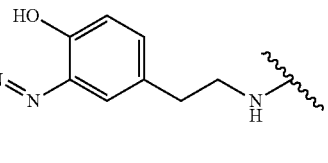

(II-A)

For example, in some embodiments of formula (II-A), $R_2$ is halogen or -$L_2$-$R_6$, and X, $R_3$, $R_4$, $L_2$, and $R_6$ are as defined herein.

In some embodiments, compounds of formula (II) as described in the embodiments herein have formula (II-B)

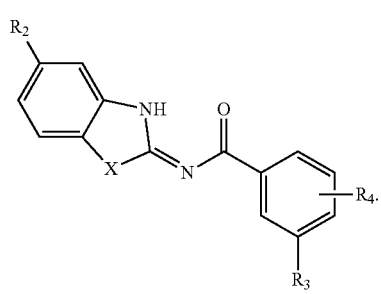

(II-B)

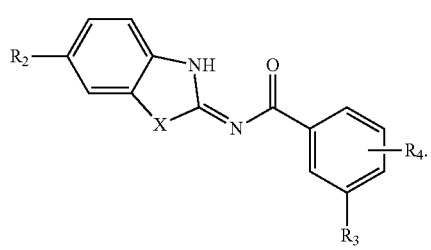

For example, in some embodiments of formula (II-B), $R_2$ is halogen or -$L_2$-$R_6$, and X, $R_3$, $R_4$, $L_2$, and $R_6$ are as defined herein.

In any of the embodiments described herein, $R_4$ may be hydrogen.

In the embodiments wherein $R_3$ is as in formula (II), are further embodiments wherein $R_3$ is C(O)$R_5$. In further embodiments $R_5$ may be $NH_2$.

In the embodiments wherein $R_3$ is as in formula (II), are further embodiments wherein $R_3$ is cyano.

In the embodiments wherein $R_3$ is as in formula (II), are further embodiments wherein $R_3$ is nitro.

In some embodiments, $G_1$ or $G_2$ is an agarose resin, such as Sepharose 4B, a 4% cross-linked spherical particle of size 45-165 m. In general, the agarose resin is suitable for affinity resin chromatography. Agarose-based chromatography resins are described generally by Nweke et al., J. of Chromatography A (2017) 129-137, which is incorporated herein by reference.

In some embodiments, the compound of formula (II) is selected from the group consisting of:

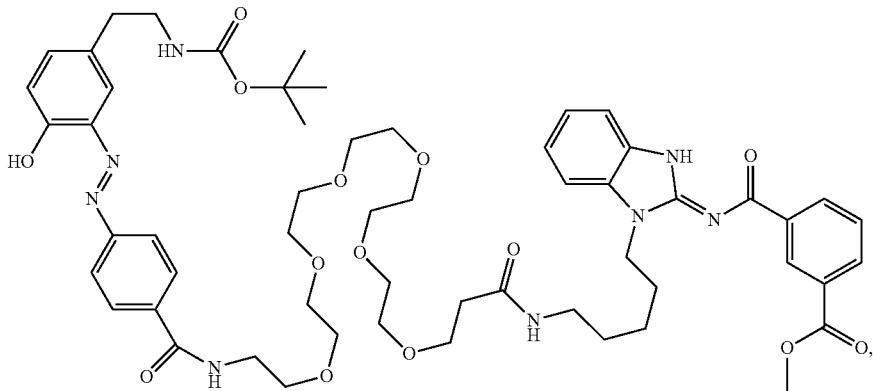

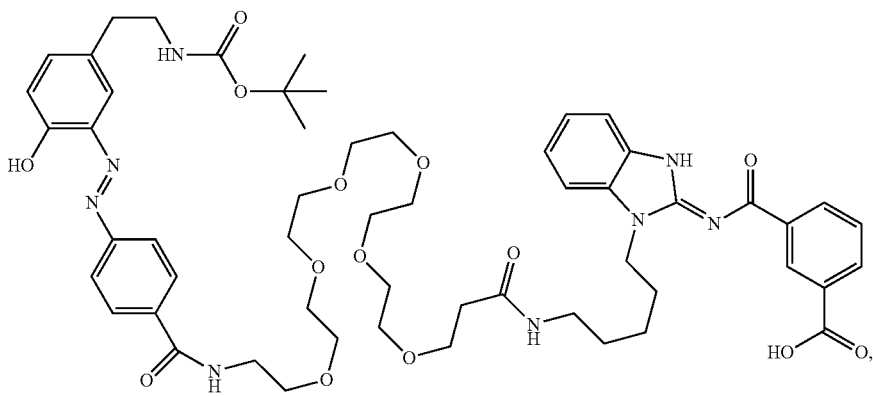

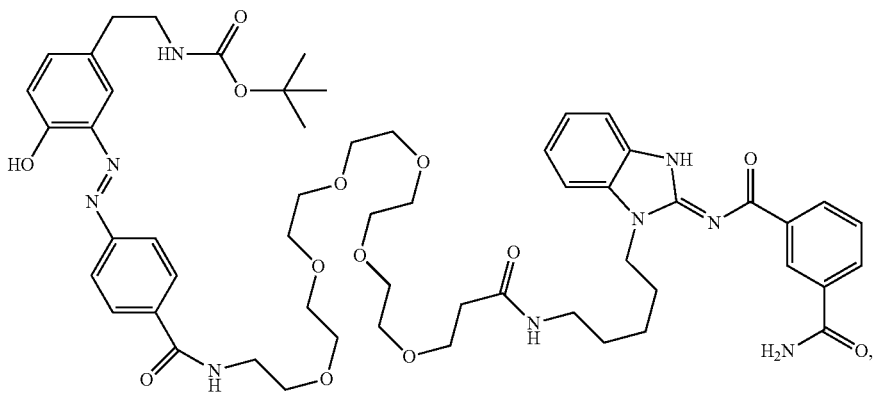

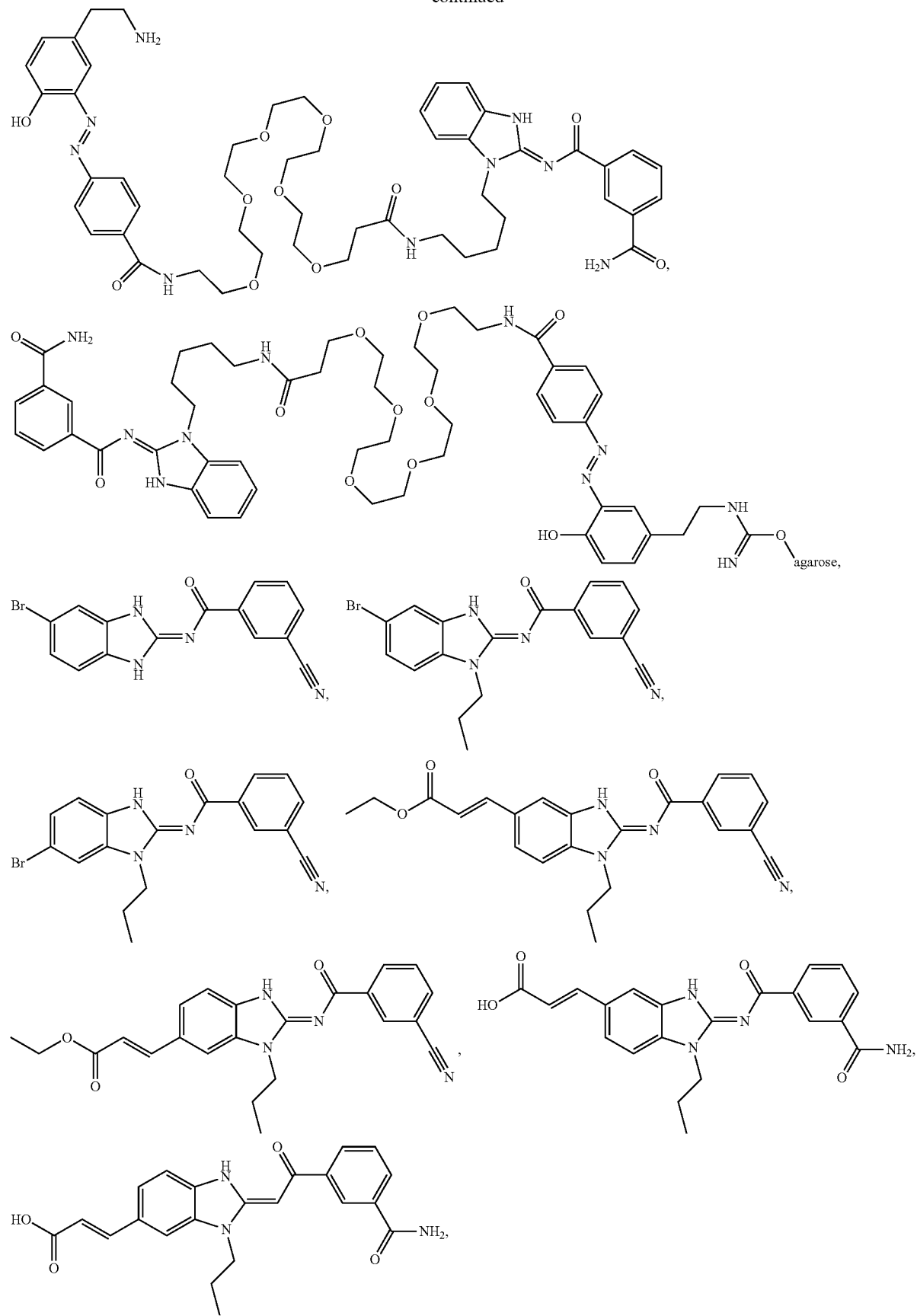

-continued
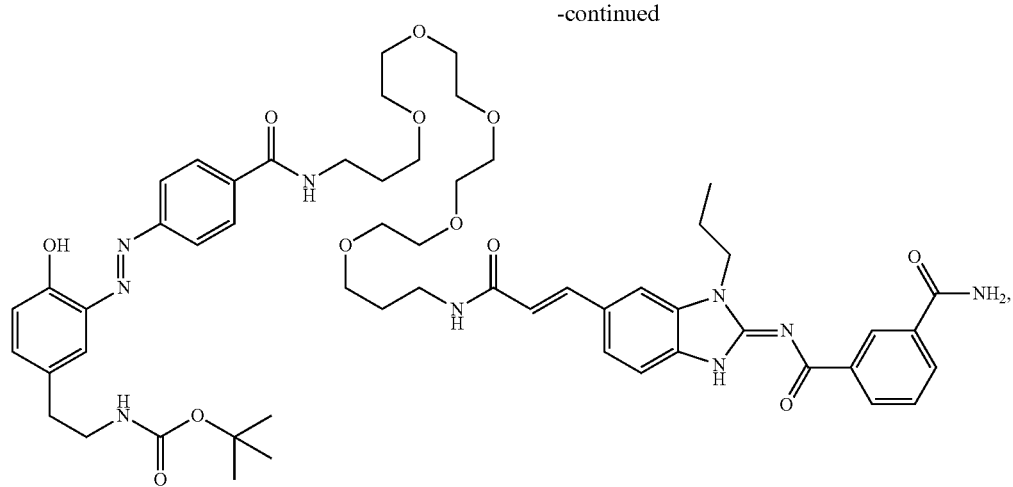
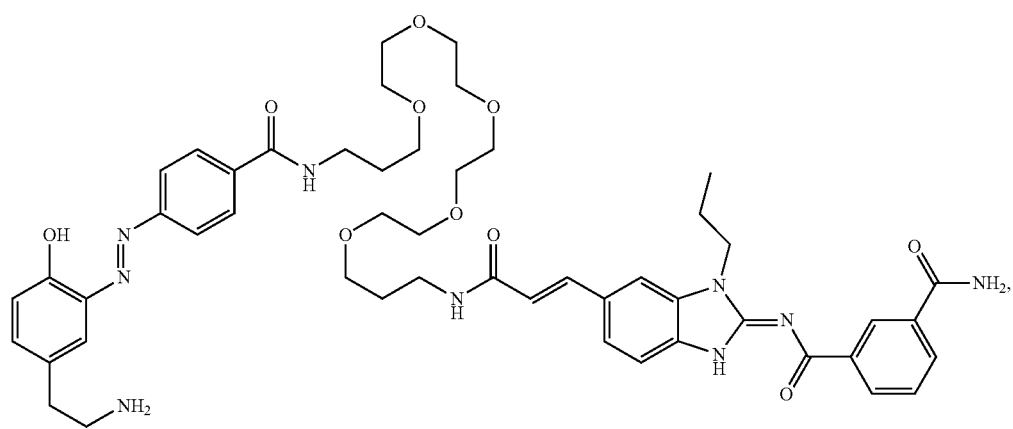
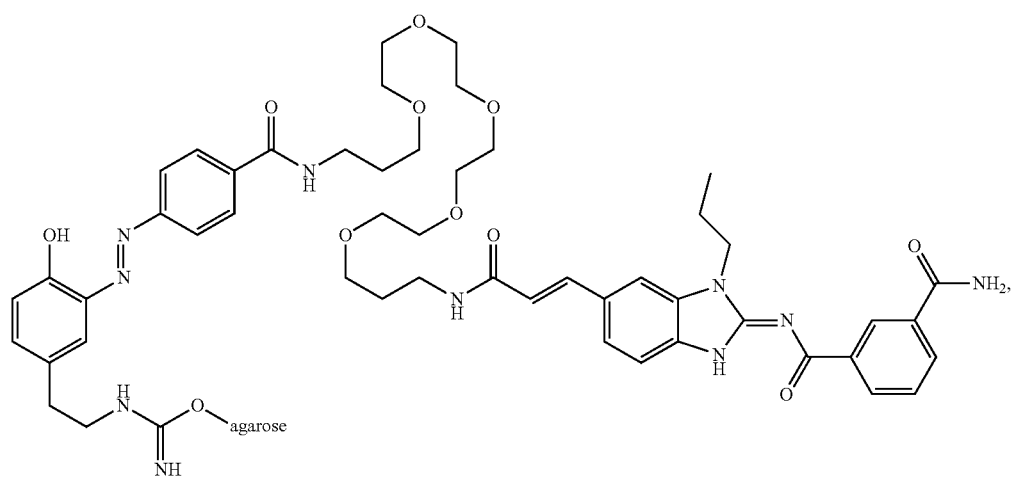

-continued
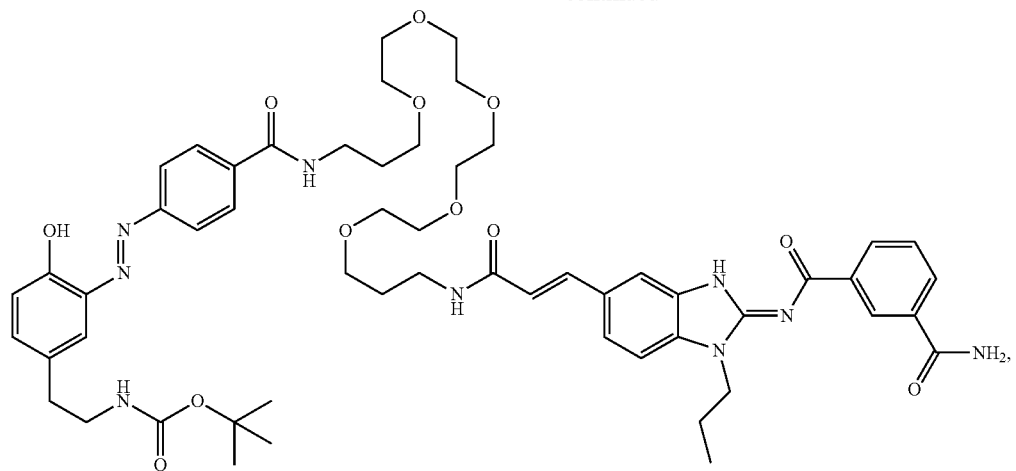
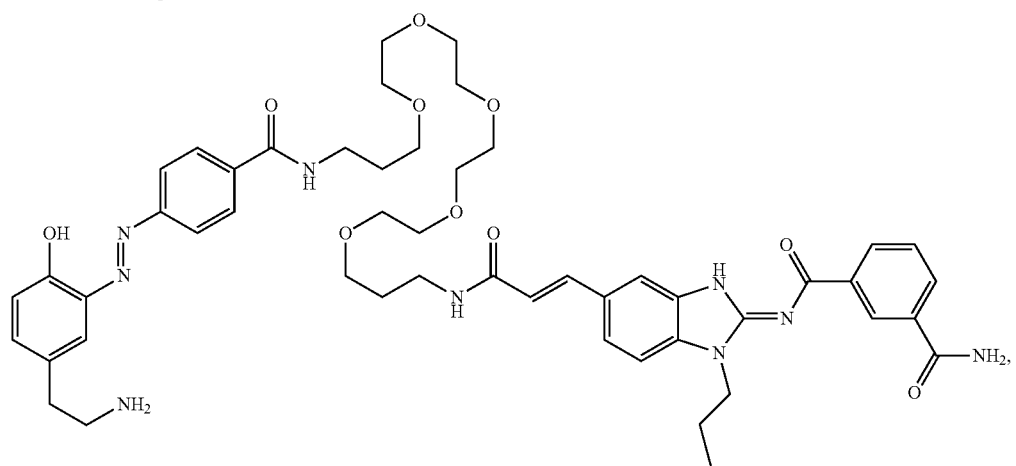
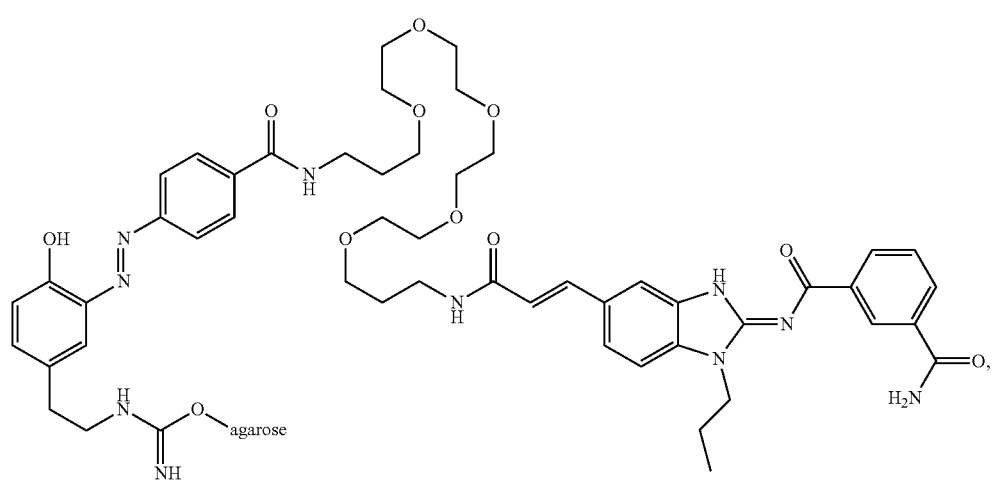
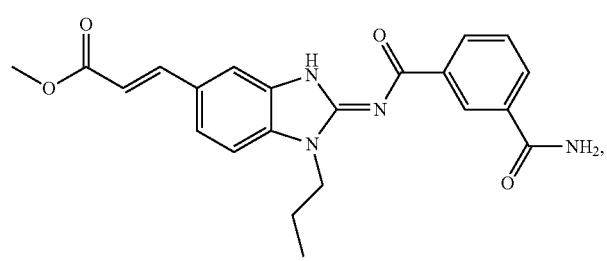

-continued
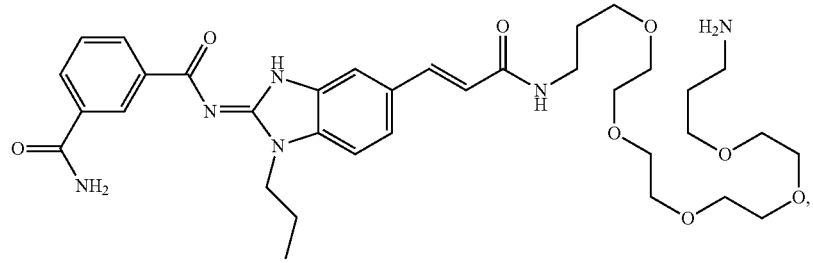
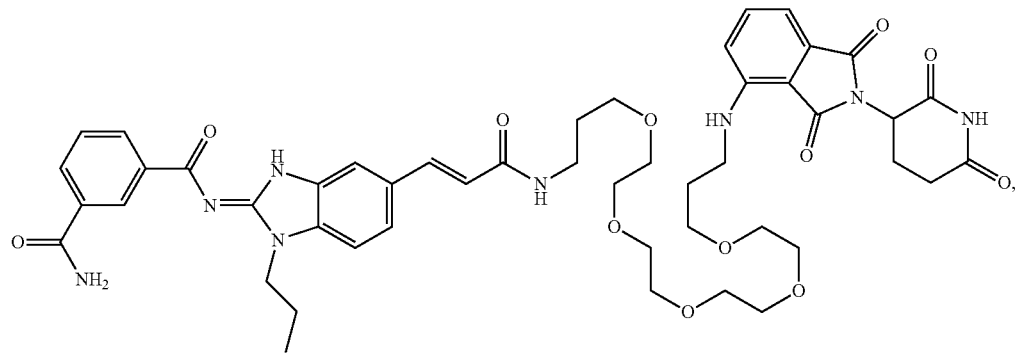
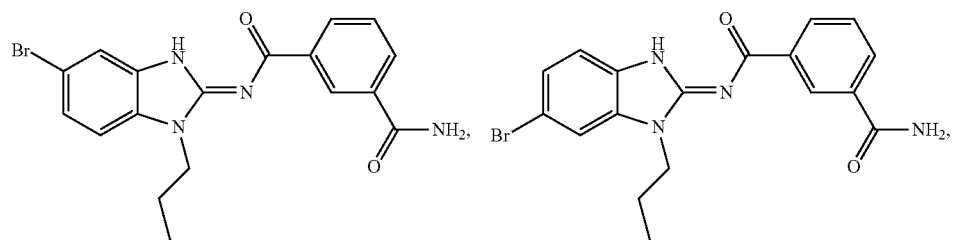
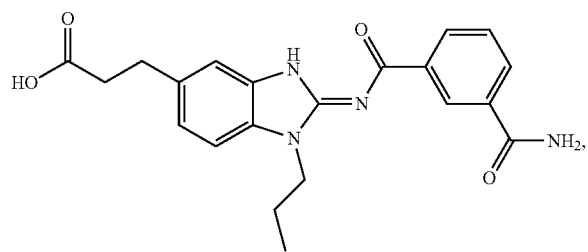
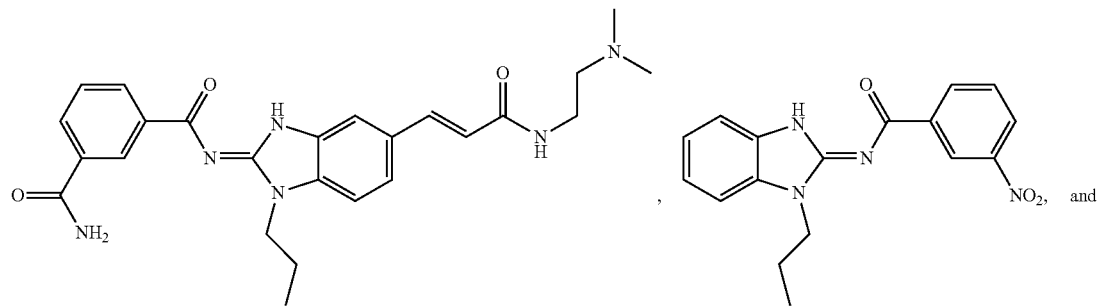

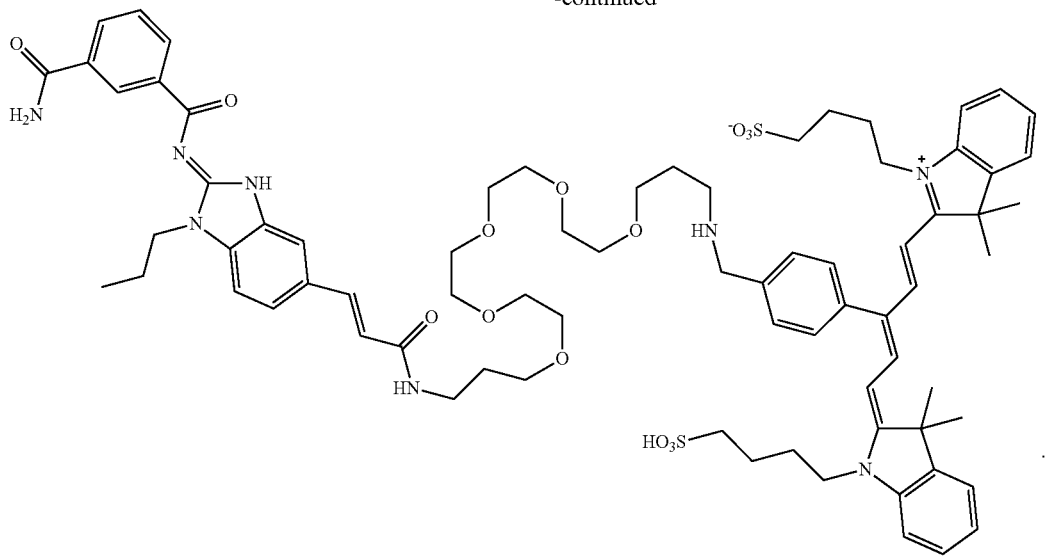

-continued

Certain compounds may exist in one or more particular geometric, optical, enantiomeric, diastereomeric, epimeric, atropic, stereoisomer, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; a- and β-forms; axial and equatorial forms; boat-, chair-, twist-, envelope-, and half chair-forms; and combinations thereof, hereinafter collectively referred to as "isomers" (or "isomeric forms").

In one embodiment, a compound described herein may be an enantiomerically enriched isomer of a stereoisomer described herein. For example, the compound may have an enantiomeric excess of at least about 10%, 15%, 20%, 25%, 30%, 35%, 40%, 45%, 50%, 55%, 60%, 65%, 70%, 75%, 80%, 85%, 90%, 95%, 96%, 97%, 98%, or 99%. Enantiomer, when used herein, refers to either of a pair of chemical compounds whose molecular structures have a mirror-image relationship to each other.

In one embodiment, a preparation of a compound disclosed herein is enriched for an isomer of the compound having a selected stereochemistry, e.g., R or S, corresponding to a selected stereocenter. For example, the compound has a purity corresponding to a compound having a selected stereochemistry of a selected stereocenter of at least about 60%, 65%, 70%, 75%, 80%, 85%, 90%, 95%, 96%, 97%, 98%, or 99%.

In one embodiment, a composition described herein includes a preparation of a compound disclosed herein that is enriched for a structure or structures having a selected stereochemistry, e.g., R or S, at a selected stereocenter. Exemplary R/S configurations can be those provided in an example described herein.

An "enriched preparation," as used herein, is enriched for a selected stereoconfiguration of one, two, three or more selected stereocenters within the subject compound. Exemplary selected stereocenters and exemplary stereoconfigurations thereof can be selected from those provided herein, e.g., in an example described herein. By enriched is meant at least 60%, e.g., of the molecules of compound in the preparation have a selected stereochemistry of a selected stereocenter. In an embodiment it is at least 65%, 70%, 75%, 80%, 85%, 90%, 95%, 96%, 97%, 98%, or 99%. Enriched refers to the level of a subject molecule(s) and does not connote a process limitation unless specified.

Compounds may be prepared in racemic form or as individual enantiomers or diastereomers by either stereo-specific synthesis or by resolution. The compounds may, for example, be resolved into their component enantiomers or diastereomers by standard techniques, such as the formation of stereoisomeric pairs by salt formation with an optically active base, followed by fractional crystallization and regeneration of the free acid. The compounds may also be resolved by formation of stereoisomeric esters or amides, followed by chromatographic separation and removal of the chiral auxiliary. Alternatively, the compounds may be resolved using a chiral HPLC column. The enantiomers also may be obtained from kinetic resolution of the racemate of corresponding esters using lipase enzymes.

Except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g., C$_3$-alkyl or propyl includes n-propyl and iso-propyl; C$_4$-alkyl or butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol, imine/enamine, amide/imino alcohol, amidine/amidine, nitroso/oxime, thioketone/enethiol, N-nitroso/hydroxyazo, and nitro/aci-nitro.

Compounds of Formula (I) include either tautomeric form:

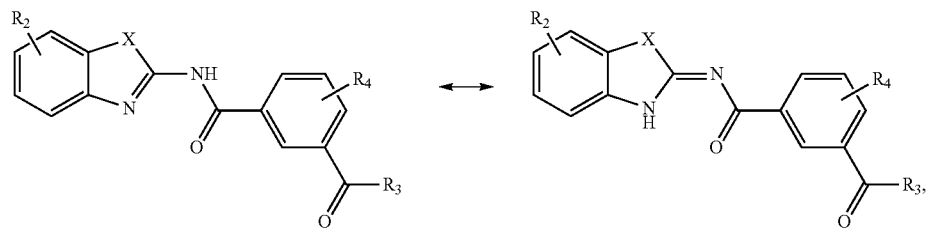

for example

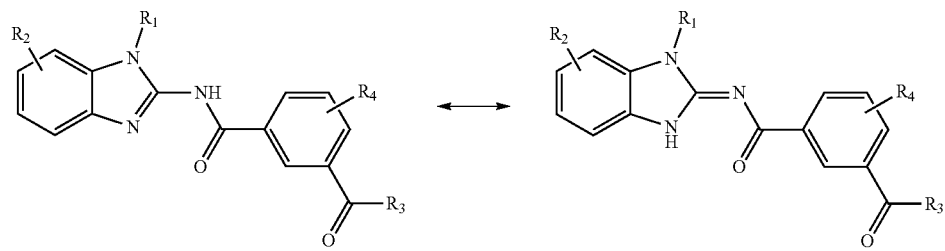

Compounds of Formula (II) include either tautomeric form:

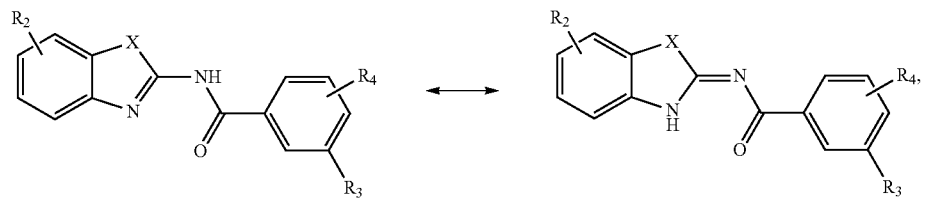

for example

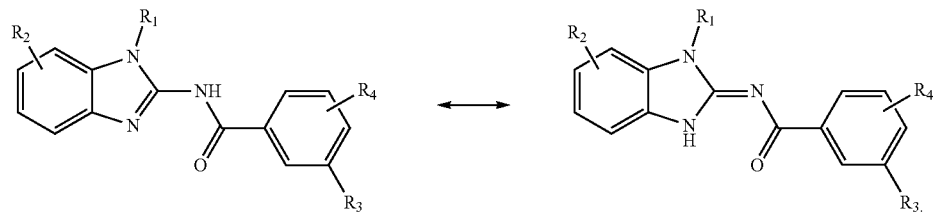

Note that specifically included in the term "isomer" are compounds with one or more isotopic substitutions. Examples of isotopes suitable for inclusion in the compounds of the invention are hydrogen, carbon, nitrogen, oxygen, phosphorus, sulfur, fluorine, and chlorine, such as, but not limited to $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Substitution with heavier isotopes such as deuterium, i.e. $^{2}H$, can afford certain therapeutic advantages resulting from greater metabolic stability, for example, increased in vivo half-life or reduced dosage requirements and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated in compounds of formula (I) or formula (II) are $^{11}C$, $^{13}N$, $^{15}O$, and $^{18}F$. Isotopically-labeled compounds of formula (I) or formula (II) can generally be prepared by conventional techniques known to those skilled in the art or by processes analogous to those described in the accompanying Examples using appropriate isotopically-labeled reagent in place of non-isotopically-labeled reagent. In some embodiments, in compounds of formula (I) or formula (II), any hydrogen atom may be deuterium.

A compound described herein can be in the form of a salt, e.g., a pharmaceutically acceptable salt. The term "pharmaceutically acceptable salt" includes salts of the active compounds that are prepared with relatively nontoxic acids or bases, depending on the particular substituents found on the compounds described herein. Neutral forms of the compounds may be regenerated by contacting the salt with a base or acid and isolating the parent compound in a conventional manner. The parent form of the compound differs from the various salt forms in certain physical properties, such as solubility in polar solvents, but otherwise the salts are equivalent to the parent form of the compound for the purposes of this disclosure. Examples of pharmaceutically acceptable salts are discussed in Berge et al, 1977, "Pharmaceutically Acceptable Salts." J. Pharm. Sci. Vol. 66, pp. 1-19.

For example, if the compound is anionic, or has a functional group which may be anionic (e.g., —COOH may be —COO—), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations. Examples of suitable organic cations include, but are not limited to, ammonium ion (i.e., $NH_4$) and substituted ammonium ions (e.g., $NH_3R_1^+$, $NH_2R_2^+$, $NHR_3^+$, $NR_4+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine.

If the compound is cationic, or has a functional group that may be cationic (e.g., —$NH_2$ may be —$NH_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, gluchep tonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

It may be convenient or desirable to prepare, purify, and/or handle an active compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts; 3rd Edition; John Wiley and Sons, 1999). Unless otherwise specified, a reference to a particular compound also includes chemically protected forms thereof.

A wide variety of such "protecting," "blocking," or "masking" methods are widely used and well known in organic synthesis. For example, a compound which has two nonequivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

A hydroxy group may be protected as an ether (—OR) or an ester (—OC(O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(O)$CH_3$, —OAc).

An aldehyde or ketone group may be protected as an acetal (RCH(OR)$_2$) or ketal ($R_2$C(OR)$_2$), respectively, in which the carbonyl group ($R_2$C=O) is converted to a diether ($R_2$C(OR)$_2$), by reaction with, for example, a primary alcohol. The aldehyde or ketone group is readily regenerated by hydrolysis using a large excess of water in the presence of acid.

An amine group may be protected, for example, as an amide (—NRC(O)R) or a urethane (—NRC(O)OR), for example, as: a methyl amide (—NHC(O)$CH_3$); a benzyloxy amide (—NHC(O)O$CH_2C_6H_5$, —NH-Cbz); as a t-butoxy amide (—NHC(O)OC($CH_3$)$_3$, —NH-Boc); a 2-biphenyl-2-propoxy amide (—NHCO(O)C($CH_3$)$_2C_6H_4C_6H_5$, —NH-Bpoc), as a 9-fluorenylmethoxy amide (—NH-Fmoc), as a 6-nitroveratryloxy amide (—NH—Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH—Psec); or, in suitable cases (e.g., cyclic amines), as a nitroxide radical (>N-0«).

A carboxylic acid group may be protected as an ester, for example, as: an alkyl ester (e.g., a methyl ester; a t-butyl ester); a haloalkyl ester (e.g., a haloalkyl ester); a trialkylsilylalkyl ester; or an arylalkyl ester (e.g., a benzyl ester; a nitrobenzyl ester); or as an amide, for example, as a methyl amide.

A thiol group may be protected as a thioether (—SR), for example, as: a benzyl thioether; an acetamidomethyl ether (—S—$CH_2$NHC(O)$CH_3$)

In addition to salt forms, the present disclosure may also provide compounds that are in a prodrug form. Prodrugs of the compounds described herein are those compounds that readily undergo chemical changes under physiological conditions to provide the compounds described herein. Prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

A compound described herein can also be modified by appending appropriate functionalities to enhance selective biological properties. Such modifications are known in the art and include those that increase biological penetration into a given biological system (e.g., blood, lymphatic system, central nervous system), increase oral availability, increase solubility to allow administration by injection, alter metabolism, and/or alter rate of excretion. Examples of these modifications include, but are not limited to, esterification with polyethylene glycols, derivatization with pivolates or fatty acid substituents, conversion to carbamates, hydroxylation of aromatic rings, and heteroatom substitution in aromatic rings.

a. Synthesis of Compounds

Compounds described herein may be prepared according to a variety of methods. Compounds described herein may be prepared according to a variety of methods. A representative synthesis of exemplary compounds of formula (I) is illustrated in Scheme 1A.

A representative synthesis of exemplary compounds of formula (II) is illustrated in Scheme 1B using standard amide bond forming conditions with an appropriately substituted benzimidazole. This method may generally be used to prepare compounds of formula (II) as further illustrated below.

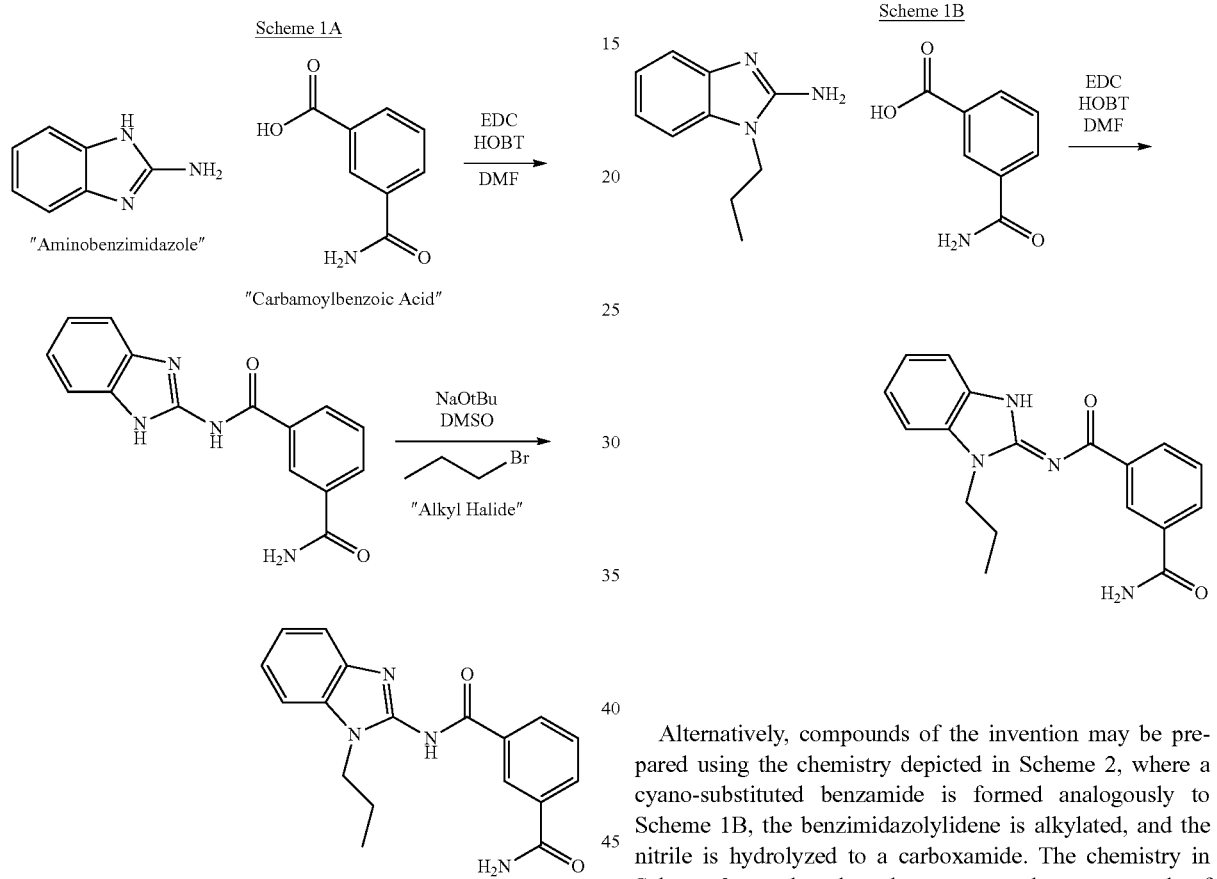

Alternatively, compounds of the invention may be prepared using the chemistry depicted in Scheme 2, where a cyano-substituted benzamide is formed analogously to Scheme 1B, the benzimidazolylidene is alkylated, and the nitrile is hydrolyzed to a carboxamide. The chemistry in Scheme 2 may be adapted to prepare other compounds of formula (II) with variations at $R_2$, $R_3$, and $R_4$.

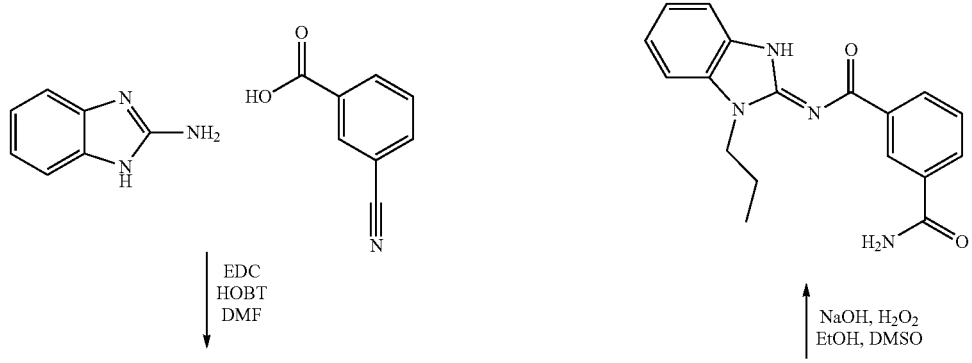

-continued

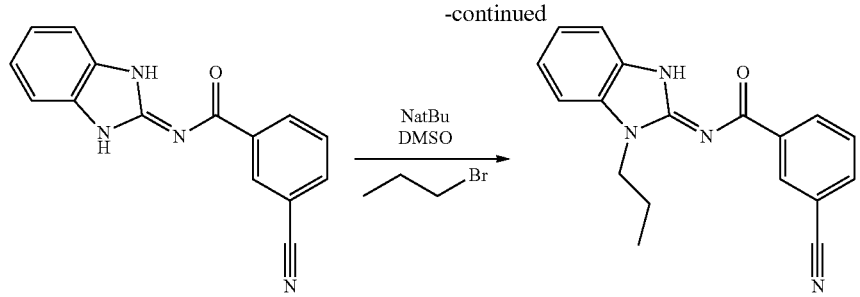

The compounds and intermediates may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry," 5th edition (1989), by Furniss, Hannaford, Smith, and Tatchell, pub. Longman Scientific & Technical, Essex CM20 2JE, England.

A disclosed compound may have at least one basic nitrogen whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, benzenesulfonic, carbonic, fumaric, maleic, gluconic, acetic, propionic, salicylic, hydrochloric, hydrobromic, phosphoric, sulfuric, citric, hydroxybutyric, camphorsulfonic, malic, phenylacetic, aspartic, or glutamic acid, and the like.

Reaction conditions and reaction times for each individual step can vary depending on the particular reactants employed and substituents present in the reactants used. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature. Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in PGM Wuts and TW Greene, in Greene's book titled Protective Groups in Organic Synthesis (4$^{th}$ ed.), John Wiley & Sons, NY (2006), which is incorporated herein by reference in its entirety. Synthesis of the compounds of the invention can be accomplished by methods analogous to those described in the synthetic schemes described hereinabove and in specific examples.

When an optically active form of a disclosed compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it can be obtained by carrying out one of the above procedures using a pure geometric isomer as a starting material, or by resolution of a mixture of the geometric isomers of the compound or intermediates using a standard procedure such as chromatographic separation.

As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P.G.M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents or Organic Synthesis, John Wiley and Sons (1995), and subsequent editions thereof.

b. Evaluation of Compounds

Compounds can be evaluated by determining their ability to inhibit TAK1.

Compounds can be screened for kinase inhibition using a panel of 140 mammalian kinases at the International Center for Kinase Profiling, Dundee. This panel contains members of all major kinase families, including tyrosine kinases (TK), tyrosine kinase-like (TKL), sterile serine/threonine (STE), and CDK/MAPK/GSK/CLK (CMGC). The strongest kinase inhibition was found for TAK1 (STE/TKL family), IRAK4

(TKL), IRAK1 (TKL), CLK2 (CMGC), GCK (STE), and MINK1 (STE), indicating that members of several kinase families were targeted.

Pharmaceutical Compositions

The disclosed compounds may be incorporated into pharmaceutical compositions suitable for administration to a subject (such as a patient, which may be a human or non-human).

In one aspect, provided is a pharmaceutical composition comprising a compound according to Formula (I), or a tautomer or pharmaceutically acceptable salt thereof, and a pharmaceutically acceptable carrier;

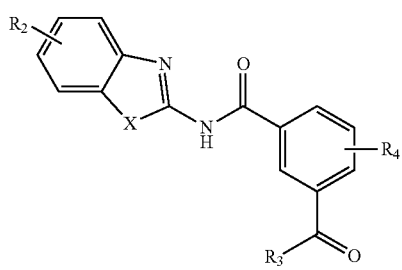

(I)

wherein
X is $NR_1$ or S;
$R_1$ is H, $C_{1-6}$ alkyl, $C_{1-4}$ carbonyl, or $C_{1-4}$ carboxyl;
$R_2$ is H, $C_{1-4}$ alkyl, $C_{1-4}$ alkoxy, or halogen;
$R_3$ is OH, $C_{1-4}$ alkoxy, $NH_2$, $NH(C_{1-4}$ alkyl), or $N(C_{1-4}$ alkyl)($C_{1-4}$ alkyl); and
$R_4$ is H, $C_{1-4}$ alkyl, $C_{1-4}$ alkoxy, or halogen;
wherein the $C_{1-4}$ alkyl and $C_{1-6}$ alkyl of $R_1$, $R_2$, and $R_4$ are optionally independently substituted by halo, hydroxy, $NH_2$, $NH(C_{1-4}$ alkyl), or $N(C_{1-4}$ alkyl)($C_{1-4}$ alkyl).

In one embodiment, the pharmaceutical composition comprises a compound of Formula (I), as described herein, or a tautomer or pharmaceutically acceptable salt thereof. In another embodiment, the pharmaceutical composition comprises

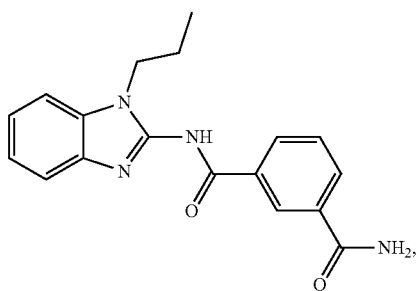 [SMILES: CCCn1c(NC(=O)c2cccc(C(N)=O)c2)nc2ccccc21]

or a tautomer or pharmaceutically acceptable salt thereof.

The pharmaceutical compositions may include a "therapeutically effective amount" or a "prophylactically effective amount" of the agent. A "therapeutically effective amount" refers to an amount effective, at dosages and for periods of time necessary, to achieve the desired therapeutic result. A therapeutically effective amount of the composition may be determined by a person skilled in the art and may vary according to factors such as the disease state, age, sex, and weight of the individual, and the ability of the composition to elicit a desired response in the individual. A therapeutically effective amount is also one in which any toxic or detrimental effects of a compound of the invention (e.g., a compound of formula (I) or (II)) are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

For example, a therapeutically effective amount of a compound of formula (I) or (II), may be about 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg.

The pharmaceutical compositions may include pharmaceutically acceptable carriers. The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Thus, the compounds and their physiologically acceptable salts may be formulated for administration by, for example, solid dosing, eyedrop, in a topical oil-based formulation, injection, inhalation (either through the mouth or the nose), implants, or oral, buccal, parenteral, or rectal administration. Techniques and formulations may generally be found in "Remington's Pharmaceutical Sciences," (Meade Publishing Co., Easton, Pa.). Therapeutic compositions must typically be sterile and stable under the conditions of manufacture and storage.

The route by which the disclosed compounds are administered and the form of the composition will dictate the type of carrier to be used. The composition may be in a variety of forms, suitable, for example, for systemic administration (e.g., oral, rectal, nasal, sublingual, buccal, implants, or parenteral) or topical administration (e.g., dermal, pulmonary, nasal, aural, ocular, liposome delivery systems, or iontophoresis).

Carriers for systemic administration typically include at least one of diluents, lubricants, binders, disintegrants, colorants, flavors, sweeteners, antioxidants, preservatives, glidants, solvents, suspending agents, wetting agents, surfactants, combinations thereof, and others. All carriers are optional in the compositions.

Suitable diluents include sugars such as glucose, lactose, dextrose, and sucrose; diols such as propylene glycol; calcium carbonate; sodium carbonate; sugar alcohols, such as glycerin; mannitol; and sorbitol. The amount of diluent(s) in a systemic or topical composition is typically about 50 to about 90%.

Suitable lubricants include silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of theobroma. The amount of lubricant(s) in a systemic or topical composition is typically about 5 to about 10%.

Suitable binders include polyvinyl pyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of binder(s) in a systemic composition is typically about 5 to about 50%.

Suitable disintegrants include agar, alginic acid and the sodium salt thereof, effervescent mixtures, croscarmelose, crospovidone, sodium carboxymethyl starch, sodium starch glycolate, clays, and ion exchange resins. The amount of disintegrant(s) in a systemic or topical composition is typically about 0.1 to about 10%.

Suitable colorants include a colorant such as an FD&C dye. When used, the amount of colorant in a systemic or topical composition is typically about 0.005 to about 0.1%.

Suitable flavors include menthol, peppermint, and fruit flavors. The amount of flavor(s), when used, in a systemic or topical composition is typically about 0.1 to about 1.0%.

Suitable sweeteners include aspartame and saccharin. The amount of sweetener(s) in a systemic or topical composition is typically about 0.001 to about 1%.

Suitable antioxidants include butylated hydroxyanisole ("BHA"), butylated hydroxytoluene ("BHT"), and vitamin E. The amount of antioxidant(s) in a systemic or topical composition is typically about 0.1 to about 5%.

Suitable preservatives include benzalkonium chloride, methyl paraben and sodium benzoate. The amount of preservative(s) in a systemic or topical composition is typically about 0.01 to about 5%.

Suitable glidants include silicon dioxide. The amount of glidant(s) in a systemic or topical composition is typically about 1 to about 5%.

Suitable solvents include water, isotonic saline, ethyl oleate, glycerine, hydroxylated castor oils, alcohols such as ethanol, and phosphate buffer solutions. The amount of solvent(s) in a systemic or topical composition is typically from about 0 to about 100%.

Suitable suspending agents include AVICEL RC-591 (from FMC Corporation of Philadelphia, Pa.) and sodium alginate. The amount of suspending agent(s) in a systemic or topical composition is typically about 1 to about 8%.

Suitable surfactants include lecithin, Polysorbate 80, and sodium lauryl sulfate, and the TWEENS from Atlas Powder Company of Wilmington, Del. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of surfactant(s) in the systemic or topical composition is typically about 0.1% to about 5%.

Although the amounts of components in the systemic compositions may vary depending on the type of systemic composition prepared, in general, systemic compositions include 0.01% to 50% of an active compound (e.g., a compound of formula (I) or (II)) and 50% to 99.99% of one or more carriers. Compositions for parenteral administration typically include 0.1% to 10% of actives and 90% to 99.9% of a carrier including a diluent and a solvent.

Compositions for oral administration can have various dosage forms. For example, solid forms include tablets, capsules, granules, and bulk powders. These oral dosage forms include a safe and effective amount, usually at least about 5%, and more particularly from about 25% to about 50% of actives. The oral dosage compositions include about 50% to about 95% of carriers, and more particularly, from about 50% to about 75%.

Tablets can be compressed, tablet triturates, enteric-coated, sugar-coated, film-coated, or multiple-compressed. Tablets typically include an active component, and a carrier comprising ingredients selected from diluents, lubricants, binders, disintegrants, colorants, flavors, sweeteners, glidants, and combinations thereof. Specific diluents include calcium carbonate, sodium carbonate, mannitol, lactose and cellulose. Specific binders include starch, gelatin, and sucrose. Specific disintegrants include alginic acid and croscarmelose. Specific lubricants include magnesium stearate, stearic acid, and talc. Specific colorants are the FD&C dyes, which can be added for appearance. Chewable tablets preferably contain sweeteners such as aspartame and saccharin, or flavors such as menthol, peppermint, fruit flavors, or a combination thereof.

Capsules (including implants, time release and sustained release formulations) typically include an active compound (e.g., a compound of formula (I) or (II)), and a carrier including one or more diluents disclosed above in a capsule comprising gelatin. Granules typically comprise a disclosed compound, and preferably glidants such as silicon dioxide to improve flow characteristics. Implants can be of the biodegradable or the non-biodegradable type.

The selection of ingredients in the carrier for oral compositions depends on secondary considerations like taste, cost, and shelf stability, which are not critical for the purposes of this invention.

Solid compositions may be coated by conventional methods, typically with pH or time-dependent coatings, such that a disclosed compound is released in the gastrointestinal tract in the vicinity of the desired application, or at various points and times to extend the desired action. The coatings typically include one or more components selected from the group consisting of cellulose acetate phthalate, polyvinyl acetate phthalate, hydroxypropyl methyl cellulose phthalate, ethyl cellulose, EUDRAGIT® coatings (available from Evonik Industries of Essen, Germany), waxes and shellac.

Compositions for oral administration can have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically include a disclosed compound and a carrier, namely, a carrier selected from diluents, colorants, flavors, sweeteners, preservatives, solvents, suspending agents, and surfactants. Peroral liquid compositions preferably include one or more ingredients selected from colorants, flavors, and sweeteners.

Other compositions useful for attaining systemic delivery of the subject compounds include sublingual, buccal and nasal dosage forms. Such compositions typically include one or more of soluble filler substances such as diluents including sucrose, sorbitol and mannitol; and binders such as acacia, microcrystalline cellulose, carboxymethyl cellulose, and hydroxypropyl methylcellulose. Such compositions may further include lubricants, colorants, flavors, sweeteners, antioxidants, and glidants.

The disclosed compounds can be topically administered. Topical compositions that can be applied locally to the skin may be in any form including solids, solutions, oils, creams, ointments, gels, lotions, shampoos, leave-on and rinse-out hair conditioners, milks, cleansers, moisturizers, sprays, skin patches, and the like. Topical compositions include: a disclosed compound (e.g., a compound of formula (I) of (II)), and a carrier. The carrier of the topical composition preferably aids penetration of the compounds into the skin. The carrier may further include one or more optional components.

The amount of the carrier employed in conjunction with a disclosed compound is sufficient to provide a practical quantity of composition for administration per unit dose of the compound. Techniques and compositions for making dosage forms useful in the methods of this invention are described in the following references: Modern Pharmaceutics, Chapters 9 and 10, Banker & Rhodes, eds. (1979); Lieberman et al., Pharmaceutical Dosage Forms: Tablets (1981); and Ansel, Introduction to Pharmaceutical Dosage Forms, 2nd Ed., (1976).

A carrier may include a single ingredient or a combination of two or more ingredients. In the topical compositions, the carrier includes a topical carrier. Suitable topical carriers include one or more ingredients selected from phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications include propylene glycol, dimethyl isosorbide, and water, and even more particularly, phosphate buffered saline, isotonic water, deionized water, monofunctional alcohols, and symmetrical alcohols.

The carrier of a topical composition may further include one or more ingredients selected from emollients, propellants, solvents, humectants, thickeners, powders, fragrances, pigments, and preservatives, all of which are optional.

Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane. The amount of emollient(s) in a skin-based topical composition is typically about 5% to about 95%.

Suitable propellants include propane, butane, isobutane, dimethyl ether, carbon dioxide, nitrous oxide, and combinations thereof. The amount of propellant(s) in a topical composition is typically about 0% to about 95%.

Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Specific solvents include ethyl alcohol and homotopic alcohols. The amount of solvent(s) in a topical composition is typically about 0% to about 95%.

Suitable humectants include glycerin, sorbitol, sodium 2-pyrrolidone-5-carboxylate, soluble collagen, dibutyl phthalate, gelatin, and combinations thereof. Specific humectants include glycerin. The amount of humectant(s) in a topical composition is typically 0% to 95%.

The amount of thickener(s) in a topical composition is typically about 0% to about 95%.

Suitable powders include beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified Montmorillonite clay, hydrated aluminum silicate, fumed silica, carboxyvinyl polymer, sodium carboxymethyl cellulose, ethylene glycol monostearate, and combinations thereof. The amount of powder(s) in a topical composition is typically 0% to 95%.

The amount of fragrance in a topical composition is typically about 0% to about 0.5%, particularly, about 0.001% to about 0.1%.

Suitable pH adjusting additives include HCl or NaOH in amounts sufficient to adjust the pH of a topical pharmaceutical composition.

It will be appreciated that appropriate dosages of the compounds, and compositions comprising the compounds, can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician. In general, a suitable dose of the compound is in the range of about 100 µg to about 250 mg per kilogram body weight of the subject per day.

The composition may be administered once, on a continuous basis (e.g. by an intravenous drip), or on a periodic/intermittent basis, including about once per hour, about once per two hours, about once per four hours, about once per eight hours, about once per twelve hours, about once per day, about once per two days, about once per three days, about twice per week, about once per week, and about once per month. The composition may be administered until a desired reduction of symptoms is achieved.

Methods of Use

Also disclosed are methods of using the disclosed compounds and compositions to treat or prevent disorders associated with TAK1 activity.

In one aspect, disclosed is a method of inhibiting TAK1, comprising administering to a subject in need thereof a therapeutically effective amount of a compound of formula (I) or (II), or a pharmaceutically acceptable salt thereof.

In another aspect, disclosed is a method of inhibiting tumor growth, comprising administering to a subject in need thereof a therapeutically effective amount of a compound of formula (I) or (II), or a pharmaceutically acceptable salt thereof.

In an aspect, disclosed is a method of treating inflammatory conditions and autoimmune conditions comprising administering to a subject in need thereof a therapeutically effective amount of a compound of formula (I) or (II), or a pharmaceutically acceptable salt thereof.

In an aspect, disclosed is a method of treating rheumatoid arthritis, osteoarthritis, gout, psoriatic arthritis, ankylosing spondylitis, diabetes, Sjogren's syndrome, lupus, inflammatory bowel disease, malaria, Crohn's disease, ulcerative colitis or psoriasis comprising administering to a subject in need thereof a therapeutically effective amount of a compound of formula (I) or (II), or a pharmaceutically acceptable salt thereof.

In another aspect, disclosed is a method of treating or preventing cancer comprising administering to a subject in need thereof a therapeutically effective amount of a compound of formula (I) or (II), or a pharmaceutically acceptable salt thereof. The compounds and compositions described herein can be used to treat a subject having any type of cancer, for example those described by the National Cancer Institute. The cancer can be a carcinoma, a sarcoma, a myeloma, a leukemia, a lymphoma or a mixed type. Exemplary cancers described by the National Cancer Institute include but are not limited to: digestive/gastrointestinal cancers such as anal cancer; bile duct cancer; extrahepatic bile duct cancer; appendix cancer; carcinoid tumor, gastrointestinal cancer; colon cancer; colorectal cancer including childhood colorectal cancer; esophageal cancer including childhood esophageal cancer; gallbladder cancer; gastric (stomach) cancer including childhood gastric (stomach) cancer; hepatocellular (liver) cancer including adult (primary) hepatocellular (liver) cancer and childhood (primary) hepatocellular (liver) cancer; pancreatic cancer including childhood pancreatic cancer; sarcoma, rhabdomyosarcoma; islet cell pancreatic cancer; rectal cancer; and small intestine cancer; endocrine cancers such as islet cell carcinoma (endocrine pancreas); adrenocortical carcinoma including childhood adrenocortical carcinoma; gastrointestinal carcinoid tumor; parathyroid cancer; pheochromocytoma; pituitary tumor; thyroid cancer including childhood thyroid cancer; childhood multiple endocrine neoplasia syndrome; and childhood carcinoid tumor; eye cancers such as intraocular melanoma; and retinoblastoma; musculoskeletal cancers such as Ewing's family of tumors; osteosarcoma/malignant fibrous histiocytoma of the bone; childhood rhabdomyosarcoma; soft tissue sarcoma including adult and childhood soft tissue sarcoma; clear cell sarcoma of tendon sheaths; and uterine sarcoma; breast cancer such as breast cancer including childhood and male breast cancer and breast cancer in pregnancy; neurologic cancers such as childhood brain stemglioma; brain tumor; childhood cerebellar astrocytoma; childhood cerebral astrocytoma/malignant glioma; childhood ependymoma; childhood medulloblastoma; childhood pineal and supratentorial primitive neuroectodermal tumors; childhood visual pathway and hypothalamic glioma; other childhood brain cancers; adrenocortical carcinoma; central nervous system lymphoma, primary; childhood cerebellar astrocytoma; neuroblastoma; craniopharyngioma; spinal cord tumors; central nervous system atypical teratoid/rhabdoid tumor; central nervous system embryonal tumors; and childhood supratentorial primitive neuroectodermal tumors and pituitary tumor; genitourinary cancers such as bladder cancer including childhood bladder cancer; renal cell (kidney) cancer; ovarian cancer including childhood ovarian cancer; ovarian epithelial cancer; ovarian low malignant potential tumor; penile cancer; prostate cancer; renal cell cancer including childhood renal cell cancer; renal pelvis and ureter, transitional cell cancer; testicular cancer; urethral cancer; vaginal cancer; vulvar cancer; cervical cancer; Wilms tumor and other childhood kidney tumors; endometrial cancer; and gestational trophoblastic tumor; Germ cell cancers such as childhood extracranial germ cell tumor; extragonadal germ cell tumor; ovarian germ cell tumor; head and neck cancers such as lip and oral cavity cancer; oral cancer including childhood oral cancer (e.g., oral squamous cell carcinoma); hypopharyngeal cancer; laryngeal cancer including childhood laryngeal cancer; metastatic squamous neck cancer with occult primary; mouth cancer; nasal cavity and paranasal sinus cancer; nasopharyngeal cancer including childhood nasopharyngeal cancer; oropharyngeal cancer; parathyroid cancer; pharyngeal cancer; salivary gland cancer including childhood salivary gland cancer; throat cancer; and thyroid cancer; Hematologic/blood cell cancers such as a leukemia (e.g., acute lymphoblastic leukemia including adult and childhood acute lymphoblastic leukemia; acute myeloid leukemia including adult and childhood acute myeloid leukemia; chronic lymphocytic leukemia such as B Cell chronic lymphocytic leukemia; chronic myelogenous leukemia; and hairy cell leukemia); a lymphoma (e.g., AIDS-related lymphoma; cutaneous T-cell lymphoma; Hodgkin's lymphoma including adult and childhood Hodgkin's lymphoma and Hodgkin's lymphoma during pregnancy; non-Hodgkin's lymphoma including adult and childhood non-Hodgkin's lymphoma and non-Hodgkin's lymphoma during pregnancy; mycosis fungoides; Sezary syndrome; Waldenstrom's macroglobulinemia; primary mediastinal large B cell lymphoma; mantle cell lymphoma; diffuse large B cell lymphoma; and primary central nervous system lymphoma); and other hematologic cancers (e.g., chronic myeloproliferative disorders; multiple myeloma/plasma cell neoplasm; myelodysplastic syndromes; and myelodysplastic/myeloproliferative disorders); lung cancer such as non-small cell lung cancer; and small cell lung cancer; respiratory cancers such as adult malignant mesothelioma; childhood malignant mesothelioma; malignant thymoma; childhood thymoma; thymic carcinoma; bronchial adenomas/carcinoids including childhood bronchial adenomas/carcinoids; pleuropulmonary blastoma; non-small cell lung cancer; and small cell lung cancer; skin cancers such as Kaposi's sarcoma; Merkel cell carcinoma; melanoma; and childhood skin cancer; AIDS-related malignancies; other childhood cancers, unusual cancers of childhood and cancers of unknown primary site; and metastases of the aforementioned cancers can also be treated or prevented in accordance with the methods described herein.

In another aspect, disclosed is a method of treating or preventing breast cancer, colorectal cancer, leukemia, neurofibrodomas, or non-small cell lung cancer or a combination thereof, comprising administering to a subject in need thereof a therapeutically effective amount of a compound of formula (I) or (II), or a pharmaceutically acceptable salt thereof.

Combination Therapies

The present compounds, compositions, and methods may be administered as part of a therapeutic regimen along with other treatments appropriate for the particular injury or disease being treated.

In one aspect, the disclosed compounds can be used in combination with one or more other drugs in the treatment, prevention, control, amelioration, or reduction of risk of diseases or conditions for which disclosed compounds or the other drugs can have utility, where the combination of the drugs together are safer or more effective than either drug alone. Such other drug(s) can be administered, by a route and in an amount commonly used therefor, contemporaneously or sequentially with a compound of the present disclosure. When a compound of the present disclosure is used contemporaneously with one or more other drugs, a pharmaceutical composition in unit dosage form containing such other drugs and a disclosed compound is preferred. However, the combination therapy can also include therapies in which a disclosed compound and one or more other drugs are administered on different overlapping schedules. It is also contemplated that when used in combination with one or more other active ingredients, the disclosed compounds and the other active ingredients can be used in lower doses than when each is used singly.

Accordingly, the pharmaceutical compositions include those that contain one or more other active ingredients, in addition to a compound of the present disclosure.

The above combinations include combinations of a disclosed compound not only with one other active compound, but also with two or more other active compounds. Likewise, disclosed compounds can be used in combination with other drugs that are used in the prevention, treatment, control, amelioration, or reduction of risk of the diseases or conditions for which disclosed compounds are useful. Such other drugs can be administered, by a route and in an amount commonly used therefor, contemporaneously or sequentially with a compound of the present disclosure. When a compound of the present disclosure is used contemporaneously with one or more other drugs, a pharmaceutical composition containing such other drugs in addition to a disclosed compound is preferred. Accordingly, the pharmaceutical compositions include those that also contain one or more other active ingredients, in addition to a compound of the present disclosure.

The weight ratio of a disclosed compound to the second active ingredient can be varied and will depend upon the effective dose of each ingredient. Generally, an effective dose of each will be used. Thus, for example, when a compound of the present disclosure is combined with another agent, the weight ratio of a disclosed compound to the other agent will generally range from about 1000:1 to about 1:1000, preferably about 200:1 to about 1:200. Combinations of a compound of the present disclosure and other active ingredients will generally also be within the aforementioned range, but in each case, an effective dose of each active ingredient should be used.

In such combinations disclosed compounds and other active agents can be administered separately or in conjunction. In addition, the administration of one element can be prior to, concurrent to, or subsequent to the administration of other agent(s).

Accordingly, the disclosed compounds can be used alone or in combination with other agents which are known to be beneficial in the subject indications or other drugs that affect receptors or enzymes that either increase the efficacy, safety, convenience, or reduce unwanted side effects or toxicity of the disclosed compounds. The subject compound and the other agent can be coadministered, either in concomitant therapy or in a fixed combination.

In certain embodiments, the disclosed compounds and compositions can be used in combination with an additional pharmaceutical agent or dosage form. The disclosed compounds and compositions may be administered as part of a regimen additionally including any other pharmaceutical agent and/or pharmaceutical dosage form (e.g., an additional active agent that is effective for the treatment of a cancer, malignancy, or proliferative disorder). An additional pharmaceutically active ingredient or additional pharmaceutical dosage form can be administered to a patient either directly or indirectly, and concomitantly or sequentially, with the compounds and compositions disclosed herein. In certain embodiments, the disclosed compounds and compositions can be used in combination with one or more Hsp90 inhibitors (e.g., 2-(((1r,4r)-4-hydroxycyclohexyl)amino)-4-(3,6,6-trimethyl-4-oxo-4,5,6,7-tetrahydro-1H-indazol-1-yl) benzamide) or one or more Hsp70 inhibitors.

In certain embodiments, the disclosed compounds and compositions can be used in combination with an anti-cancer/chemotherapeutic agent. Exemplary agents include, but are not limited to, alkylating agents (including, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®), bendamustine (Treakisym®, Ribomustin®, Treanda®) chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexylen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), estramustine (Emcyt®, Estracit®), fotemustine, irofulven, mannosulfan, mitobronitol, nimustine, procarbazine, ranimustine, semustine, triaziquone, treosulfan, and Dacarbazine (DTIC-Dome®); anti-EGFR antibodies (e.g., cetuximab (Erbitux®), panitumumab (Vectibix®), and gefitinib (Iressa®)); anti-Her-2 antibodies (e.g., trastuzumab (Herceptin®) and other antibodies from Genentech); antimetabolites (including, without limitation, folic acid antagonists (also referred to herein as antifolates), pyrimidine analogs, purine analogs and adenosine deaminase inhibitors): methotrexate (Rheumatrex®, Trexall®), 5-fluorouracil (Adrucil®, Efudex®, Fluoroplex®), floxuridine (FUDF®), carmofur, cytarabine (Cytosar-U®, Tarabine PFS), 6-mercaptopurine (Puri-Nethol®)), 6-thioguanine (Thioguanine Tabloid®), fludarabine phosphate (Fludara®), pentostatin (Nipent®), pemetrexed (Alimta®), raltitrexed (Tomudex®), cladribine (Leustatin®), clofarabine (Clofarex®, Clolar®), mercaptopurine (Puri-Nethol®), capecitabine (Xeloda®), nelarabine (Arranon®), azacitidine (Vidaza®), decitabine (Dacogen®), enocitabine (Sunrabin®), sapacitabine, tegafur-uracil, tiazofurine, tioguanine, trofosfamide, and gemcitabine (Gemzar®); vinca alkaloids: vinblastine (Velban®, Velsar®), vincristine (Vincasar®, Oncovin®), vindesine (Eldisine®), vinorelbine (Navelbine®), vinflunine (Javlor®); platinum-based agents: carboplatin (Paraplat®, Paraplatin®), cisplatin (Platinol®), oxaliplatin (Eloxatin®), nedaplatin, satraplatin, triplatin; anthracyclines: daunorubicin (Cerubidine®, Rubidomycin®), doxorubicin (Adriamycin®), epirubicin (Ellence®), idarubicin (Idamycin®), mitoxantrone (Novantrone®), valrubicin (Valstar®), aclarubicin, amrubicin, liposomal doxorubicin, liposomal daunorubicin, pirarubicin, pixantrone, zorubicin; topoisomerase inhibitors: topotecan (Hycamtin®), irinotecan (Camptosar®), etoposide (Toposar®, VePesid®), teniposide (Vumon®), lamellarin D, SN-38, camptothecin (e.g., IT-101), belotecan, rubitecan; taxanes: paclitaxel (Taxol®), docetaxel (Taxotere®), larotaxel, cabazitaxel, ortataxel, tesetaxel; antibiotics: actinomycin (Cosmegen®), bleomycin (Blenoxane®), hydroxyurea (Droxia®, Hydrea®), mitomycin (Mitozytrex®, Mutamycin®); immunomodulators: lenalidomide (Revlimid®), thalidomide (Thalomid®); immune cell antibodies: alemtuzamab (Campath®), gemtuzumab (Myelotarg®), rituximab (Rituxan®), tositumomab (Bexxar®); interferons (e.g., IFN-alpha (Alferon®, Roferon-A®, Intron®-A) or IFN-gamma (Actimmune®)); interleukins: IL-1, IL-2 (Proleukin®), IL-24, IL-6 (Sigosix®), IL-12; HSP90 inhibitors (e.g., geldanamycin, 17-alkylamino-17-desmethoxygeldanamycin ("17-AAG") or 17-(2-dimethylaminoethyl)amino-17-desmethoxygeldanamycin ("17-DMAG"); anti-androgens which include, without limitation nilutamide (Nilandron®) and bicalutamide (Caxodex®); antiestrogens which include, without limitation tamoxifen (Nolvadex®), toremifene (Fareston®), letrozole (Femara®), testolactone (Teslac®), anastrozole (Arimidex®), bicalutamide (Casodex®), exemestane (Aromasin®), flutamide (Eulexin®), fulvestrant (Faslodex®), raloxifene (Evista®, Keoxifene®) and raloxifene hydrochloride; anti-hypercalcaemia agents which include without limitation gallium (III) nitrate hydrate (Ganite®) and pamidronate disodium (Aredia®); apoptosis inducers which include without limitation ethanol, 2-[[3-(2,3-dichlorophenoxy)propyl]amino]-(9Cl), gambogic acid, elesclomol, embelin and arsenic trioxide (Trisenox®); Aurora kinase inhibitors which include without limitation binucleine 2; Bruton's tyrosine kinase inhibitors which include without limitation terreic acid; calcineurin inhibitors which include without limitation cypermethrin, deltamethrin, fenvalerate and tyrphostin 8; CaM kinase II inhibitors which include without limitation 5-Isoquinolinesulfonic acid, 4-[{2S)-2-[(5-isoquinolinylsulfonyl)methylamino]-3-oxo-3-{4-phenyl-1-pipe-razinyl)propyl]phenyl ester and benzenesulfonamide; CD45 tyrosine phosphatase inhibitors which include without limitation phosphonic acid; CDC25 phosphatase inhibitors which include without limitation 1,4-naphthalene dione, 2,3-bis[(2-hydroxyethyl)thio]-(9Cl); CHK kinase inhibitors which include without limitation debromohymenialdisine; cyclooxygenase inhibitors which include without limitation 1H-indole-3-acetamide, 1-(4-chlorobenzoyl)-5-methoxy-2-methyl-N-(2-phenylethyl)-(9Cl), 5-alkyl substituted 2-arylaminophenylacetic acid and its derivatives (e.g., celecoxib (Celebrex®), rofecoxib (Vioxx®), etoricoxib (Arcoxia®), lumiracoxib (Prexige®), valdecoxib (Bextra®) or 5-alkyl-2-arylaminophenylacetic acid); cRAF kinase inhibitors which include without limitation 3-(3,5-dibromo-4-hydroxybenzylidene)-5-iodo-1,3-dihydroindol-2-one and benzamide, 3-(dimethylamino)-N-[3-[(4-hydroxybenzoyl)amino]-4-methylphenyl]-(9Cl); cyclin dependent kinase inhibitors which include without limitation olomoucine and its derivatives, purvalanol B, roascovitine (Seliciclib®), indirubin, kenpaullone, purvalanol A and indirubin-3'-monooxime; cysteine protease inhibitors which include without limitation 4-morpholinecarboxamide, N-[(1S)-3-fluoro-2-oxo-1-(2-phenylethyl)propyl]amino]-2-oxo-1-(phenylmeth-yl)ethyl]-(9Cl); DNA intercalators which include without limitation plicamycin (Mithracin®) and daptomycin (Cubicin®); DNA strand breakers which include without limitation bleomycin (Blenoxane®); E3 ligase inhibitors which include without limitation N-((3,3,3-trifluoro-2-trifluoromethyl)propionyl)sulfanilamide; EGF Pathway Inhibitors which include, without limitation tyrphostin 46, EKB-569, erlotinib (Tarceva®), gefitinib (Iressa®), lapatinib (Tykerb®) and those compounds that are generically and specifically disclosed in WO 97/02266, EP 0 564 409, WO 99/03854, EP 0 520 722, EP 0 566 226, EP 0 787 722, EP 0 837 063, U.S. Pat. No. 5,747,498, WO 98/10767, WO 97/30034, WO 97/49688, WO 97/38983 and WO 96/33980; farnesyltransferase inhibitors which include without limitation a-hydroxyfarnesylphosphonic acid, butanoic acid, 2-[(2S)-2-[[(2S,3S)-2-[[(2R)-2-amino-3-mercaptopropyl]amino]-3-methylpent-yl]oxy]-1-oxo-3-phenylpropyl]amino]-4-(methylsulfonyl)-1-methylethylester (2S)-(9Cl), tipifarnib (Zarnestra®), and manumycin A; Flk-1 kinase inhibitors which include without limitation 2-propenamide, 2-cyano-3-[4-hydroxy-3,5-bis(1-methylethyl)phenyl]-N-(3-phenylpropyl)-(2E-)-(9Cl); glycogen synthase kinase-3 (GSK3) inhibitors which include without limitation indirubin-3'-monooxime; histone deacetylase (HDAC) inhibitors which include without limitation suberoylanilide hydroxamic acid (SAHA), [4-(2-amino-phenylcarbamoyl)-benzyl]-carbamic acid pyridine-3-ylmethylester and its derivatives, butyric acid, pyroxamide, trichostatin A, oxamflatin, apicidin, depsipeptide, depudecin, trapoxin, vorinostat (Zolinza®), and compounds disclosed in WO 02/22577; I-kappa B-alpha kinase inhibitors (IKK) which include without limitation 2-propenenitrile, 3-[(4-methylphenyl)sulfonyl]-(2E)-(9Cl); imidazotetrazinones which include without limitation temozolomide (Methazolastone®, Temodar®) and its derivatives (e.g., as disclosed generically and specifically in U.S. Pat. No. 5,260,291) and Mitozolomide; insulin tyrosine kinase inhibitors which include without limitation hydroxyl-2-naphthalenylmethylphosphonic acid; c-Jun-N-terminal kinase (JNK) inhibitors which include without limitation pyrazoleanthrone and epigallocatechin gallate; mitogen-activated protein kinase (MAP) inhibitors which include without limitation benzenesulfonamide, N-[2-[[[3-(4-chlorophenyl)-2-propenyl]methyl]amino]methyl]phenyl]-N-(2-hydroxyethyl)-4-methoxy-(9Cl); MDM2 inhibitors which include without limitation trans-4-iodo, 4'-boranyl-chalcone; MEK inhibitors which include without limitation butanedinitrile, bis[amino[2-aminophenyl)thio]methylene]-(9Cl); MMP inhibitors which include without limitation Actinonin, epigallocatechin gallate, collagen peptidomimetic and non-peptidomimetic inhibitors, tetracycline derivatives marimastat (Marimastat®), prinomastat, incyclinide (Metastat®), shark cartilage extract AE-941 (Neovastat®), Tanomastat, TAA211, MMI270B or AAJ996; mTor inhibitors which include without limitation rapamycin (Rapamune®), and analogs and derivatives thereof, AP23573 (also known as ridaforolimus, deforolimus, or MK-8669), CCI-779 (also known as temsirolimus) (Torisel®) and SDZ-RAD; NGFR tyrosine kinase inhibitors which include without limitation tyrphostin AG 879; p38 MAP kinase inhibitors which include without limitation Phenol, 4-[4-(4-fluorophenyl)-5-(4-pyridinyl)-1H-imidazol-2-yl]-(9Cl), and benzamide, 3-(dimethylamino)-N-[3-[(4-hydroxylbenzoyl)amino]-4-methylphenyl]-(9Cl); p56 tyrosine kinase inhibitors which include without limitation damncanthal and tyrphostin 46; PDGF pathway inhibitors which include without limitation tyrphostin AG 1296, tyrphostin 9, 1,3-butadiene-1,1,3-tricarbonitrile, 2-amino-4-(1H-indol-5-yl)-(9Cl), imatinib (Gleevec®) and gefitinib (Iressa®) and those compounds generically and specifically disclosed in European Patent No.: 0 564 409 and PCT Publication No.: WO 99/03854; phosphatidylinositol 3-kinase inhibitors which include without limitation wortmannin, and quercetin dehydrate; phosphatase inhibitors which include without limitation cantharidic acid, cantharidin, and L-leucinamide; protein phosphatase inhibitors which include without limitation cantharidic acid, cantharidin, L-P-bromotetramisole oxalate, 2(5H)-furanone, 4-hydroxy-5-(hydroxymethyl)-3-(1-oxohexadecyl)-(5R)-(9Cl) and benzylphosphonic acid; PKC inhibitors which include without limitation 1-H-pyrollo-2,5-dione,3-[1-3-(dimethylamino)propyl]-1H-indol-3-yl]-4-(1H-indol-3-yl)-(9Cl), Bis-indolylmaleimide IX, Sphinogosine, staurosporine, and Hypericin; PKC delta kinase inhibitors which include without limitation rottlerin; polyamine synthesis inhibitors which include without limitation DMFO; PTP1B inhibitors which include without limitation L-leucinamide; protein tyrosine kinase inhibitors which include, without limitation tyrphostin Ag 216, tyrphostin Ag 1288, tyrphostin Ag 1295, geldanamycin, genistein and 7H-pyrrolo[2,3-d]pyrimidine derivatives as generically and specifically described in PCT Publication No.: WO 03/013541 and U.S. Publication No.: 2008/0139587; SRC family tyrosine kinase inhibitors which include without limitation PP1 and PP2; Syk tyrosine kinase inhibitors which include without limitation piceatannol; Janus (JAK-2 and/or JAK-3) tyrosine kinase inhibitors which include without limitation tyrphostin AG 490 and 2-naphthyl vinyl ketone; retinoids which include without limitation isotretinoin (Accutane®, Amnesteem®, Cistane®, Claravis®, Sotret®) and tretinoin (Aberel®, Aknoten®, Avita®, Renova®, Retin-A®, Retin-A MICRO®, Vesanoid®); RNA polymerase II elongation inhibitors which include without limitation 5,6-dichloro-1-beta-D-ribofuranosylbenzimidazole; serine/Threonine kinase inhibitors which include without limitation 2-aminopurine; sterol biosynthesis inhibitors which include without limitation squalene epoxidase and CYP2D6; VEGF pathway inhibitors, which include without limitation anti-VEGF antibodies, e.g., bevacizumab, and small molecules, e.g., sunitinib (Sutent®), sorafinib (Nexavar®), ZD6474 (also known as vandetanib) (Zactima™), SU6668, CP-547632 and AZD2171 (also known as cediranib) (Recentin™).

Examples of chemotherapeutic agents are also described in the scientific and patent literature, see, e.g., Bulinski (1997) J. Cell Sci. 110:3055-3064; Panda (1997) Proc. Natl. Acad. Sci. USA 94:10560-10564; Muhlradt (1997) Cancer Res. 57:3344-3346; Nicolaou (1997) Nature 387:268-272; Vasquez (1997) Mol. Biol. Cell. 8:973-985; Panda (1996) J. Biol. Chem. 271:29807-29812.

Other exemplary anti-cancer agents include alitretinon, altretamine, aminopterin, aminolevulinic acid, amsacrine (Amsidine®), asparaginase (crisantaspase, Erwinase®), atrasentan, bexarotene (Targretin®), carboquone, demecolcine, efaproxiral, elsamitrucin, etoglucid, ferrocene, Gliadel implants, hydroxycarbamide, leucovorin, lonidamine, lucanthone, masoprocol, methyl aminolevulinate, mitoguazone, mitotane (Lysodren®), oblimersen, omacetaxine (Genasense®), pegaspargase (Oncaspar®), porfimer sodium (Photofrin®), prednimustine, sitimagene ceradenovec (Cerepro®), talaporfin, temoporfin, trabectedin (Yondelis®), and verteporfin.

Modes of Administration

Dosage levels of the disclosed compounds can range from about 0.001 mg to about 5,000 mg per kilogram body weight. An effective amount of the active agent may range from about 0.001 mg to about 100 mg per kilogram of patient body weight per day. Dosage of active agent can be administered in a single unit or in multiple dosage units to provide the desired therapeutic effect. It will be appreciated that appropriate dosages of the compounds, and compositions comprising the compounds, can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician. In general, a suitable dose of the compound may be in the range of about 100 μg to about 250 mg per kilogram body weight of the subject per day.

The composition may be administered once, on a continuous basis (e.g. by an intravenous drip), or on a periodic/intermittent basis, including about once per hour, about once per two hours, about once per four hours, about once per eight hours, about once per twelve hours, about once per day, about once per two days, about once per three days, about twice per week, about once per week, and about once per month. The composition may be administered until a desired reduction of symptoms is achieved.

Methods of treatment may include any number of modes of administering a disclosed composition. Modes of administration may include tablets, pills, dragees, hard and soft gel capsules, granules, pellets, aqueous, lipid, oily or other solutions, emulsions such as oil-in-water emulsions, liposomes, aqueous or oily suspensions, syrups, elixirs, solid emulsions, solid dispersions or dispersible powders. For the preparation of pharmaceutical compositions for oral administration, the agent may be admixed with commonly known and used adjuvants and excipients such as for example, gum arabic, talcum, starch, sugars (such as, e.g., mannitose, methyl cellulose, lactose), gelatin, surface-active agents, magnesium stearate, aqueous or non-aqueous solvents, paraffin derivatives, cross-linking agents, dispersants, emulsifiers, lubricants, conserving agents, flavoring agents (e.g., ethereal oils), solubility enhancers (e.g., benzyl benzoate or benzyl alcohol) or bioavailability enhancers (e.g. Gelucire™). In the pharmaceutical composition, the agent may also be dispersed in a microparticle, e.g. a nanoparticulate composition.

For parenteral administration, the agent can be dissolved or suspended in a physiologically acceptable diluent, such as, e.g., water, buffer, oils with or without solubilizers, surface-active agents, dispersants or emulsifiers. As oils for example and without limitation, olive oil, peanut oil, cottonseed oil, soybean oil, castor oil and sesame oil may be used. More generally spoken, for parenteral administration, the agent can be in the form of an aqueous, lipid, oily or other kind of solution or suspension or even administered in the form of liposomes or nano-suspensions.

The term "parenterally," as used herein, refers to modes of administration which include intravenous, intramuscular, intraperitoneal, intrasternal, subcutaneous and intraarticular injection and infusion.

Kits

In another aspect, the disclosure provides a kit, which may be used for treating a disease modulated by TAK1 in a subject.

A kit will include a compound of formula (I) or (II) as described herein. A kit may also include instructions for use of the compound of formula (I) or (II) or at least one active agent. Instructions included in kits can be affixed to packaging material or can be included as a package insert. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD, DVD), and the like. As used herein, the term "instructions" can include the address of an internet site that provides the instructions.

In some embodiments, the at least one disclosed compound and the at least one active agent are co-formulated. In some embodiments, the at least one disclosed compound and the at least one active agent are co-packaged. The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

That the disclosed kits can be employed in connection with disclosed methods of use.

The kits may include information, instructions, or both that use of the kit will provide treatment for medical conditions in mammals (particularly humans). The information and instructions may be in the form of words, pictures, or both, and the like. In addition or in the alternative, the kit may include the compound, a composition, or both; and information, instructions, or both, regarding methods of application of compound, or of composition, preferably with the benefit of treating or preventing medical conditions in mammals (e.g., humans).

It will be readily apparent to those skilled in the art that other suitable modifications and adaptations of the compounds and methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples which are merely intended only to illustrate some aspects and embodiments of the disclosure, and should not be viewed as limiting to the scope of the disclosure. The disclosures of all journal references, U.S. patents and publications referred to herein are hereby incorporated by reference in their entireties.

Examples

Example 1. Synthesis of HS-206

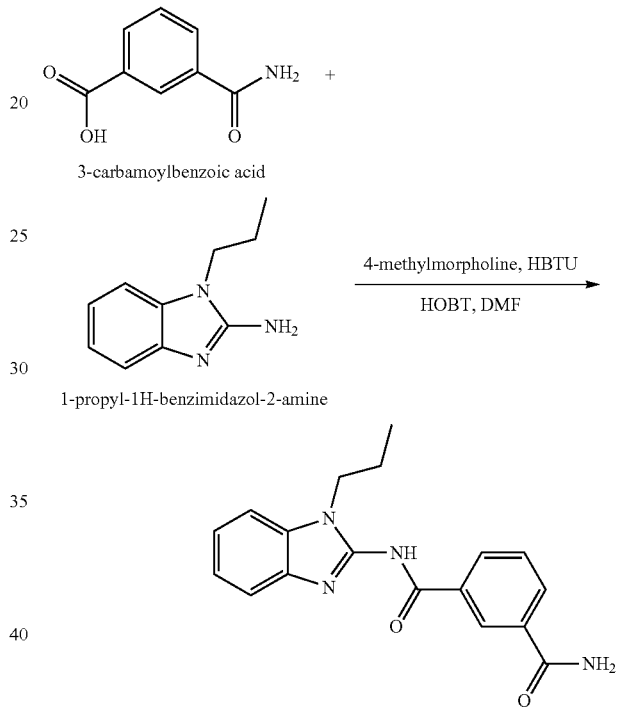

3-Carbamoylbenzoic acid (1 g, 0.006 mol) was dissolved in 10 mL of dry dimethylformamide (DMF) while stirring in a round bottom flask. HBTU (2.73 g, 0.0072 mol)/HOBT hydrate (1.195 g, 0.0078 mol) solution was made with 15 mL DMF. HBTU/HOBT was added to the solution in the round bottom flask. 1-propylbenzimidazol-2-amine (1.157 mg, 0.0066 mol) in 15 mL DMF was injected and the solution was stirred for 20 minutes at room temperature. 4-methylmorpholine (1.98 mL, 0.018 mol) was added to the round bottom flask by syringe. The mixture was stirred until reaction completion (~12 hrs.). The reaction was quenched with 10 mL of deionized (DI) water. A precipitate was formed and isolated by vacuum filtration and washed with 10 mL of DI water to give the final product. Yield 1.56 g (80% yield)

Example 2A

The compounds shown below may be prepared in an analogous manner to that described in Example 1, using appropriate starting materials.

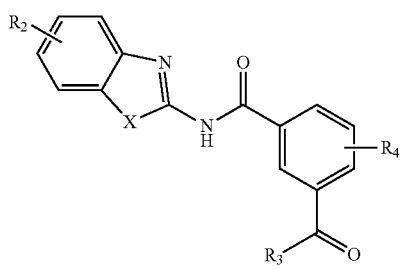

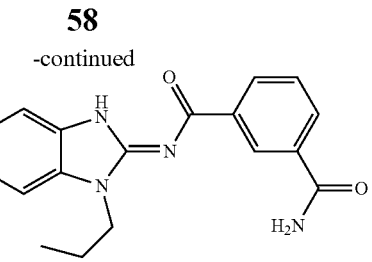

1, EDHS-206 wherein (E)-N-(1-Propyl-1,3-dihydro-2H-benzo[d]imidazol-2-ylidene)isophthalamide 1. A mixture of 3-carbamoylbenzoic

| Compound | X | $R_2$ | $R_3$ | $R_4$ |
|---|---|---|---|---|
| 1 | —N(CH$_2$CH$_2$CH$_3$)— | —H | —NH$_2$ | —H |
| 2 | —N(H)— | —H | —NH$_2$ | —H |
| 3 | —N(CH$_3$)— | —H | —NH$_2$ | —H |
| 4 | —N(CH$_2$CH=CHCH$_3$)— | —H | —NH$_2$ | —H |
| 5 | —N(CH$_2$CH(CH$_3$)$_2$)— | —H | —NH$_2$ | —H |
| 6 | —N(CH$_2$CH$_2$OH)— | —H | —NH$_2$ | —H |
| 7 | —N(CH$_2$CO$_2$CH$_3$)— | —H | —NH$_2$ | —H |
| 8 | —N(CH$_2$C(O)Ph)— | —H | —NH$_2$ | —H |
| 9 | —N(CH$_2$CH$_2$N(CH$_3$)$_2$)— | —H | —NH$_2$ | —H |
| 10 | —N(CH$_2$CONH$_2$)— | —H | —NH$_2$ | —H |
| 11 | —S— | —H | —NH$_2$ | —H |
| 12 | —S— | —OCH$_3$ | —NH$_2$ | —H |
| 13 | —S— | —Br | —NH$_2$ | —H |
| 14 | —N(CH$_2$CH$_2$CH$_3$)— | —H | —OH | —H |
| 15 | —N(CH$_2$CH$_2$CH$_3$)— | —H | —OCH$_3$ | —H |
| 16 | —N(CH$_2$CH$_2$CH$_3$)— | —H | —NHCH$_3$ | —H |
| 17 | —N(CH$_2$CH$_2$CH$_3$)— | —H | —NHCH$_2$CH$_3$ | —H |
| 18 | —N(CH$_2$CH$_2$CH$_3$)— | —H | —NHCH$_3$ | —CH$_3$ |
| 19 | —N(CH$_2$CH$_2$CH$_3$)— | —H | —NHCH$_3$ | —OCH$_3$ |
| 20 | —N(CH$_2$CH$_2$CH$_3$)— | —H | —NHCH$_3$ | —Cl |
| 21 | —S— | —H | —OH | —H |
| 22 | —S— | —Br | —OH | —H |
| 23 | —S— | —OCH$_3$ | —OCH$_3$ | —H |
| 24 | —N(CH$_2$CH$_3$)— | —H | —OCH$_3$ | —H |
| 25 | —N(CH$_2$CH$_3$)— | —H | —NH$_2$ | —H |
| 26 | —N(CH$_2$CH$_3$)— | —H | —OH | —H |
| 27 | —N(CH$_2$CH$_3$)— | —H | —NHCH$_3$ | —H |
| 28 | —N(CH$_2$(CH$_2$)$_4$NH$_2$)— | —H | —OCH$_3$ | —H |
| 29 | —N(CH$_2$CH$_2$CH$_3$)— | —H | —NH$_2$ | 4-Br |
| 30 | —N(CH$_2$CH$_2$CH$_3$)— | —H | —NH$_2$ | 5-Br |

Example 2B. Synthesis of HS-206 Analogs

Synthesis of Takinib and Analogs

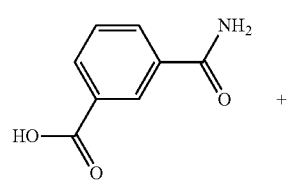

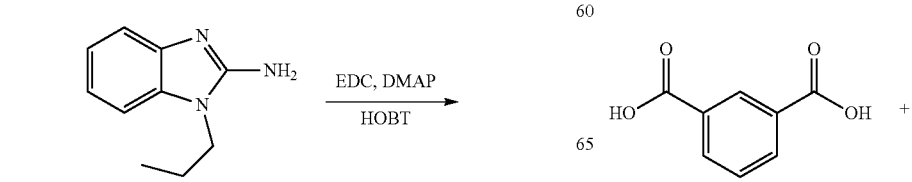

acid (1.5 g, 9.08 mmol), N-propylaminobenzamidazole (1.59 g, 9.08 mmol), HOBT hydrate (1.39 g, 9.08 mmol), DMAP (110 mg, 0.9 mmol) and EDC (2.61 g, 13.6 mmol) were dissolved in methylene chloride (30 mL), treated with Hunig's base (1.17 g, 9.08 mmol) and stirred for 6 days. The reaction mixture was then concentrated and slurried with warm ethanol and water. After stirring for a day, the solid was filtered off, washed with water and air-dried to give compound Takinib/EDHS-206 1 (2.2 g, 75%) as a white powder. LC/MS gave a single peak with m/z=323.1 [M+1]$^+$ and 667.3 [2M+Na]$^+$. $^1$H-NMR (dmso-d$_6$) δ 8.68 (s, 1H), 8.38 (d, J=7 Hz, 1H), 8.10 (s, 1H), 7.98 (d, J=7 Hz, 1H), 7.52-7.57 (m, 3H), 7.41 (s, 1H), 7.26 (t, J=7 Hz, 1H), 7.22 (t, J=7 Hz, 1H), 4.27 (t, J=7 Hz, 2H), 1.85 (h, J=7 Hz, 2H), 0.93 (t, J=7 Hz, 3H).

-continued

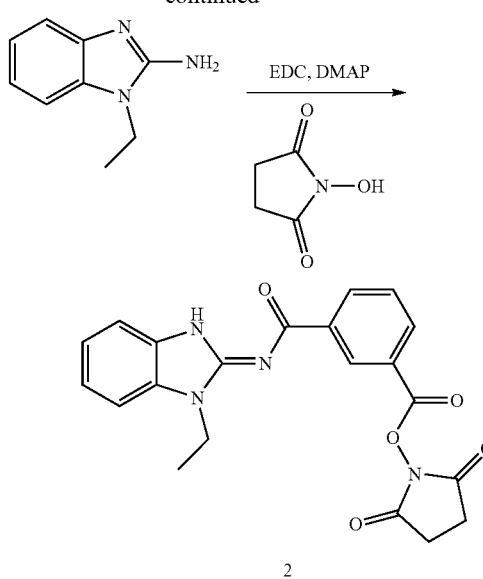

2,5-Dioxopyrrolidin-1-yl (E)-3-((1-ethyl-1,3-dihydro-2H-benzo[d]imidazol-2-ylidene)carbamoyl)benzoate 2. A mixture of isophthalic acid (300 mg, 1.8 mmol), N-ethylaminobenzamidazole (291 mg, 1.8 mmol), N-hydroxysuccinimide (249 mg, 2.17 mmol), DMAP (22 mg, 0.18 mmol) and EDC (865 mg, 4.5 mmol) were dissolved in methylene chloride (5 mL), treated with Hunig's base (233 mg, 1.8 mmol) and stirred for 2 h. The reaction mixture was added to a column and chromatographed (40 g Isco silica gel, 0 to 100% ethyl acetate in hexanes) to give pure product. The product was triturated with 20% ethyl acetate in hexanes to give 2 (157 mg, 21%) as a light cream colored powder. LC/MS gave a single peak with m/z=407.1 [M+1]$^+$ and 835.2 [2M+Na]$^+$. $^1$H-NMR (DMSO-d$_6$) δ 8.88 (s, 1H), 8.67 (d, J=7 Hz, 1H), 8.23 (d, J=7 Hz, 1H), 7.78 (t, J=7 Hz, 1H), 7.57 (d, J=7 Hz, 1H), 7.56 (d, J=7 Hz, 1H), 7.29 (t, J=7 Hz, 1H), 7.25 (t, J=7 Hz, 1H), 4.33 (q, J=7 Hz, 2H), 2.92 (s, 4H), 1.37 (t, J=7 Hz, 3H).

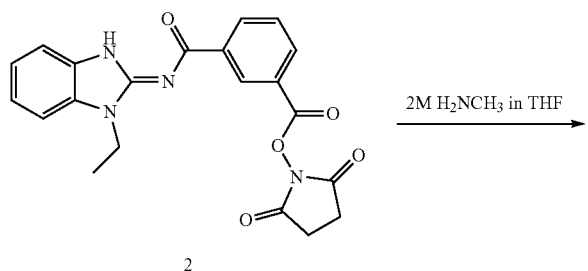

(E)-N$^1$-(1-Ethyl-1,3-dihydro-2H-benzo[d]imidazol-2-ylidene)-N$^3$-methylisophthalamide 3. Compound 2 (20 mg, 49 μmol) was dissolved in methylene chloride (2 mL) and treated with methyl amine (2M in THF, 250 μL). After 4 h, the reaction mixture was concentrated then dissolved in methylene chloride and chromatographed (2×4 g isco silica gel, 0 to 10% MeOH in CH$_2$Cl$_2$) to give the product 3 (11.1 mg, 70%) as a cream colored solid. LC/MS showed a single peak with m/z=323.1 [M+1]$^+$ and 667.2 [2M+Na]$^+$. $^1$H-NMR (dmso-d$_6$) δ 12.73 (br s, 1H), 8.64 (br s, 1H), 8.57 (q, J=4 Hz, 1H), 8.38 (d, J=8 Hz, 1H), 7.94 (d, J=8 Hz, 1H), 7.53-7.58 (m, 3H). 7.27 (dt, J 1, 8 Hz, 1H), 7.23 (dt, J=1, 8 Hz, 1H), 4.34 (q, J=7 Hz, 2H), 2.82 (d, J=4 Hz, 3H), 1.37 (t, J=7 Hz, 3H).

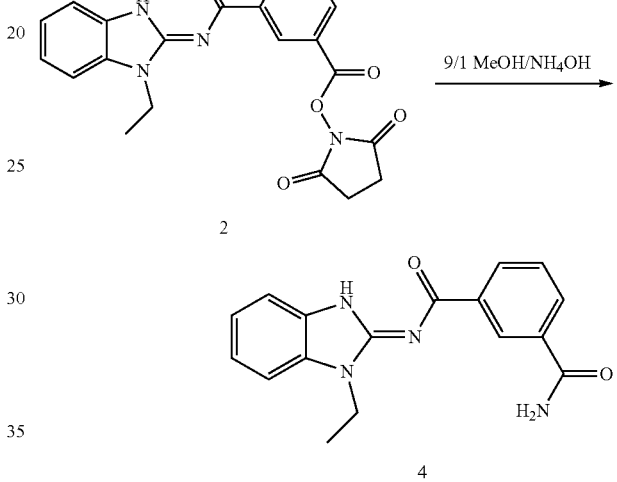

(E)-N-(1-Ethyl-1,3-dihydro-2H-benzo[d]imidazol-2-ylidene)isophthalamide 4. Compound 2 (20 mg, 49 μmol) was dissolved in methylene chloride (2 mL) and treated with 9/1 MeOH/ammonium hydroxide solution (100 μL). After 3 days, the reaction mixture was diluted with methanol, concentrated onto silica gel and chromatographed (2×4 g Isco silica gel, 0 to 10% MeOH in CH$_2$Cl$_2$) to give 4 (12.2 mg) as a white powder. LC/MS showed a single peak with m/z=309.1 [M+1]$^+$ and 639.2 [2M+Na]$^+$. $^1$H-NMR (dmso-d$_6$) δ 12.75 (br s, 1H), 8.68 (br s, 1H), 8.38 (d, J=8 Hz, 1H), 8.10 (s, 1H), 7.98 (d, J=8 Hz, 1H), 7.52-7.57 (m, 3H). 7.27 (dt, J 1, 8 Hz, 1H), 7.42 (s, 1H), 7.23 (dt, J=1, 8 Hz, 1H), 4.34 (q, J=7 Hz, 2H), 1.36 (t, J=7 Hz, 3H).

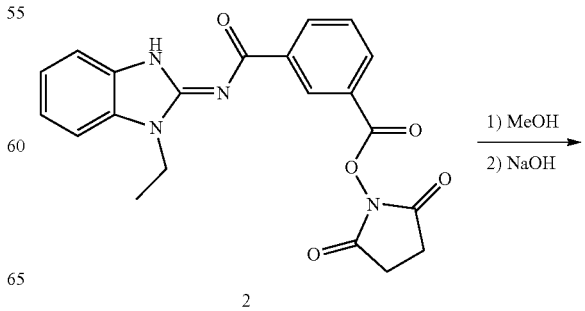

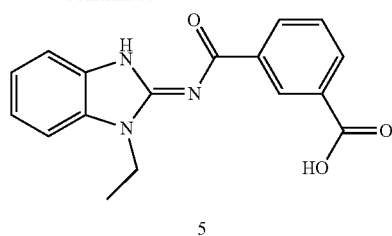

5

(E)-3-((1-Ethyl-1,3-dihydro-2H-benzo[d]imidazol-2-ylidene)carbamoyl)benzoic acid 5. Compound 2 (20 mg, 49 µmol) was dissolved in methanol, treated with 50% sodium hydroxide (10 drops) and stirred for a day. The mixture was then diluted with 1N HCl until a precipitate formed which was eventually filtered off to give 5 (7.7 mg, 48%) as a white solid. LC/MS showed a single peak at m/z=310.1 [M+H]$^+$. $^1$H-NMR (dmso-d$_6$) δ13.09 (v br s, 1H), 12.77 (br s, 1H), 8.78 (br s, 1H), 8.47 (d, J=8 Hz, 1H), 8.07 (d, J=8 Hz, 1H), 7.60 (t, J=8 Hz, 1H), 7.53-7.57 (m, 2H), 7.27 (t, J=8 Hz, 1H), 7.23 (t, J=8 Hz, 1H), 4.32 (q, J=7 Hz, 2H), 1.37 (t, J=7 Hz, 3H).

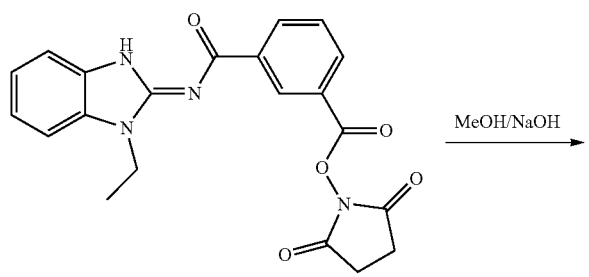

Methyl (E)-3-((1-ethyl-1,3-dihydro-2H-benzo[d]imidazol-2-ylidene)carbamoyl)benzoate 6. Compound 2 (20 mg, 49 µmol) was dissolved in methanol (2 mL) and treated with 1 drop of 50% NaOH (50 mg or 25 mg NaOH). After 3 d, the mixture was treated with acetic acid, concentrated and chromatographed (4 gm isco silica gel, 19/1:CH$_2$Cl$_2$/MeOH) to give a partially purified product. It was triturated with 20% EtOAc in hexane to give a powder and reconcentrated to give 6 (7.1 mg, 50%) as a pinkish solid. LC/MS gave a single peak with m/z=324.1 [M+1]$^+$ and 669.2 [2M+Na]+. $^1$H-NMR (dmso-d$_6$) δ 12.77 (br s, 1H), 8.80 (br s, 1H), 8.51 (d, J=8 Hz, 1H), 8.10 (d, J=8 Hz, 1H), 7.64 (t, J=8 Hz, 1H), 7.54-7.58 (m, 2H), 7.28 (t, J=8 Hz, 1H), 7.24 (t, J=8 Hz, 1H), 4.33 (q, J=7 Hz, 2H), 3.91 (s, 3H), 1.37 (t, J=7 Hz, 3H).

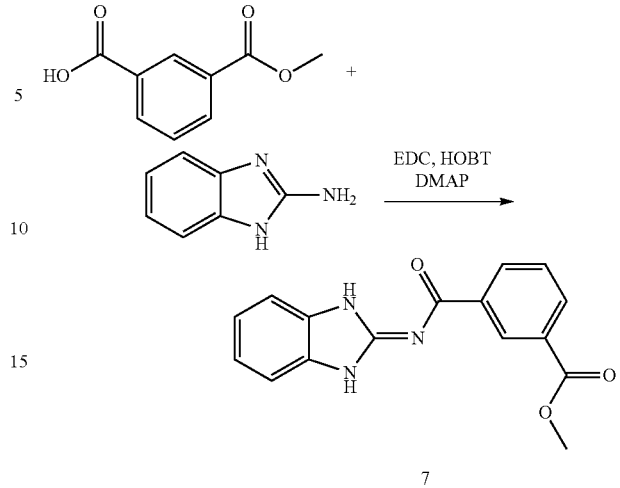

Methyl 3-((1,3-dihydro-2H-benzo[d]imidazol-2-ylidene)carbamoyl)benzoate 7. A mixture of methyl isophthalate (500 mg, 2.8 mmol), aminobenzamidazole (369 mg, 2.8 mmol), HOBT (340 mg, 2.2 mmol), DMAP (34 mg, 0.28 mmol) and EDC (718 mg, 3.7 mmol) were dissolved in methylene chloride (5 mL), treated with Hunig's base (359 mg, 2.8 mmol) and stirred for 1 d. The reaction mixture was diluted with methanol, adsorbed onto silica gel and chromatographed (40 g Isco silica gel, 0 to 10% MeOH in CH$_2$Cl$_2$) to give pure product. The product was triturated with 20% ethyl acetate in hexanes to give 7 (352 mg, 42%) as a white powder. LC/MS gave a single peak with m/z=296.1 [M+1]$^+$. $^1$H-NMR (dmso-d$_6$) δ 12.51 (br s, 1H), 8.78 (br s, 1H), 8.39 (d, J=8 Hz, 1H), 8.13 (d, J=8 Hz, 1H), 7.66 (t, J=8 Hz, 1H), 7.42-7.46 (m, 2H), 7.15-7.19 (m, 2H), 3.91 (s, 3H).

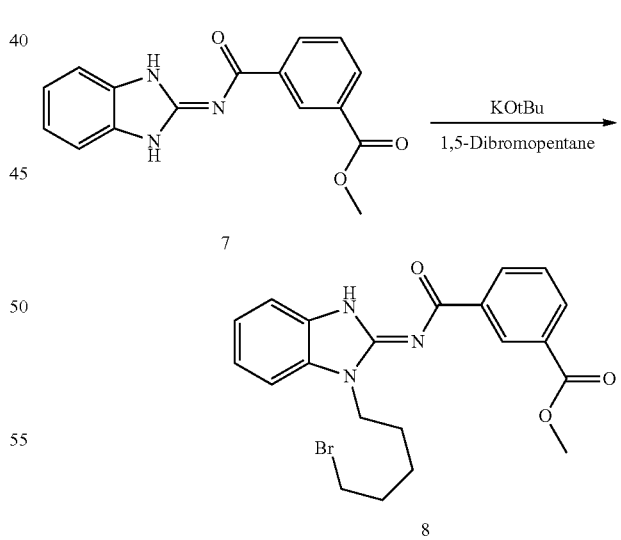

Methyl (E)-3-((1-(5-bromopentyl)-1,3-dihydro-2H-benzo[d]imidazol-2-ylidene)carbamoyl)benzoate 8. Compound 7 (100 mg, 338 µmol) was dissolved in THF (2 mL) and DMSO (1 mL) and treated with KOtBu (338 µL of 1M solution in THF) followed by 1,5-dibromopentane (77.9 mg, 46.1 µL, 338 µmol) and stirred at RT for 2 h. The reaction mixture was concentrated then chromatographed (43 g Isco C18, 0 to 100% MeOH w/0.2% formic in both) to give compound 8 (98 mg, 65%) as a white solid. LC/MS showed a single peak at m/z=444.1 [M+H]$^+$. $^1$H-NMR (DMSO-d$_6$) δ12.77 (br s, 1H), 8.81 (s, 1H), 8.49 (d, J=8 Hz, 1H), 8.09 (d, J=8 Hz, 1H), 7.63 (t, J=8 Hz, 1H), 7.56 (2 d, J=8 Hz, 2H), 7.27 (t, J=8 Hz, 1H), 7.24 (t, J+8 Hz, 1H), 4.30 (t, J=7 Hz, 2H), 3.90 (s, 3H), 3.50 (t, J=7 Hz, 2H), 1.91 (p, J=7 Hz, 2H), 1.87 (p, J=7 Hz, 2H), 1.49 (p, J=7 Hz, 2H).

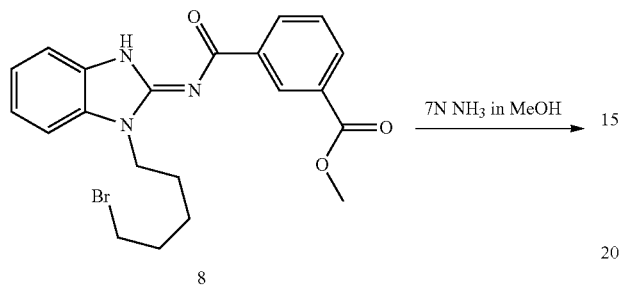

8

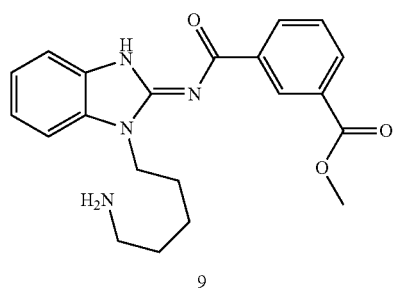

9

Methyl (E)-3-((1-(5-aminopentyl)-1,3-dihydro-2H-benzo[d]imidazol-2-ylidene)carbamoyl)benzoate 9. Compound 8 (67 mg, 151 μmol) was dissolved in methanolic ammonia (7N ammonia in methanol, 4 mL) and heated at 45° C. overnight. The next day, the reaction mixture was concentrated to a glass and chromatographed (43 g Isco C18, 0 to 100% MeOH with 0.2% formic acid) to give compound 9 (33 mg, 60%) as a tacky solid. LC/MS showed a single peak at m/z=381.2. $^1$H-NMR (dmso-d$_6$) δ 8.81 (br s, 1H), 8.49 (d, J=8 Hz, 1H), 8.44 (s, 1H), 8.09 (d, J=8 Hz, 1H), 7.64 (t, J=8 Hz, 1H), 7.53-7.57 (m, 2H), 7.27 (t, j=8 Hz, 1H), 7.23 (t, J=8 Hz, 1H), 4.28 (t, J=7 Hz, 2H), 3.91 (s, 3H), 2.68 (t, J=7 Hz, 2H), 1.84 (p, J=7 Hz, 2H), 1.58 (p, J=7 Hz, 2H), 1.41 (p, J=7 Hz, 2H),

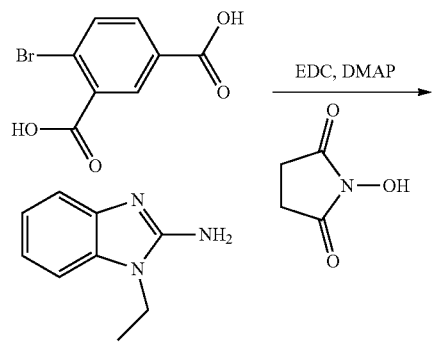

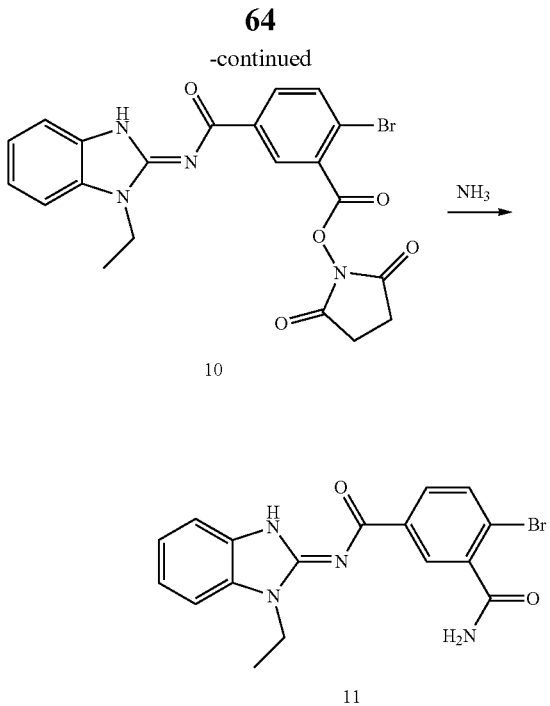

10

11

(E)-4-Bromo-N$^1$-(1-ethyl-1,3-dihydro-2H-benzo[d]imidazol-2-ylidene)isophthalamide 11. A mixture of 4-bromoisophthalic acid (100 mg, 4.1 μmol), N-ethylaminobenzamidazole (66 mg, 4.1 μmol), N-hydroxysuccinimide (56 mg, 4.9 μmol), DMAP (5 mg, 0.4 μmol) and EDC (234 mg, 1.2 mmol) were dissolved in methylene chloride (5 mL), treated with Hunig's base (53 mg, 4.1 μmol) and stirred for 3 d. The reaction mixture was added directly to a column and air-dried for a few minutes then chromatographed (12 g isco silica gel, 0 to 100% EtOAc in hexanes) to give 10 (56 mg, 28%) as a glass. The glass was treated with 7N ammonia in methanol (2 mL) and stirred for 1 d. The mixture was concentrated and chromatographed (12 g isco silica gel, 0 to 10% MeOH in CH$_2$Cl$_2$) to give two peaks. The larger later eluting peak was concentrated to give 11 (19.8 mg, 10%) as a white solid. LC/MS gave a single peak with m/z=387.1 [M+1]$^+$ and 795.0 [2M+Na]+. $^1$H-NMR (dmso-d$_6$) δ 12.77 (br s, 1H), 8.12 (br s, 1H), 7.78 (d, J=8 Hz, 1H), 7.73 (d, J=8 Hz, 1H), 7.54-7.59 (m, 2H), 7.28 (t, J=8 Hz, 1H), 7.25 (t, J=8 Hz, 1H), 4.24 (q, J=7 Hz, 2H), 1.31 (t, J=7 Hz, 3H).

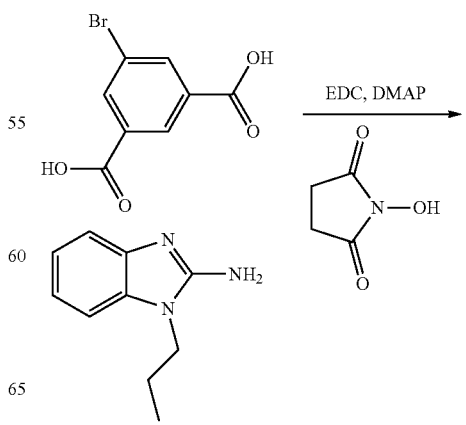

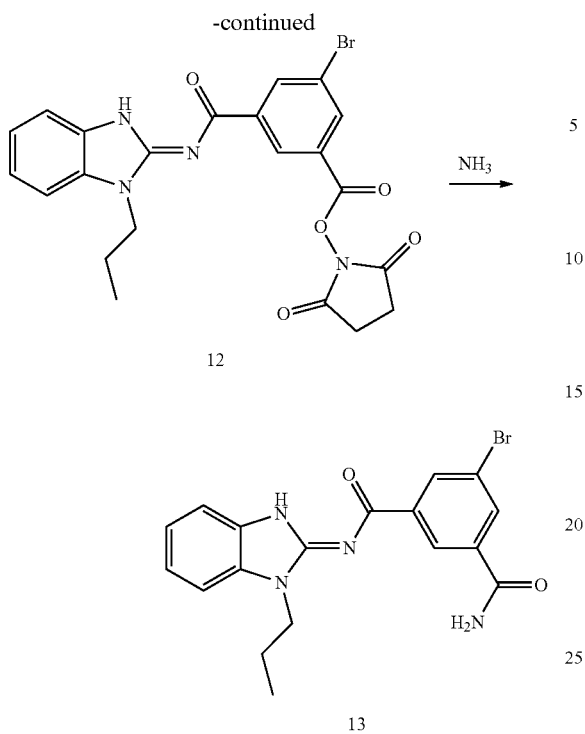

(E)-5-Bromo-N-(1-propyl-1,3-dihydro-2H-benzo[d]imidazol-2-ylidene)isophthalamide 13. A mixture of 5-bromoisophthalic acid (100 mg, 4.1 μmol), N-propylaminobenzamidazole (72 mg, 4.1 μmol), N-hydroxysuccinimide (56 mg, 4.9 μmol), DMAP (5 mg, 0.4 μmol) and EDC (234 mg, 1.2 mmol) were dissolved in methylene chloride (5 mL), treated with Hunig's base (53 mg, 4.1 μmol) and stirred for 1 d to give 12. The reaction mixture was then treated with 9/1 MeOH/NH$_4$OH (5 mL) and stirred for 2 h. The mixture was concentrated to a solid, dissolved in DMSO, added to a column and chromatographed (50 g isco C18, 0 to 100% MeOH with 0.2% formic acid) to give 13 (71 mg, 43%) as a white powder. LC/MS gave a single peak with m/z=401.1 [M+1]$^+$ and 823.1 [2M+Na]+. $^1$H-NMR (dmso-d$_6$) δ 12.77 (br s, 1H), 8.65 (br s, 1H), 8.45 (br s, 1H), 8.22 (br s, 1H), 8.17 (br s, 1H), 7.54-7.60 (m, 3H), 7.28 (t, J=8 Hz, 1H), 7.24 (t, J=8 Hz, 1H), 4.27 (t, J=7 Hz, 2H), 1.85 (h, J=7 Hz, 2H), 0.92 (t, J=7 Hz, 3H).

Synthesis of TAK1 Resin 1.

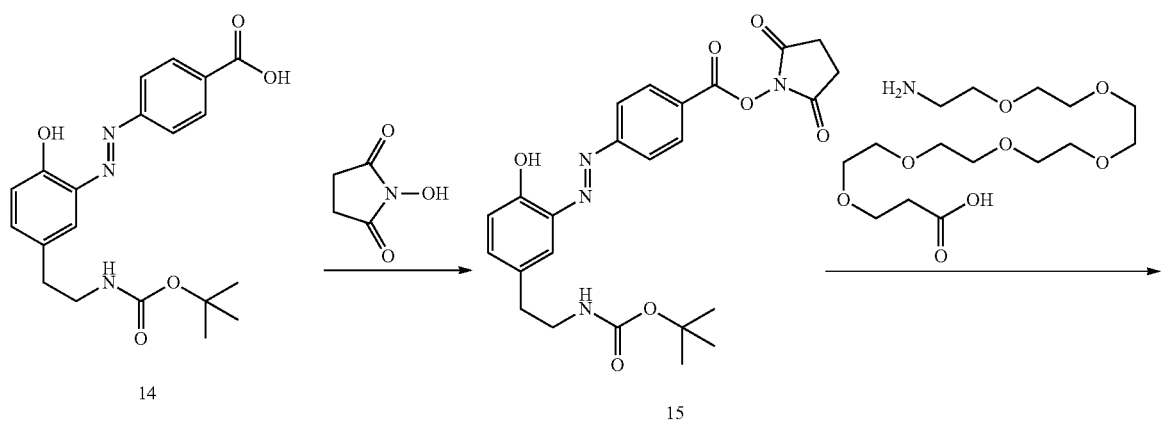

-continued
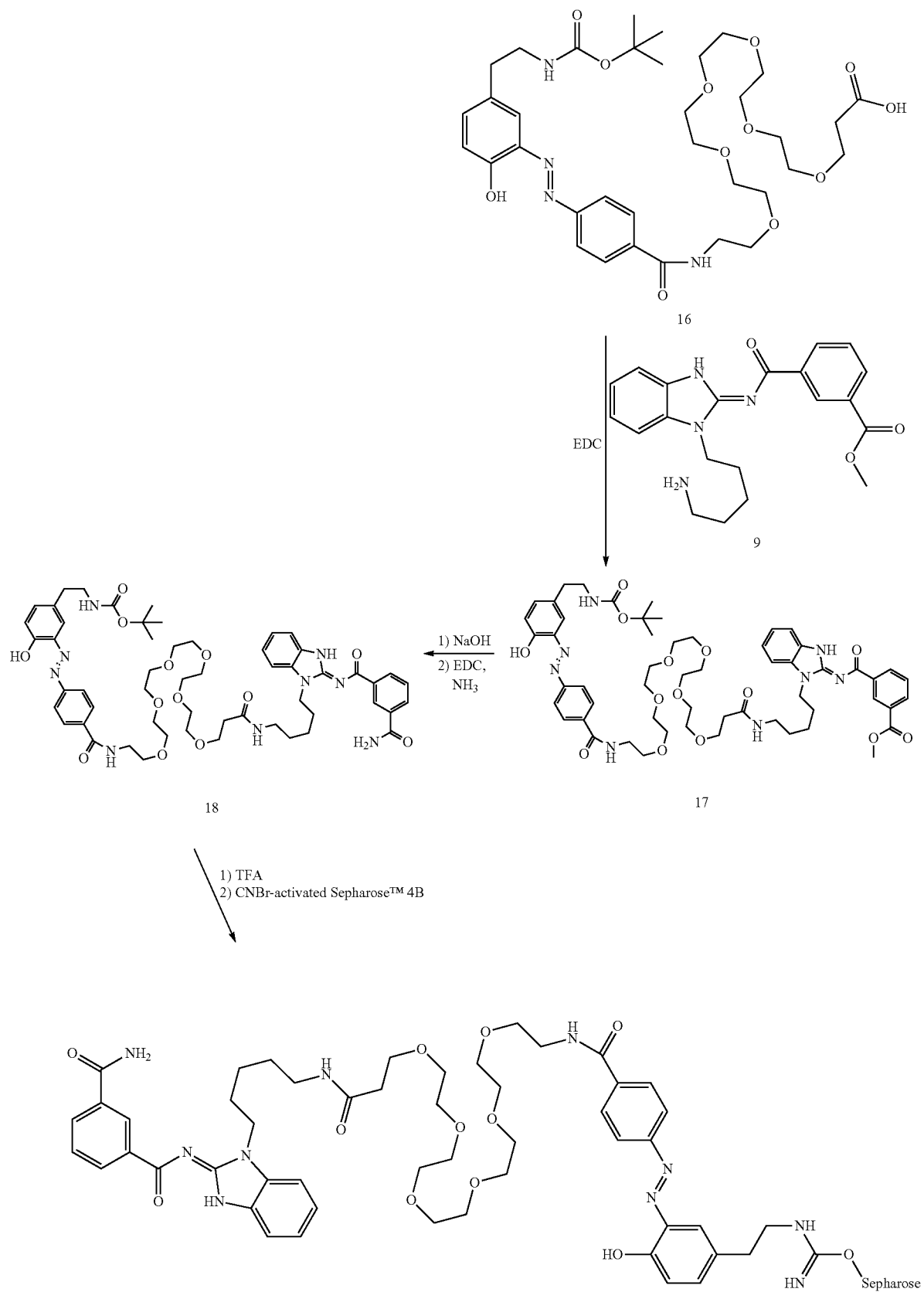

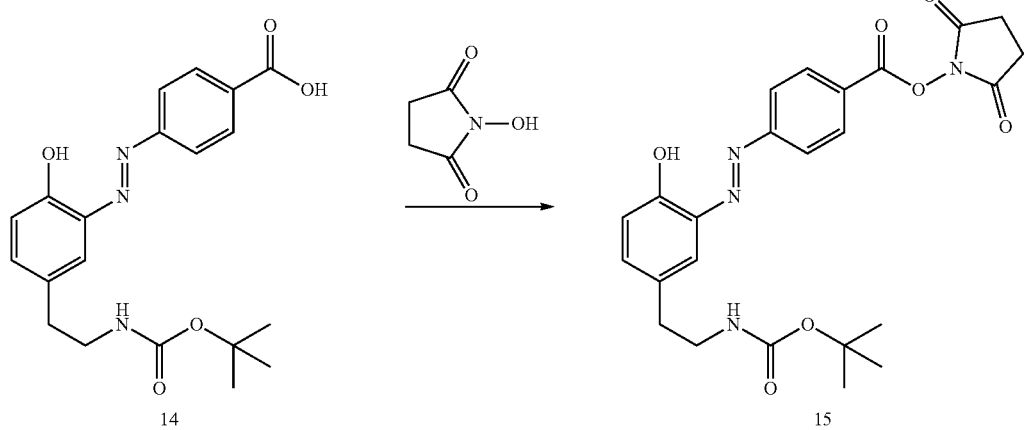

Acid 14 (Hughes et al., Bioorg. Med. Chem. 2012, 20(10), 3298-3305) (1 g, 2.6 mmol), EDC (1 g, 5.2 mmol), N-hydroxysuccinimide (450 mg, 3.9 mmol) and DMAP (13 mg) were slurried in DMF (8 mL) and stirred rapidly at 40° C. After a minute, the reaction mixture became homogeneous. After 1 hour, the reaction mixture was concentrated and chromatographed (silica gel, 0 to 100% ethyl acetate in methylene chloride). The product was triturated with hexanes and a trace of ethyl acetate, then filtered off and air-dried to give active ester 15 (814 mg, 64%) as an orange powder. $^1$H-NMR (CDCl$_3$) δ 8.30 (d, J=8 Hz, 2H), 7.98 (d, J=8 Hz, 2H), 7.82 (d, J=2 Hz, 1H), 7.2 (m under CDCl$_3$, 1H), 7.02 (d, J=8 Hz, 1H), 4.59 (OH?, br s, 1H), 3.43 (br m, 2H), 2.94 (br s, 4H), 2.86 (t, J=6 Hz, 2H), 1.44 (s, 9H).

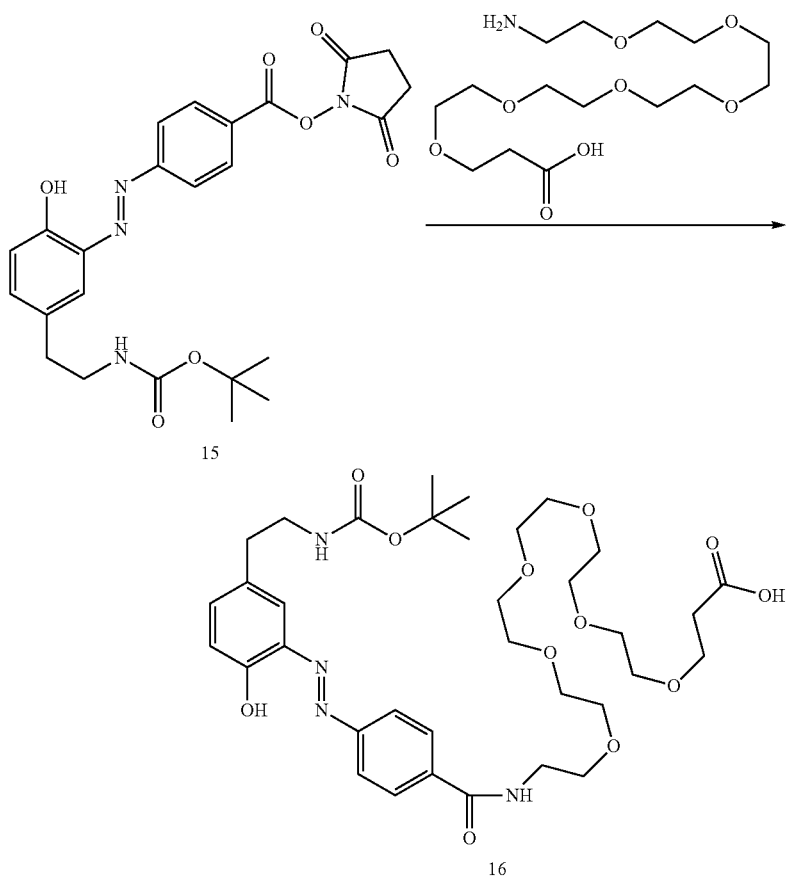

Active ester 15 (100 mg, 207 μmol), amino-dPEG®$_6$-acid (from Quanta Biodesign, 73.3 mg, 207 μmol) and Hunig's base (54 mg, 414 μmol) were dissolved in methylene chloride (2 ml) and stirred at RT. After 1 hour, the reaction mixture was concentrated, dissolved in DMSO (1 mL) and purified by prep HPLC (0 to 100% methanol, 20 mL/m, Agilent C-18 5 μm, 21.1×25 cm) to give acid 16 (130 mg, 87%) as a reddish glass. LC/MS gave a single peak with m/z=364.3 for [M+H]$^+$.

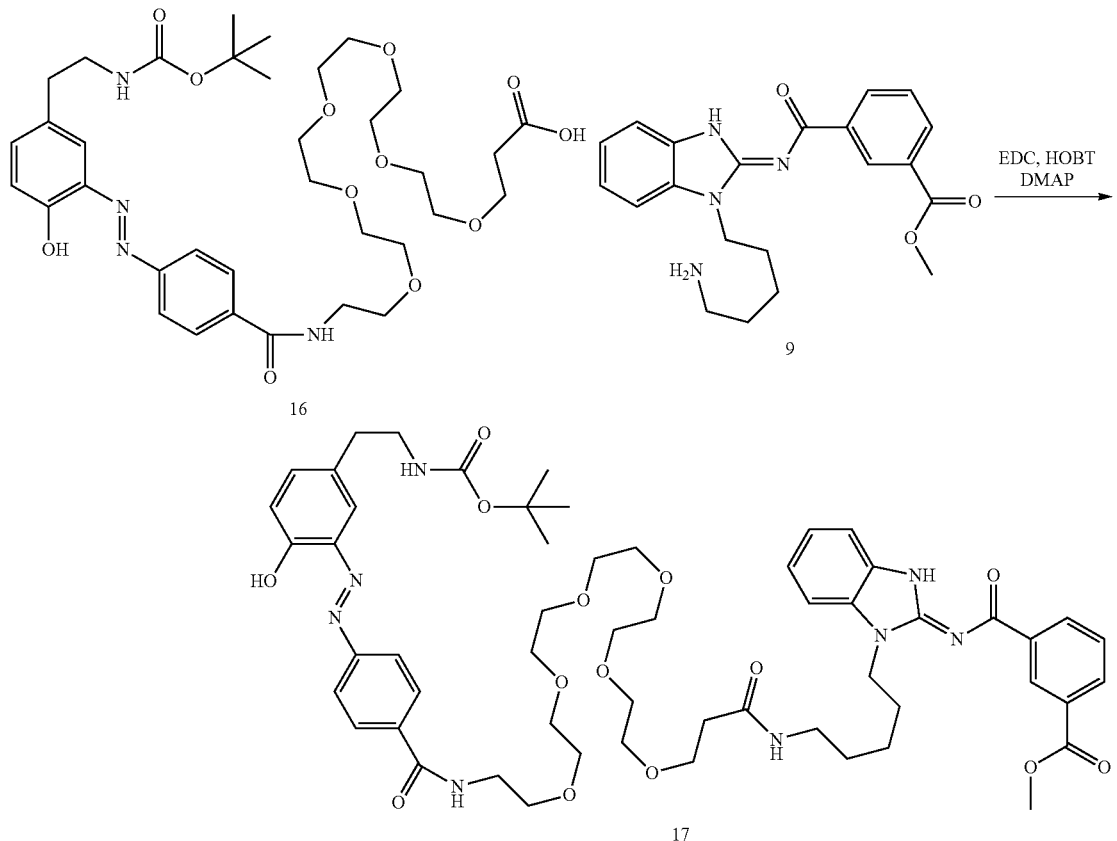

Ester 9 was dissolved in methylene chloride/methanol and treated with 2M HCl in dioxane (100 μL). The mixture was then concentrated to give the HCl salt. This salt (45 g, 103 μmol) and acid 16 (81 mg, 112 mmol) were mixed with EDC (54 mg, 280 μmol), HOBT (14 mg, 101 μmol) and DMAP (28 mg, 224 μmol) and dissolved in methylene chloride (1 mL) and stirred. After 1 h, the reaction mixture was concentrated onto silica and chromatographed (2×12 g silica, 0 to 10% MeOH in CH$_2$Cl$_2$) to give ligand 17 (38 mg, 32%) as an orange glass. LC/MS gives a single peak with m/z=1083.5.

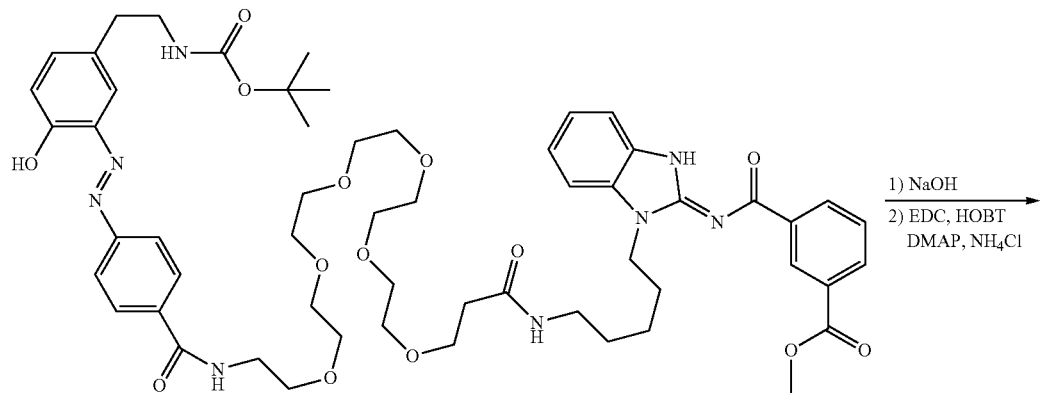

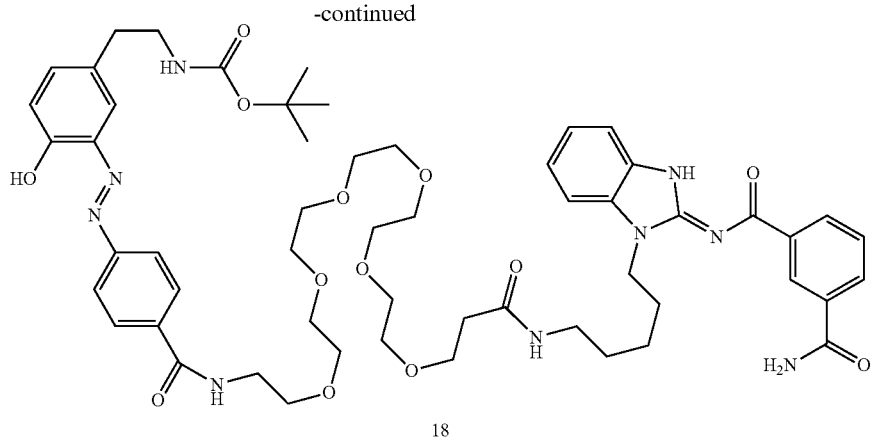

18

HS-226.

Ligand 17 (30 mg, 28 μmol) was dissolved in methanol and treated with 50% NaOH (10 drops) and stirred overnight. The reaction mixture was concentrated and chromatographed (43 g isco C18, 0 to 100% MeOH w/0.2% formic) to give the acid (30 mg) as an orange glass. The glass was treated with ammonium chloride (4.5 mg, 84 μmol), EDC (8 mg, 42 μmol), HOBT (6 mg, 42 μmol) and DMAP (1 mg) and Hunig's base (6 mg, 42 μmol) in methylene chloride (1 mL) and stirred at rt. The mixture was diluted with DMF (1 mL) and stirred for 3 d. The reaction mixture was concentrated and chromatographed (43 g isco C18, 0 to 100% MeOH w/0.2% formic) to give amide 18 (11.7 mg, 39%) as a yellow glass. LC/MS shows a single peak with m/z=1068.5 [M+H]$^+$ and m/z=484.7, which is [M-BOC+2H]$^{2+}$.

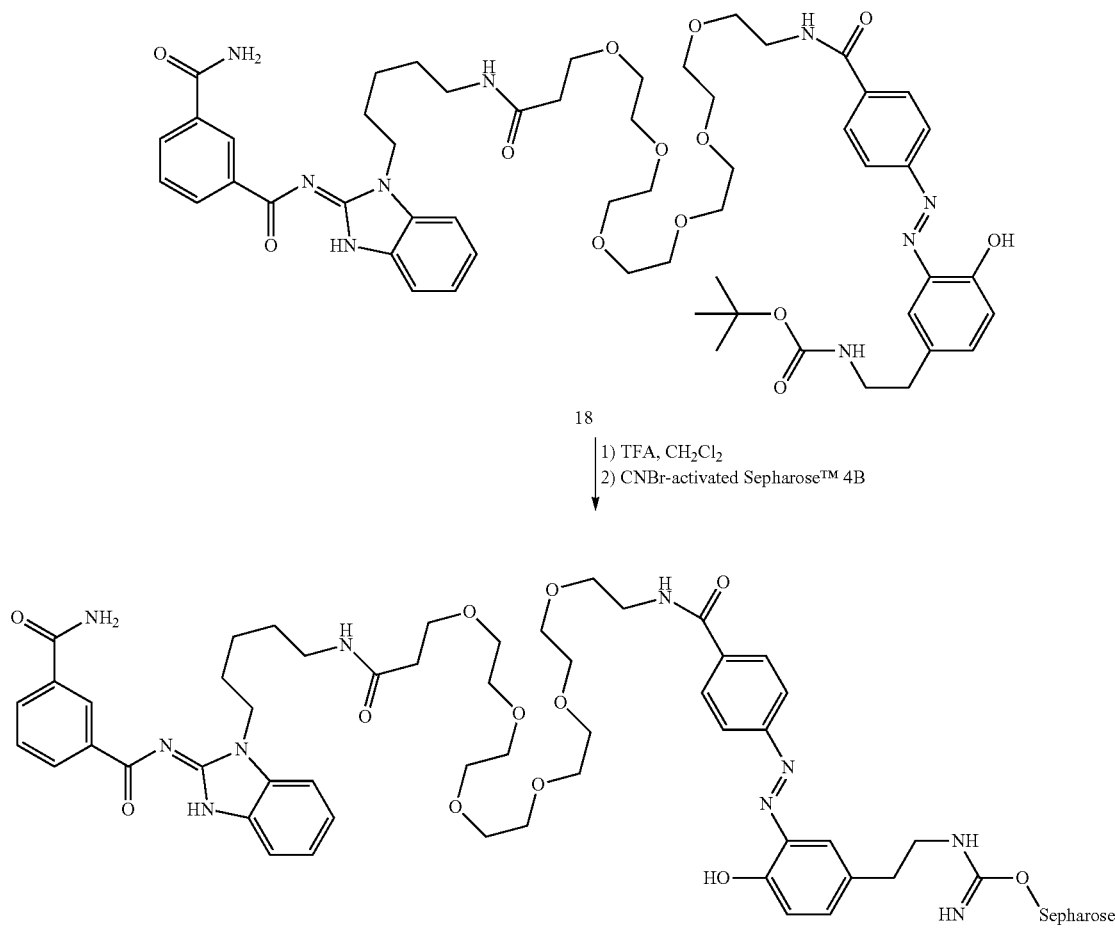

19 TAK1 resin 1

Buffers and Solutions

| Swelling solution | 1 mM HCl |
| --- | --- |
| Coupling buffer | 0.1M NaHCO$_3$, 0.5M NaCl, pH = 8.3 |
| Capping solution | 1M ethanolamine |
| Low buffer | 0.1M AcOH/NaOAc, 0.5M NaCl pH = 4 |
| High Buffer | 0.1M TRIS-HCl, 0.5M NaCl pH = 8 |
| Storage Buffer | 0.1M KH$_2$PO$_4$, pH = 7.4 w/ 200 mg NaN$_3$/L |

Compound 18 (4.8 mg, 4.5 μmol) was dissolved in methylene chloride (1 mL) and treated with TFA (200 μL). After 1 hour, the mixture was concentrated to a glass and dissolved in ethanol (~200 μL). LC/MS gave a single peak at m/z=968.5 and 484.7, [M+H]$^+$ and [M+2H]$^{2+}$ and TLC showed clean formation of a new peak and loss of the old one.

Roughly following GE Healthcare Instructions 71-7086-00 AFA.

In a 30 mL column, CNBr-activated Sepharose™ 4B (2 g) was swelled in 1 mM HCl (20 ml) and then washed with 1 mM HCl (400 mL). The resin was washed with coupling buffer (20 mL) and then slurried with coupling buffer (10 mL). The mixture was then treated with de-BOCed, 18 (see above). The mixture was tumbled at RT for 16 h. The resin was then drained (no color eluted) and washed with coupling buffer (5×10 mL), diluted with more coupling buffer (~10 mL) and treated with capping solution (200 uL) and rotated for 1 h. The solution was drained and washed with 3 rounds of high buffer/low buffer (20 mL ea.) and finally washed with water (20 mL) and transferred in storage buffer (20 mL) to a 40 mL EPA vial and stored at 4° C. as TAK1 resin 1, 19, estimated loading at 2.25 μmol/g.

Synthesis of TAK1 resins 2 and 3.

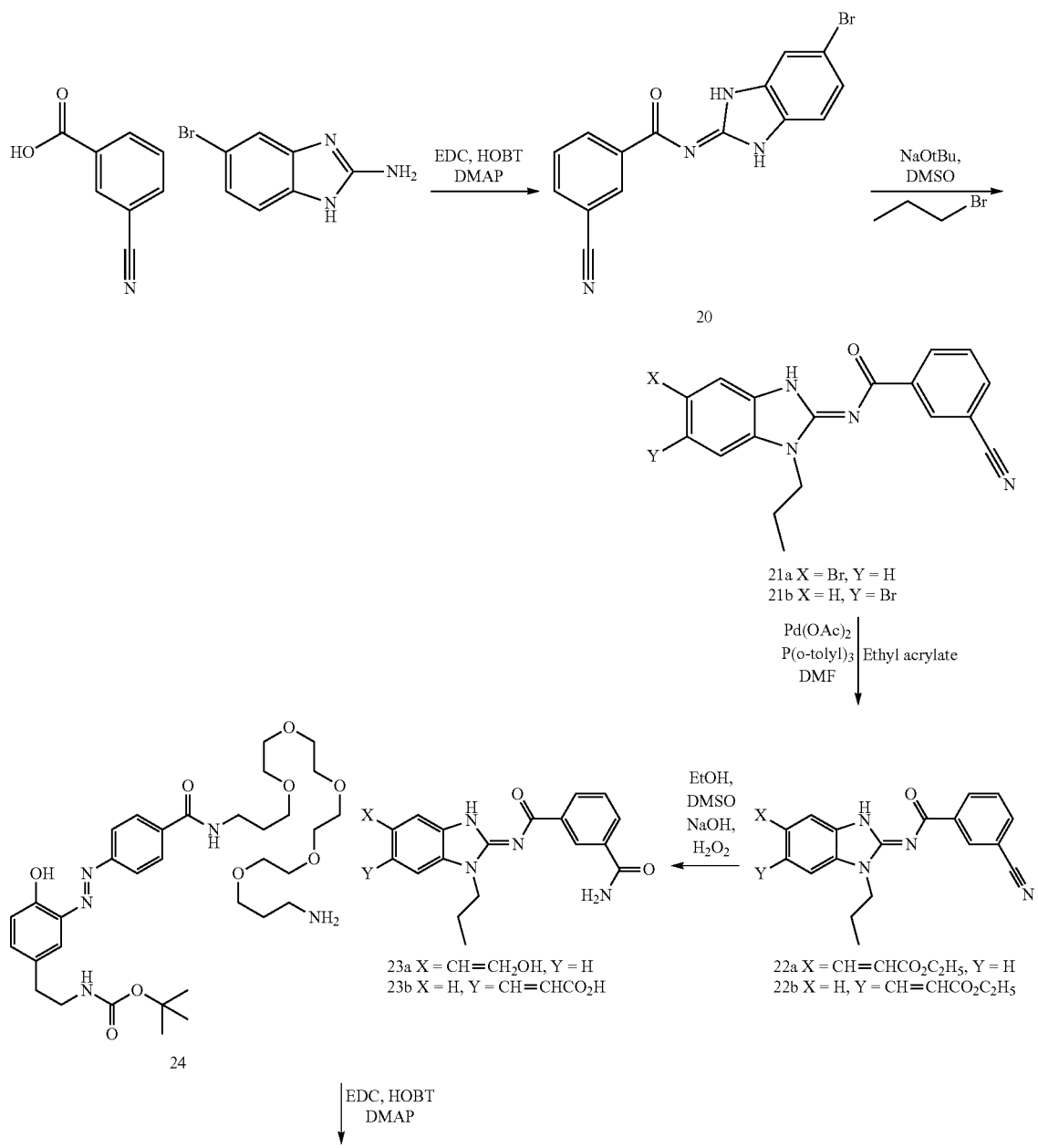

-continued

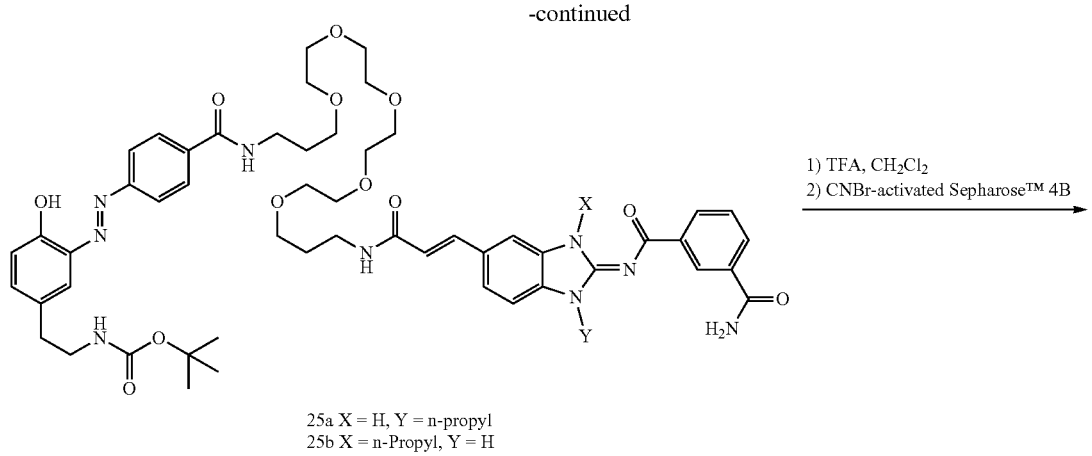

25a X = H, Y = n-propyl
25b X = n-Propyl, Y = H

26b TAK1 Resin 2 from 25b
26a TAK1 Resib 3 from 25a

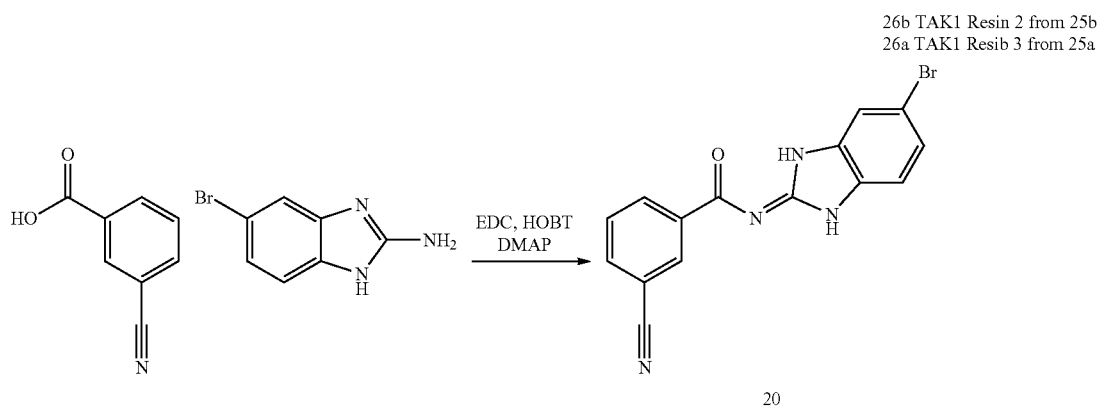

20

3-Cyanobenzoic acid (600 mg, 4.08 mmol) and 5-bromo-1H-benzo[d]imidazol-2-amine (865 mg, 4.08 mmol) were mixed with EDC (1.56 g, 8.16 mmol), HOBT (551 mg, 4.08 mmol) and DMAP (10 mg, 82 μmol), slurried in DMF (5 mL) and treated with Hunig' base (527 mg, 4.08 mmol). The mixture was stirred for 16 h and then concentrated. The solid residue was slurried in hot ethanol, cooled and a white powder was filtered off, washed with ethanol and air-dried to give nitrile 20 (980 mg, 70%) as an off-white solid. LC/MS looks marvelous with a single peak with m/z=341.0 and 343.0, [M+H]⁺.

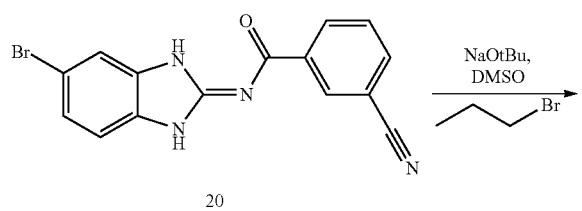

-continued

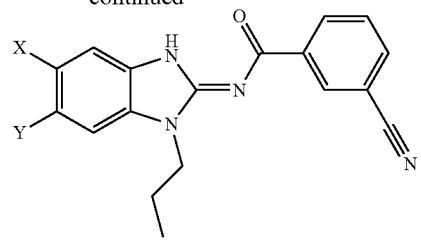

21a X = Br, Y = H
21b X = H, Y = Br

Nitrile 20 (980 mg, 2.97 mmol) was dissolved in THF (18 mL) and DMSO (7.5 mL) and treated with potassium t-butoxide (5.7 mL of 1M THF solution) followed by 1-bromopropane (333 μL, 706 mg, 5.7 mmol) and stirred at RT. After 2 h, the mixture was treated with a little acetic acid (200 μL) and stirred for an hour. The mixture was then poured into water (100 mL) giving rise to substantial precipitation. The slurry was stirred vigorously overnight then filtered and air-dried to give a mixture of 21a and 21b (838 mg, 76%) as a fluffy white powder. Some of the mixture (400 mg) was adsorbed onto silica and chromatographed (80 g Isco silica gel, 0 to 20% EtOAc in CH₂Cl₂) to give a partial separation of the two compounds. The clean fractions of the earlier eluting compound were combined to give 21a (called upper bromide, 184 mg). LC/MS shows a single tailing peak with m/z=383.1 and 385.1, [M+H]+. ¹H-NMR (dmso-d₆) δ 8.52 (s, 1H), 8.51 (d, J=8 Hz, 1H), 8.00 (d, J=8 Hz, 1H), 7.71, (t, J=8 Hz, 1H), 7.70 (s, 1H), 7.55 (d, J=8 Hz, 1H), 7.43 (d, J=8 Hz, 1H), 4.25 (t, J=7 Hz, 2H), 1.83 (p, J=7 Hz, 2H), 0.91 (t, J=7 Hz, 3H).

The clean fractions of the later eluting compound were combined to give 21b (called lower bromide, 145 mg). LC/MS shows a single tailing peak with m/z=383.1 and 385.1, ¹H-NMR (dmso-d₆) δ 8.52 (s, 1H), 8.51 (d, J=8 Hz, 1H), 7.99 (d, J=8 Hz, 1H), 7.87 (s, 1H), 7.71, (t, J=8 Hz, 1H), 7.47 (d, J=8 Hz, 1H), 7.40 (d, J=8 Hz, 1H), 4.25 (t, J=7 Hz, 2H), 1.83 (p, J=7 Hz, 2H), 0.93 (t, J=7 Hz, 3H).

We were unable to obtain adequate NOe spectra to assign the structures. Identification of the isomeric structures was assigned later base on an unambiguous region-controlled synthesis of 21a (see below).

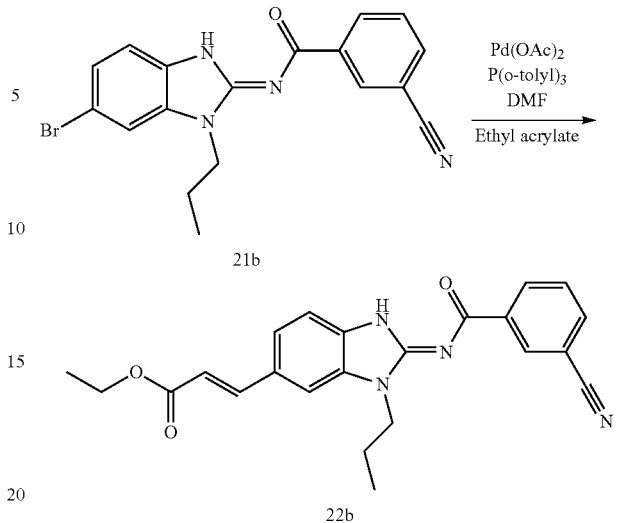

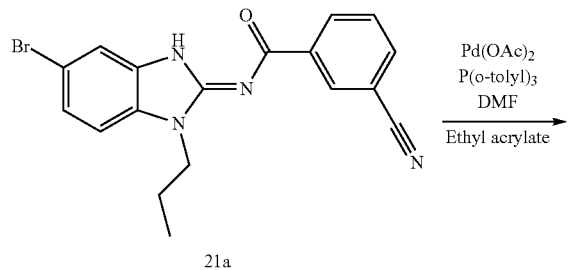

Nitrile 21a (upper bromide, 100 mg, 261 μmol) was mixed with tri(o-tolyl)phosphine (9.5 mg, 31 μmol) and palladium(II) acetate (6 mg, 26 μmol) in DMF (1 mL) and treated with triethylamine (53 mg, 522 μmol) and ethyl acrylate (52 mg, 522 μmol) and stirred at RT with nitrogen bubbling. The mixture was then heated to 125° C. under nitrogen for 20 h and allowed to cool.

The reaction mixture was diluted with DMSO (1 mL) and heated slightly to re-dissolved the product. The mixture was passed through a filter to remove palladium onto a column and chromatographed (43 g Isco C-18, 0 to 100% MeOH in 0.2% HCO₂H) to give 22a (86 mg, 82%) as a white solid. LC/MS gave a single peak with m/z=403.2 [M+H]+. ¹H-NMR (dmso-d₆) δ 8.54 (s 1H), 8.52 (d, J=8 Hz, 1H), 8.00 (d, J=8 Hz, 1H), 7.78 (s, 1H), 7.73 (d, J=16 Hz, 1H), 7.72 (t, J=8 Hz, 1H), 7.69 (d, J=8 Hz, 1H), 7.62 (d, J=8 Hz, 1H), 6.53 (d, J=16 Hz, 1H), 4.28 (t, J=7 Hz, 2H), 4.20 (q, J=7 Hz, 2H), 1.84 (hex, J=7 Hz, 2H), 1.27 (t, J=7 Hz, 3H), 0.93 (t, J=7 Hz, 3H).

Nitrile 21b (100 mg, 261 μmol) was reacted as described above for 21a to give 22b (103 mg, 98%) as a white solid. LC/MS gave a single peak with m/z=403.3 [M+H]+. ¹H-NMR (dmso-d₆) δ 8.53 (s 1H), 8.51 (d, J=8 Hz, 1H), 8.06 (s, 1H), 8.00 (d, J=8 Hz, 1H), 7.73 (d, J=16 Hz, 1H), 7.71 (t, J=8 Hz, 1H), 7.59 (d, J=8 Hz, 1H), 7.54 (d, J=8 Hz, 1H), 6.75 (d, J=16 Hz, 1H), 4.28 (t, J=7 Hz, 2H), 4.20 (q, J=7 Hz, 2H), 1.86 (hex, J=7 Hz, 2H), 1.27 (t, J=7 Hz, 3H), 0.95 (t, J=7 Hz, 3H).

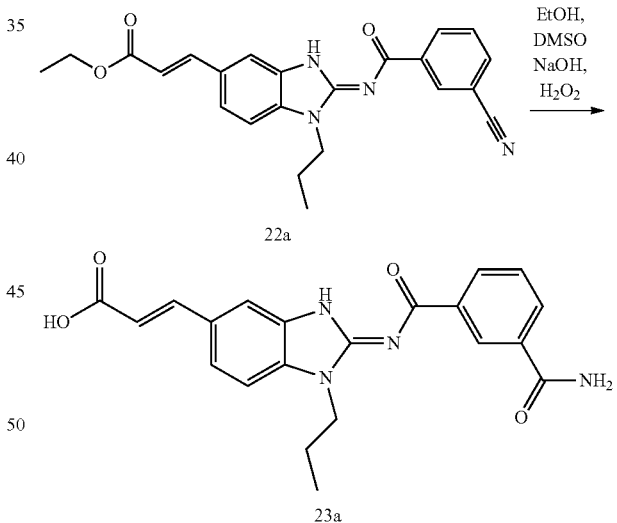

HS-234. Nitrile 22a (150 mg, 373 μmol) was slurried in ethanol (4 mL) and treated with 50% NaOH (12 drops, about 25 mg NaOH/drop, 300 mg) followed by 30% hydrogen peroxide (5 drops). The mixture was stirred at rt for 3 d. The mixture was then acidified by slow addition of 1N HCl to pH=1 which led to precipitation of the product. The solid was then filtered off and washed with water and air dried overnight to give 22a (141 mg, 96%) as an off white solid. LC/MS gave a single peak with m/z=393.2 [M+H]+. ¹H-NMR (dmso-d₆) δ 8.68 (s, 1H), 8.38 (d, J=8 Hz, 1H), 8.11 (br s, 1H), 8.00 (d, J=8 Hz, 1H), 7.77 (s, 1H), 7.66 (d, J=16 Hz, 1H), 7.57-7.63 (m, 2H), 7.55 (t, J=8 Hz, 1H), 7.42

(br s, 1H), 6.43 (d, J=16 Hz, 1H), 4.27 (t, J=7 Hz, 2H), 1.85 (hx, J=7 Hz, 2H), 0.93 (t, J=7 Hz, 3H).
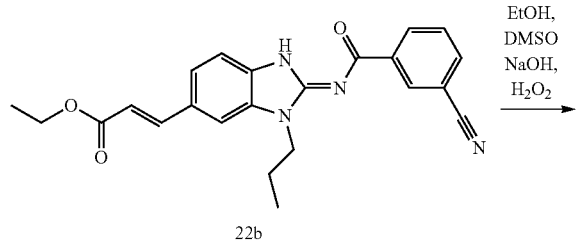
22b
EtOH, DMSO, NaOH, H₂O₂ →
-continued
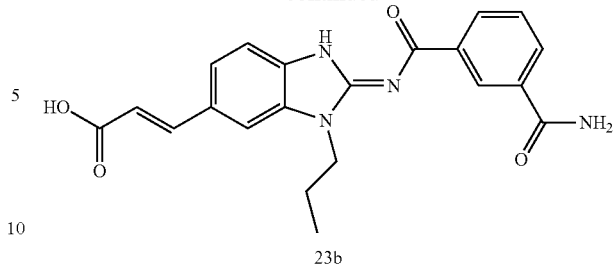
23b
HS-233.
Nitrile 22b (50 mg, 124 μmol) was reacted as described above for 22a to give 23b (103 mg, 98%) as a white solid. LC/MS gave a little peak which trailed out in the MS forever with m/z=393.2, [M+H]⁺. NMR gave broad but consistent peaks in DMSO.]⁺. ¹H-NMR (dmso-d₆) δ 8.68 (br s, 1H), 8.37 (br d, 1H), 7.91 (br d, 1H), 7.74 (br s, 1H), 7.65 (br d, J=16 Hz, 1H), 7.42-7.53 (m, 3H), 6.51 (br d, J=16 Hz, 1H), 4.26 (br ?, 2H), 1.86 (m, 2H), 0.94 (br, 3H).
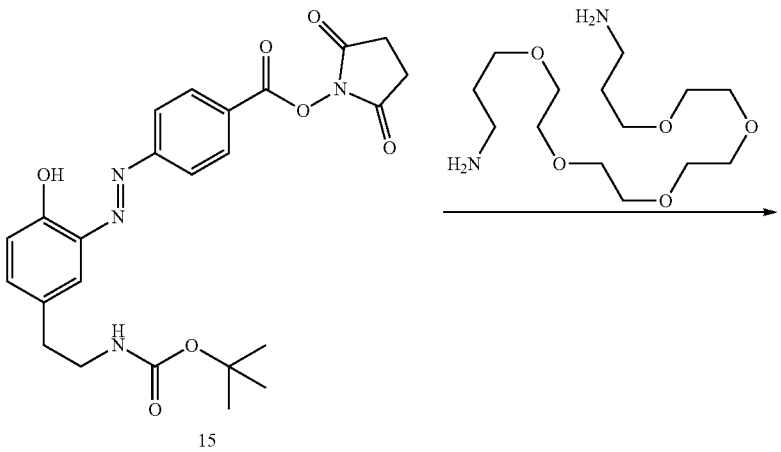
15
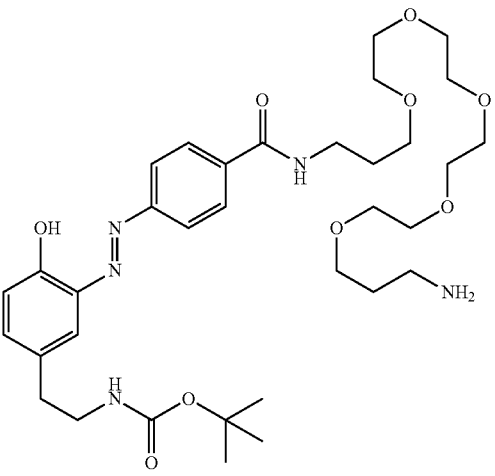
24

Diamine (1,19-diamino-4,7,10,13,16-pentaoxanonadecane 154 mg mg, 500 µmol) was dissolved (154 mg mg, 500 µmol) was dissolved in methylene chloride (2 mL) and treated dropwise with active ester 15 (241 mg, 500 µmol) in methylene chloride (2 mL) for 2 h. The reaction mixture was concentrated and chromatographed (25 g isco silica gel, 0 to 30% 9/1:MeOH/NH$_4$OH in CH$_2$Cl$_2$) to give amine 24 (159 gm, 47%) as a red residue. LC/MS shows a single peak with m/z=676.4 [M+1]$^+$. $^1$H-NMR (CDCl$_3$), δ 8.72 (NH, br t, J=6 Hz, 1H), 8.30 (d, J=8 Hz, 2H), 7.90 (d, J=8 Hz, 2H), 7.84 (NH?, br s, 1H), 7.78 (d, J=2 Hz, 1H), 7.2 (dd, J=2, 8 Hz, 1H), 6.98 (d, J=8 Hz, 1H), 4.59 (OH?, br s, 1H), 3.55-3.81 (br m, 22H), 3.43 (br q, J=6 Hz, 2H), 3.19 (t, J=6 Hz, 2H), 2.84 (t, j=7 Hz, 2H), 2.09 (pen, J=6 Hz, 2H), 2.04 (pen, J=6 Hz, 2H), 1.44 (s, 9H).

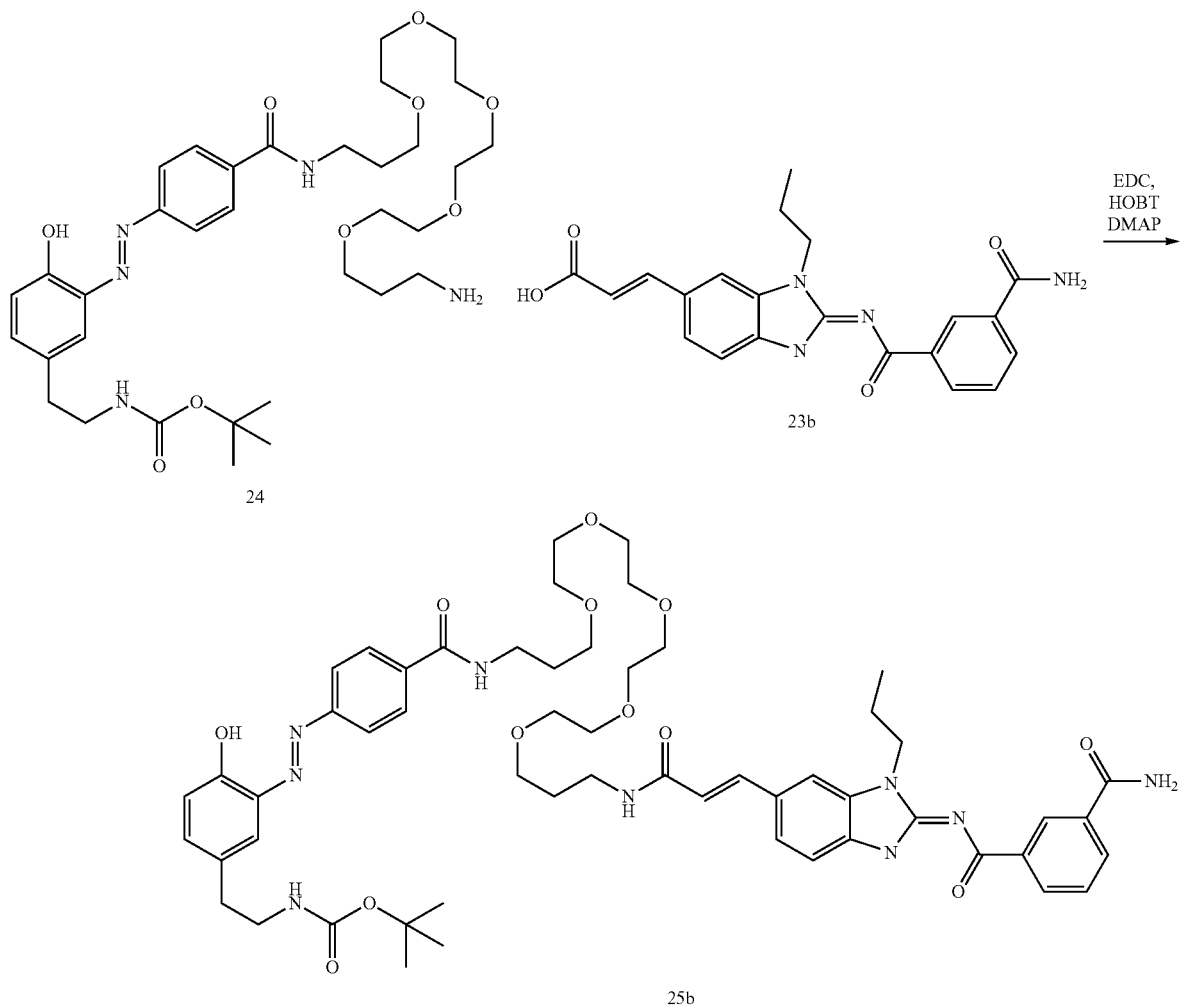

Ligand 23b (4.5 mg, 11.5 µmol) and amine 24 (7.75 mg, 11.5 µmol) were mixed with HOBT (5 mg, 34 µmol) and DMAP (4 mg, 34 µmol) and slurried in DMF (300 µL). EDC (6.6 mg, 34 µmol) was then added and the mixture stirred at RT for 16 h. The entire reaction mixture was injected on the prep HPLC (0.2% formate to 100% methanol, 20 mL/m, Agilent 5 µm C-18, 21.1×25 cm) to give 25b (7.1 mg, 60%) as an orange solid. LC/MS gave a single peak with m/z=1050.8 for [M+H]$^+$.

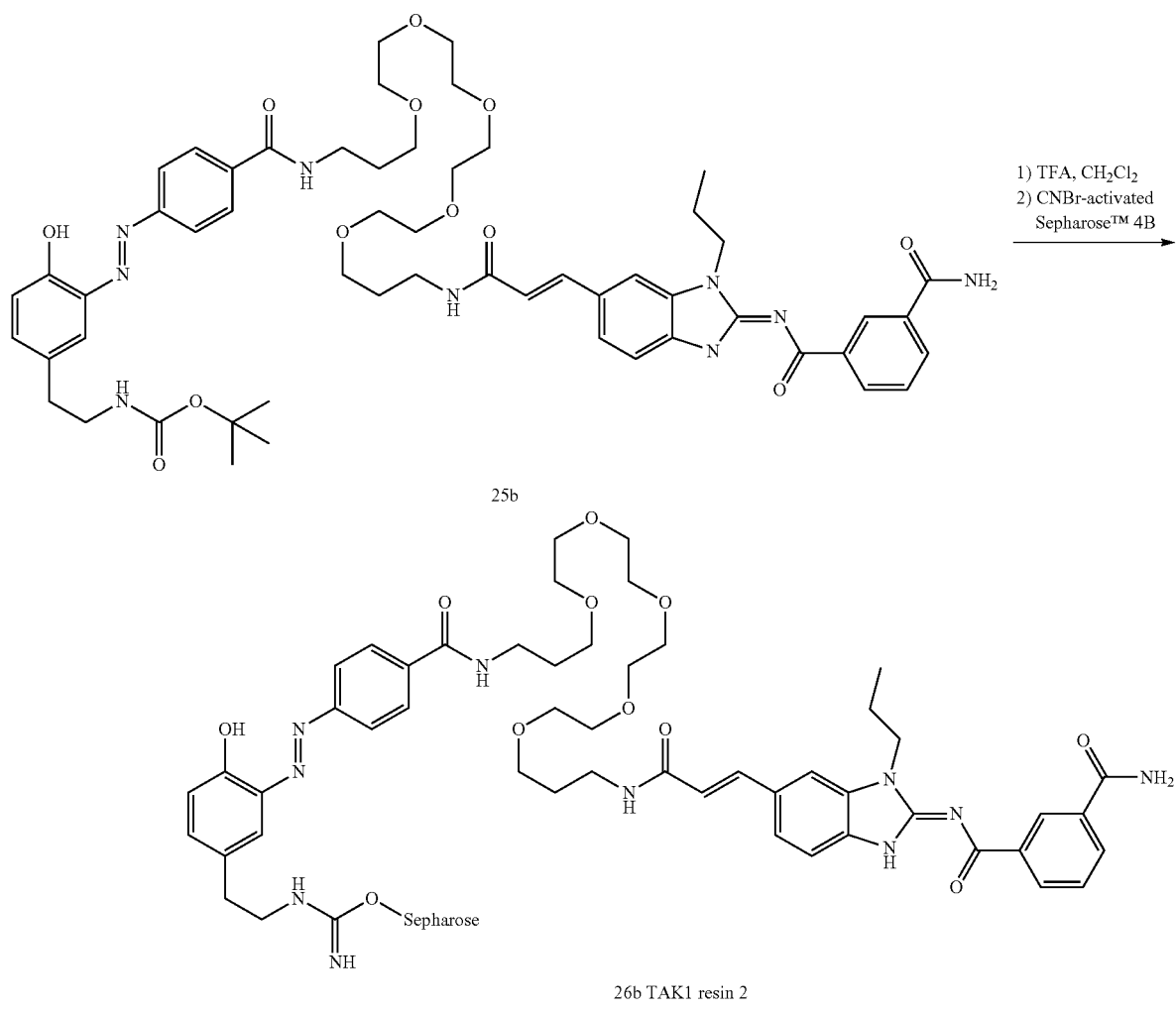
Using the methods described for the synthesis of 7, TAK1 Resin 0, compound 25b was first treated with TFA to remove the BOC group. LC/MS gave a peak with m/z=950.7 and 475.9, [M+H]$^+$ and [M+2H]$^{2+}$, respectively. In this case, the amine was isolated (2.1 mg) and was then reacted with resin (1 g dry) as described above (synthesis of 19) to give 26b, TAK1 resin 2.
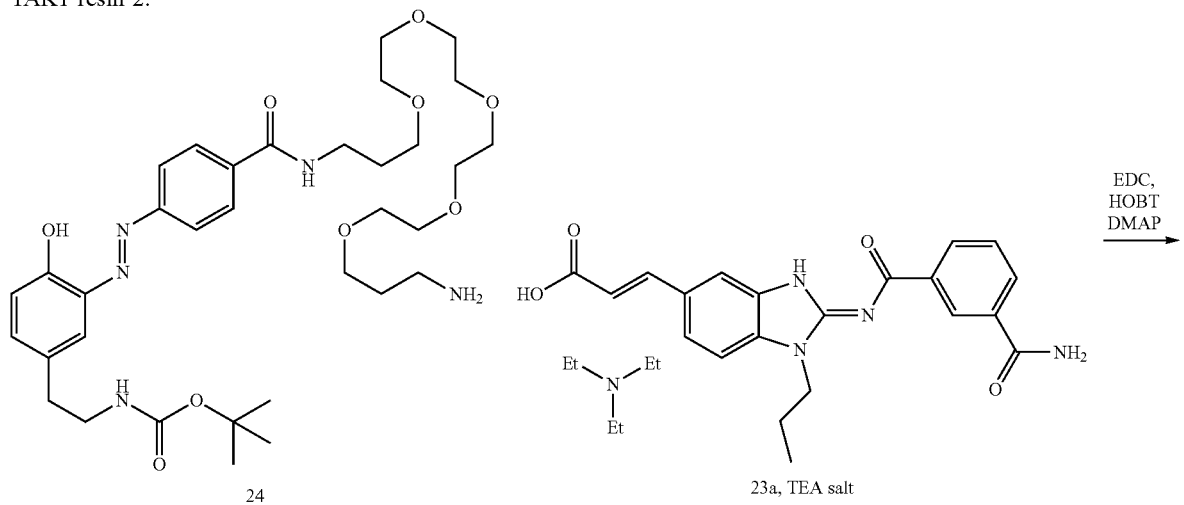

-continued

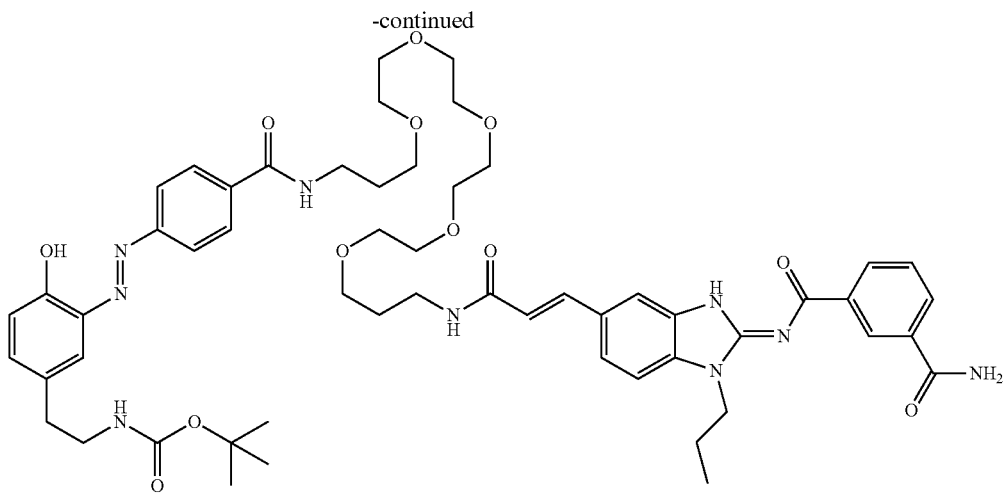

25a

Ligand 23a (as a TEA salt, 20.8 mg, 35 μmol) and amine 24 (24 mg, 35 μmol) were mixed with HOBT (14 mg, 105 μmol) and DMAP (13 mg, 105 μmol) and slurried in DMF (600 μL). EDC (20 mg, 105 μmol) was then added and the mixture stirred at RT for 16 h. The entire sample was diluted with DMSO (1 mL), loaded onto a column and chromatographed (50 g isco C-18, 0.2% formic in water to 100% MeOH) to give a mixture of compounds. LC/MS showed m/z=1424.8, indicating bis acylation. The mixture was dissolved in methanol (5 mL) and treated with $K_2CO_3$ (50 mg) and stirred with mild warming overnight. The sample was then concentrated, dissolved in DMSO and chromatographed again (50 g isco C-18, 0.2% formic in water to 100% MeOH) to give 2 products. The later eluting product was concentrated to give the desired product 25a (7.7 mg, 21%). LC/MS gave a single peak with m/z=1050.7 for $[M+H]^+$.

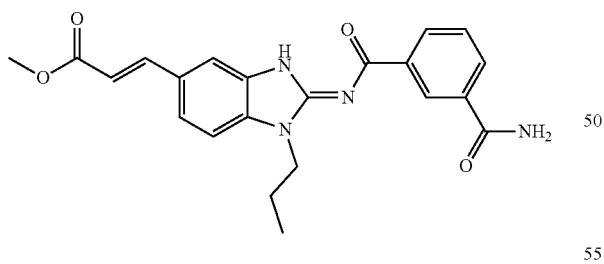

27

The earlier eluting peak was concentrated to give ester 27, HS-235 (2.8 mg). LC/MS gave a single peak with m/z=407.2 for $[M+H]^+$. $^1$H-NMR (dmso-$d_6$) δ 8.68 (s, 1H), 8.38 (d, J=8 Hz, 1H), 8.11 (br s, 1H), 8.00 (d, J=8 Hz, 1H), 7.79 (s, 1H), 7.74 (d, J=16 Hz, 1H), 7.68 (d, J=8 Hz, 1H), 7.60 (d, J=8 Hz, 1H), 7.55 (t, J=8 Hz, 1H), 7.42 (br s, 1H), 6.53 (d, J=16 Hz, 1H), 4.27 (t, J=7 Hz, 2H), 3.74 (s, 3H), 1.85 (hex, J=7 Hz, 2H), 0.93 (t, J=7 Hz, 3H).

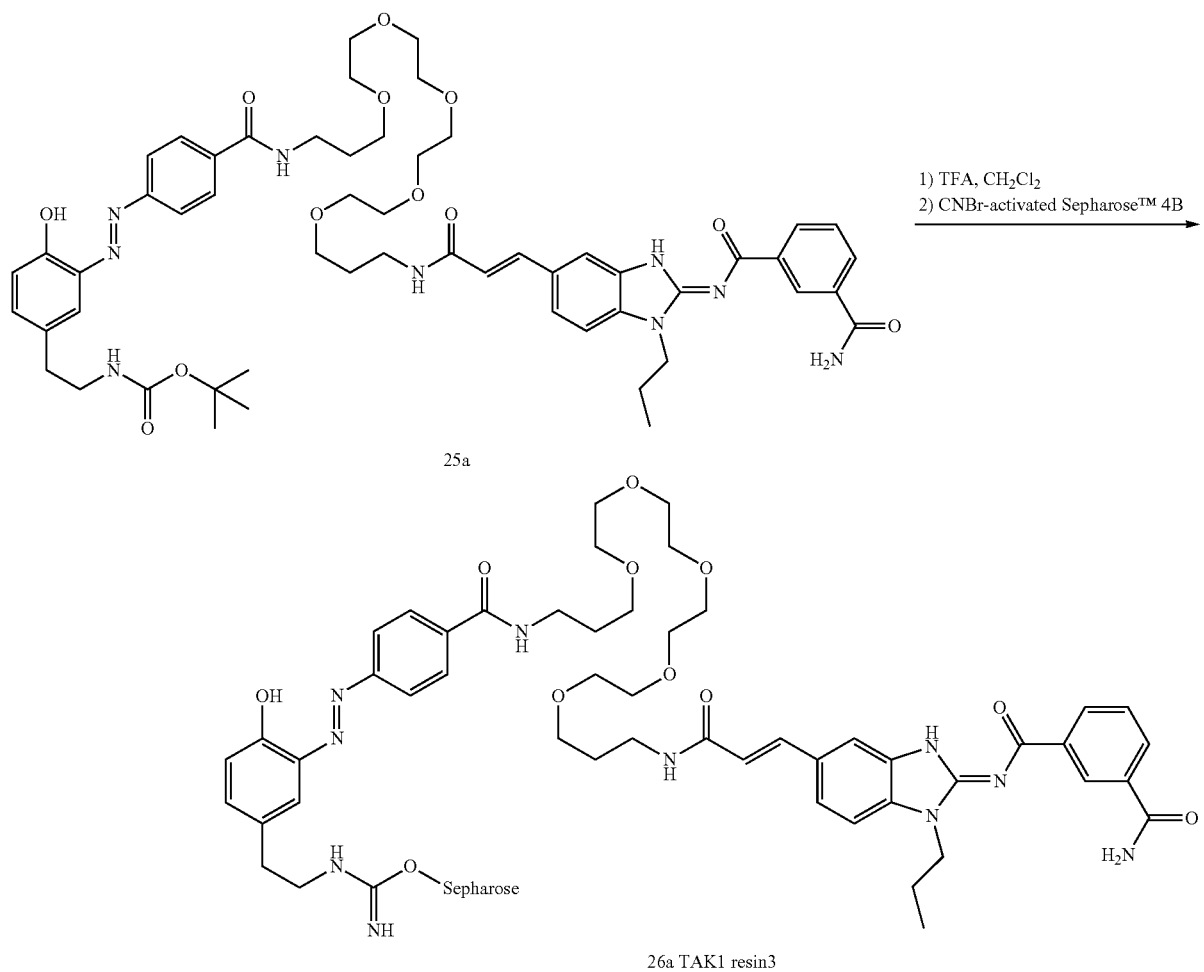
Using the methods described for the synthesis of 7, TAK1 Resin 0, compound 25a (7.7 mg, 7.33 μmol) was first treated with TFA to remove the BOC group. When complete by TLC, the reaction mixture was concentrated and the residue reacted with resin (2 g dry) as described above (synthesis of 19) to give 26a, TAK1 resin 3.
Independent Synthesis of 21a
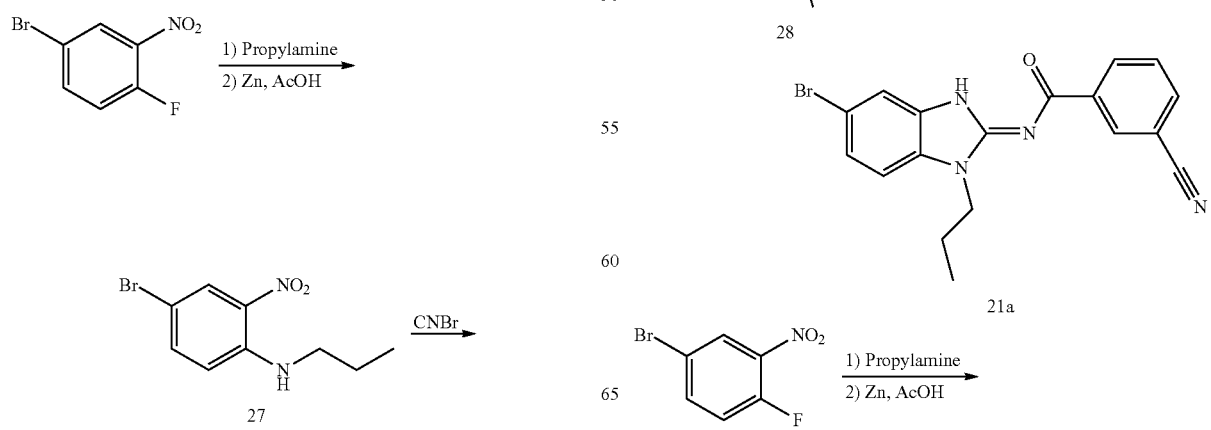

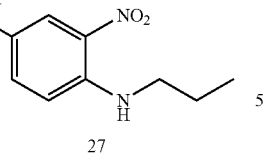

27

4-Bromo-1-fluoro-2-nitrobenzene (1.5 g, 6.8 mmol) was dissolved in ethanol (10 mL) and treated with propyl amine (1.21 g, 1.68 mL, 20.4 mmol) and stirred at RT overnight. The next day, the reaction mixture was concentrated then re-dissolved in ethanol (20 mL) and acetic acid (5 mL). The mixture was treated with zinc powder (4 g) and heated to 80° C. with stirring for 1 h. The reaction was allowed to cool and was filtered through Celite® with an ethanol wash. The eluant was concentrated then chromatographed (Silica gel, 100% $CH_2Cl_2$) to give the aniline 27 (1.49 g, 95%) as a clear oil which solidified on standing. LC/MS gave a single peak with m/z=229.0 for $[M+H]^+$. $^1$H-NMR (dmso-$d_6$) δ 6.65 (d, J=2.3 Hz, 1H), 6.57 (dd, J=2.3, 8 Hz, 1H), 6.29 (d, J=8 Hz, 1H), 4.83 (br s, 2H), 4.49 (br t, J=5 Hz, 1H), 2.94 (br q, J=6 Hz, 2H), 1.58 (hex, J=7 Hz, 2H), 0.94 (t, J=7 Hz, 3H).

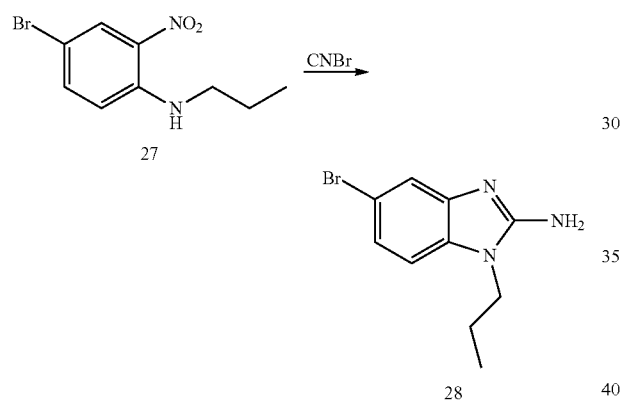

Analogous to J. Med. Chem. 2012, 55, 6523-6540. Bromoaniline 27 (440 mg, 1.93 μmol) was dissolved in ethanol (4 mL) and treated with fresh cyanogen bromide (306 mg, 2.89 μmol) and stirred at RT. After 1 h, the mixture was concentrated to give pink solid (728 mg). The pink solid was re-dissolved in ethanol, treated with xs 9/1:MeOH/NH$_4$OH (2 mL) and concentrated onto silica gel (4 g) and chromatographed (40 g isco silica, 0 to 10% MeOH in $CH_2Cl_2$) to give 2-aminobenzimidazole 28 (421 mg, 86%) as a white solid. LC/MS gave a single peak with m/z=254.0 for $[M+H]^+$. $^1$H-NMR (dmso-$d_6$) δ 7.23 (br s, 1H), 7.1 (d, J=8 Hz, 1H), 6.29 (br d, J=8 Hz, 1H), 6.59 (br s, 2H), 3.91 (t, J=7 Hz, 2H), 1.62 (hex, J=7 Hz, 2H), 0.84 (t, J=7 Hz, 3H).

3-Cyanobenzoic acid (116 mg, 788 μmol) and 2-aminobenzimidazole 28 (200 mg, 788 μmol) were mixed with EDC (302 mg, 1.58 mmol), HOBT (106 mg, 788 μmol), DMAP (2 mg, 16 μmol) and slurried in DMF (2 mL) and treated with Hunig's base (102 mg, 788 μmol). The mixture was gently heated to dissolve everything and stirred at RT overnight. The next day, the reaction mixture was diluted with methanol (20 mL) and stirred as solids precipitated out. The solid was filtered off, washed with methanol, and air dried overnight to give nitrile 9a (229 mg, 76%) as a white powder. Compound 21a, prepared in this way, is identical to 21a and different from 21b, prepared by separation as described above.

Synthesis of TAK1 Protac Agent

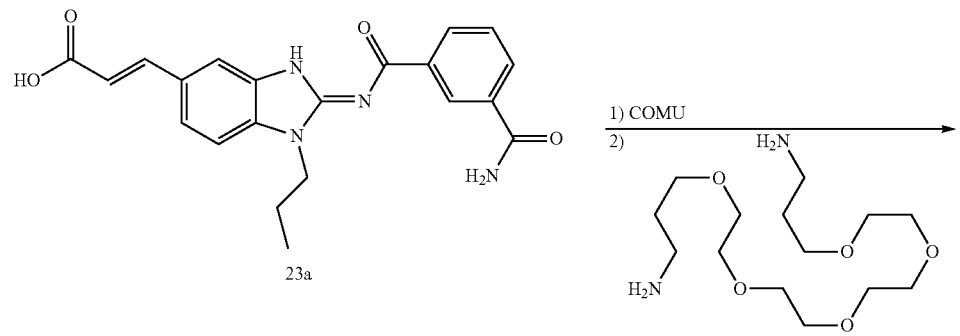

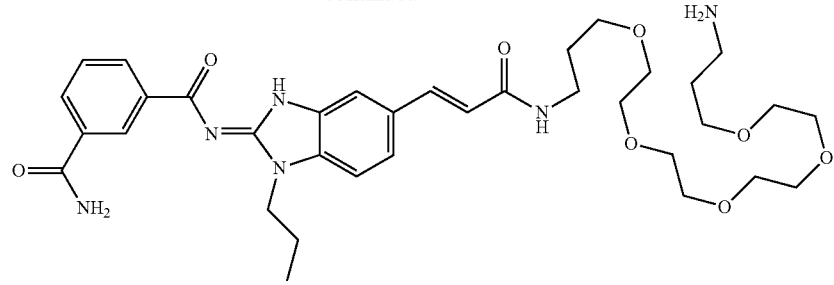

29

COMU (57 mg, 134 μmol) and acid 23a (50 mg, 127 μmol) were dissolved in DMF (500 μL) and treated with Hunig's base (17 mg, 127 μmol). A lot of precipitate formed. After 5 m, diamine (1,19-diamino-4,7,10,13,16-pentaoxanonadecane, 86 mg, 280 μmol) was added in DMF (500 μL) and the mixture was stirred at RT. After 2 h, the entire reaction mixture was added to a column and chromatographed (50 g isco C-18, 0.2% formic in water to 100% MeOH) to give separated bis adduct and the desired amine 29 (34 mg, 39%) as a clear glass. LC/MS gave a single peak with m/z=683.3 for [M+H]$^+$. $^1$H-NMR (dmso-$d_6$) δ 8.68 (s, 1H), 8.42 (s, 1H), 8.32 (d, J=8 Hz, 1H), 8.17 (t, J=6 Hz, 1H), 8.10 (br s, 1H), 7.99 (d, J=8 Hz, 1H), 7.72 (d, J=8 Hz, 1H) 7.57 (d, J=8 Hz, 1H), 7.55 (t, J=8 Hz, 1H0 7.47 (d, J=16 Hz, 1H), 7.46 (d, J=8 Hz, 1H), 7.42 (br s, 1H), 6.56 (d, J=16 Hz, 1H), 4.26 (t, J=7 Hz, 2H), 3.42-3.57 (m, 20H), 3.24 (q, J=6 Hz, 2H), 2.75 (t, J=7 Hz, 2H), 1.85 (hex, J=7 Hz, 2H), 1.70 (p, J=7 Hz, 4H), 0.93 (t, J=7 Hz, 3H).

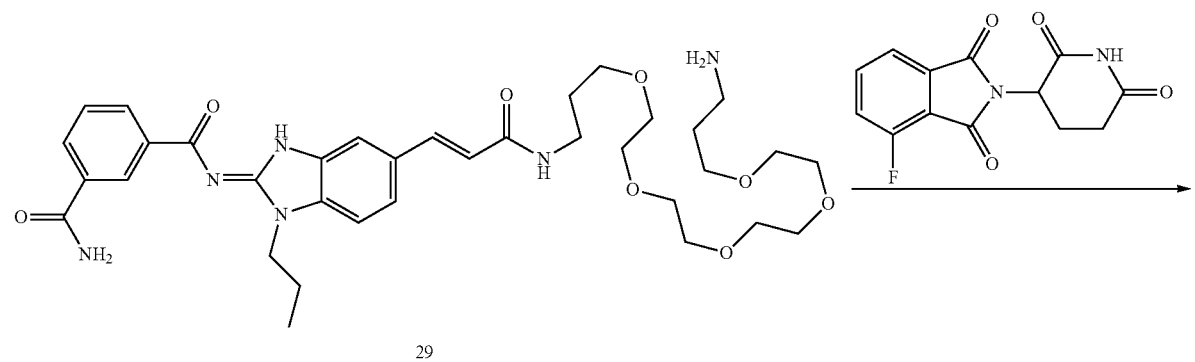

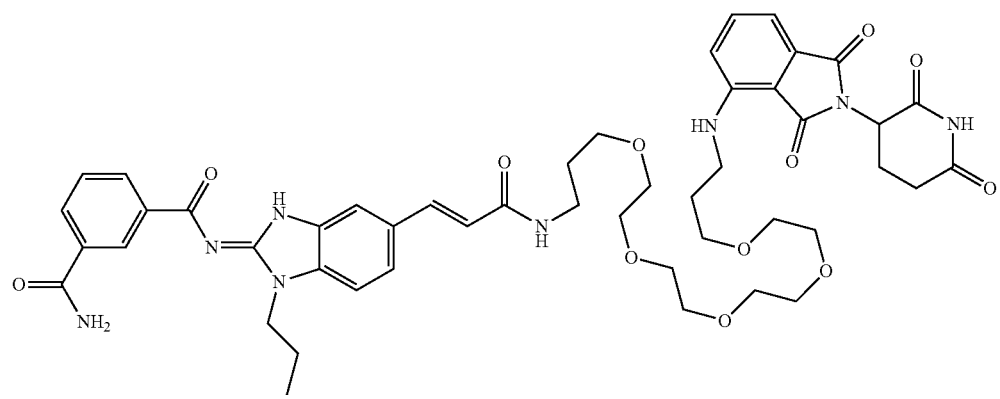

30

HS-237.

From Chem Biol. 2015 Jun. 18; 22(6): 755-763. Amine 29, (33 mg, 48 µmol) and the ProTac precursor (Advanced Chemblocks, M23273, 2-(2,6-Dioxo-piperidin-3-yl)-4-fluoroisoindoline-1,3-dione CAS #835616-60-9, 14 mg, 51 µmol) were slurried in DMF (500 µL), treated with Hunig's base (13 mg, 97 µmol) and heated to 90° C. for 18 h. The reaction mixture was loaded onto a column and chromatographed (50 g isco C-18, 0.2% formic in water to 100% MeOH) to give the desired product 30 (7.7 mg, 17%) as a yellow solid. Substantial reaction of 29 with DMF to form a formamide was seen. LC/MS of 30 gave a single peak with m/z=939.2 for [M+H]$^+$. $^1$H-NMR (dmso-d$_6$) δ 8.68 (s, 1H), 8.37 (d, J=8 Hz, 1H) 8.13 (br t, J=6 Hz, 1H) 8.10 (br s, 1H), 7.99 (d, J=8 Hz, 1H), 7.71 (s, 1H), 7.53-7.60 (m, 3H), 7.47 (d, J=16 Hz, 1H), 7.47 (t, J=8 Hz, 1H), 7.42 (br s, 1H), 7.09 (d, J=8 Hz, 1H), 7.01 (d, J=8 Hz, 1H), 6.65 (br t, J=6 Hz, 1H), 6.55 (d, J=16 Hz, 1H), 5.04 (dd, J=5, 13 Hz, 1H), 4.26 (t, J=7 Hz, 2H), 3.46-3.59 (m, 20H), 3.44 (m, 2H), 3.22 (q, J=6 Hz, 2H), 2.88 (m, 1H), 2.45-2.63 (m, 4H), 2.02 (m. 1H), 1.77-1.90 (m, 4H), 1.70 (p, J=7 Hz, 2H), 0.93 (t, J=7 Hz, 3H).

Additional Takinib Analogs

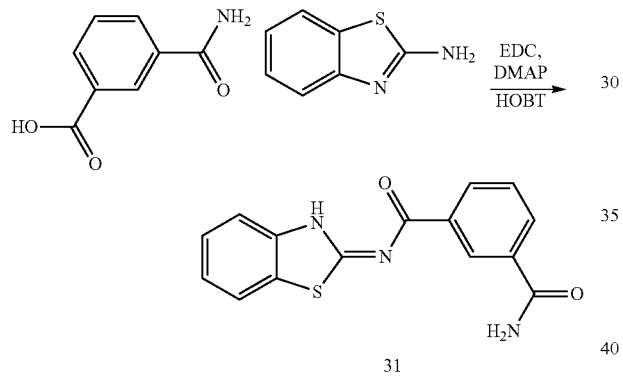

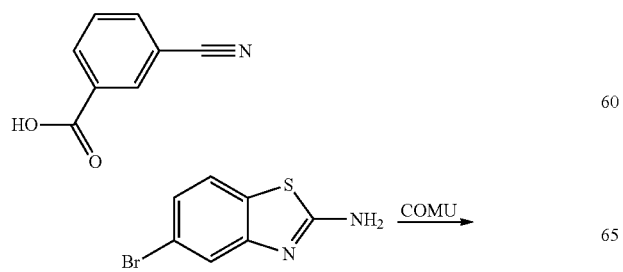

HS-230.

3-Carbamoylbenzoic acid (100 mg, 605 µmol), 2-aminobenzothiazole (91 mg, 605 µmol), EDC (174 mg, 908 µmol), HOBT (93 mg, 605 µmol) and DMAP (7 mg, 60 µmol) were combined in methylene chloride (2 mL) and treated with Hunig's base (78 mg, 605 µmol) and stirred at RT. After a few minutes, DMF (1 mL) was added to aid dissolution. After 4 h, the reaction was diluted with methanol and the solid precipitate filtered off and air dried to give amide 31 (148 mg, 82%) as a white powder. LC/MS showed a very broad peak with m/z=298.0, [M+H]$^+$ and 617.1, [2M+Na]$^+$.

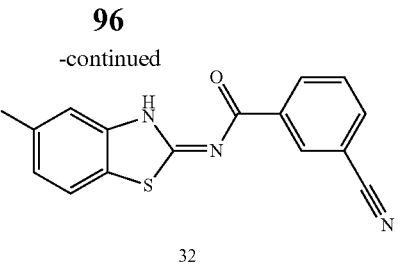

32

COMU (306 mg, 714 µmol) and 3-cyanobenzoic acid (100 mg, 680 µmol) were dissolved in DMF (1 mL) and treated with Hunig's base (88 mg, 680 µmol). A lot of stuff fell out. After 5 m, 2-amino-5-bromobenzothiazole (156 mg, 680 µmol) was added along with more DMF (1 mL) and the mixture was stirred for 18 h. The mixture was treated with a little ethanol (2 mL) and heated to clarity, then diluted with water (20 mL) which caused a lot of white solid to form. This was stirred vigorously for 2 hours then filtered and washed with water and air-dried to give nitrile 32 (243.9 mg, 100+%) as a white solid. LC/MS gave a major peak with m/z=357.9 and 359.9 for [M+H]$^+$. There were 2 additional minor peaks in the UV trace. The material was used for the next step.

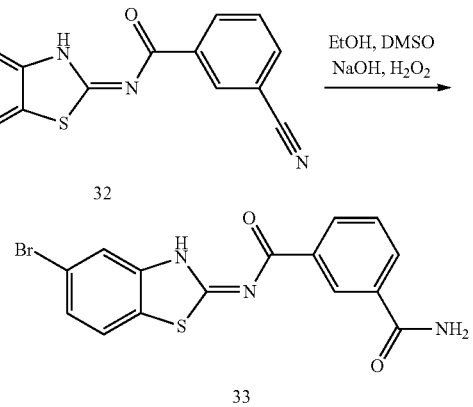

HS-232.

Nitrile 32 (50 mg, 140 µmol) was dissolved in DMSO (100 µL) and diluted with ethanol (2 mL). This was then treated with 50% NaOH (5 drops). The mixture was stirred for 2 h, then treated with acetic acid (50 µL), then ethanol (2 ml), then water (2 mL). The mixture was stirred overnight. The next day, the solids were filtered off and air-dried to give the amide product 33 (41 mg, 78%) as a white powder. LC/MS shows a small single peak and a trailing m/z=376.0 and 378.0 for [M+H]$^+$.

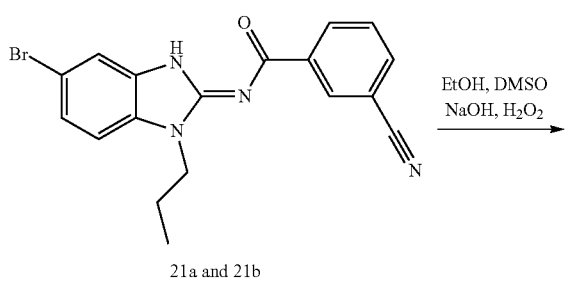

21a and 21b

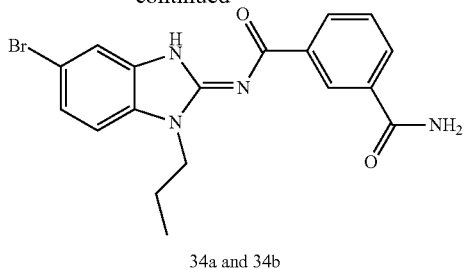

34a and 34b

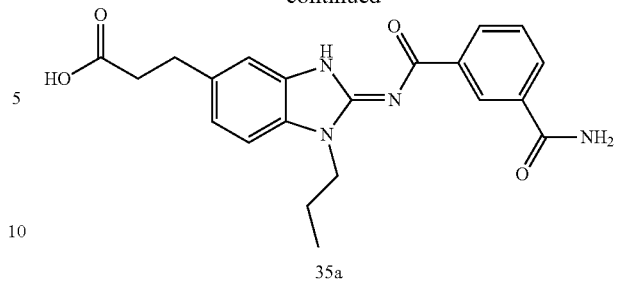

35a

HS-231.

A mixture of nitriles 21a and 21b (22 mg, 57 µmol) was dissolved in DMSO (350 µL) and diluted with ethanol (500 µL). This was then treated with 50% NaOH (2 drops) followed by 30% hydrogen peroxide (3 drops). Lots of stuff fell out of solution. LC/MS of the crude material gave m/z=401.1 and 403.1 for [M+H]$^+$. After stirring for 1 h, the mixture was transferred and concentrated onto silica gel (1 g) and chromatographed (12 g isco silica gel, 0 to 10% MeOH in CH$_2$Cl$_2$) to give product which was slurried in MeOH to give a white crystalline solid. This was filtered off and air dried to give amides 34a and 34b (15.5 mg, 67%) as a white solid.

HS-238.

Acid 23a (40 mg, 102 µmol) was slurried in ethanol (1 mL) and 10% Pd/C (5 mg) in EtOH (1 mL) and put under H$_2$ atmosphere with 3 vacuum flushes. After a week, LC/MS showed some progress. Acetic acid (1 mL) and more catalyst were added and the reaction was mistakenly heated to reflux. LC/MS showed clean formation of product m/z=395.1 and no sign of starting material. The reaction mixture, which contained substantial precipitate, was stirred under nitrogen overnight, then diluted with DMSO (to dissolve product, 2 mL) and filtered through Celite®, concentrated and chromatographed (50 g isco C-18, 0.2% formic in water to 100% MeOH) to give product in approx. 4/1:methanol/water. Crystals formed in the fractions and were filtered off to give the saturated acid 35a (18.2 mg, 45%) as a white solid. LC/MS gave a single peak with m/z=395.2 for [M+H]$^+$.
$^1$H-NMR (dmso-d$_6$) δ 8.67 (s, 1H), 8.37 (d, J=8 Hz, 1H), 8.09 (br s, 1H), 7.98 (d, J=8 Hz, 1H), 7.53 (t, J=8 Hz, 1H), 7.44 (d, J=8 Hz, 1H), 7.41 (br s, 1H), 7.40 (s, 1H), 7.14 (d, J=8 Hz, 1H), 4.24 (t, J=7 Hz, 2H), 2.90 (t, J=7 Hz, 2H), 2.55 (t, J=7 Hz, 1H), 1.83 (hx, J=7 Hz, 2H), 0.92 (t, J=7 Hz, 3H).

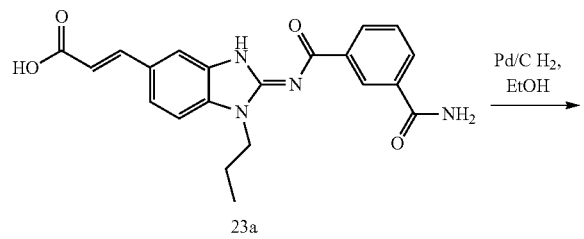

23a

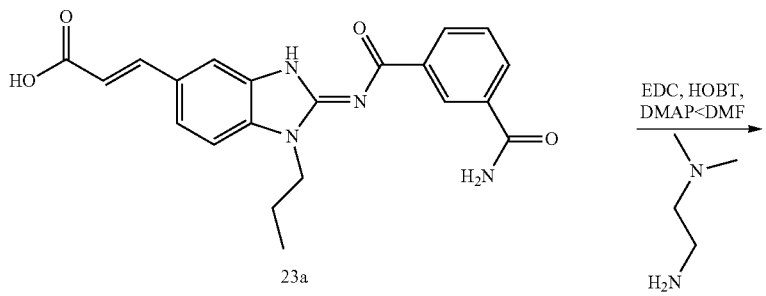

23a

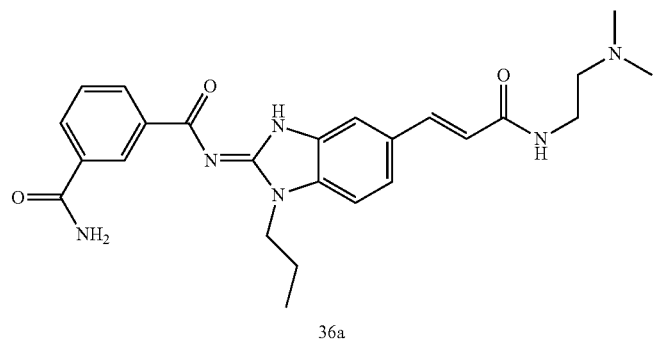

36a

HS-242.

Acid 23a (100 mg, 0.25 μmol) was mixed with HOBT (34 mg, 0.25 μmol), DMAP (12 mg) and EDC (107 mg, 0.56 μmol) then slurried in DMF (1 mL). Diamine (90 mg, 1 mmol) was added and the mixture sonicated to dissolve everything. After one day, the entire reaction mixture was added to a column and chromatographed (50 g isco C-18, 0.2% formic in water to 100% MeOH) to 36a (41 mg, 35%) as an off-white solid. LC/MS gave a single peak with m/z=463.2 for [M+H]$^+$. $^1$H-NMR (dmso-d$_6$) δ 12.81 (br s, 1H), 8.68 (s, 1H), 8.38 (d, J=8 Hz, 1H), 8.20 (s, formate, 1H), 8.11-8.14 (m, 2H), 8.00 (d, J=8 Hz, 1H0, 7.72 (s, 1H), 7.58 (d, j=8 Hz, 1H), 7.55 (t, J=8 Hz, 1H), 7.47 (d, J=16 Hz, 1H), 7.47 (d, J=8 Hz, 1H), 7.44 (br s, 1H), 6.62 (d, J=16 Hz, 1H), 4.27 (t, J=7 Hz, 2H), 3.30 (q, J=7 Hz, 2H), 2.39 (t, J=7 Hz, 2H), 2.20 (s, 6H), 1.85 (hx, J=7 Hz, 2H), 0.93 (t, J=7 Hz, 3H).

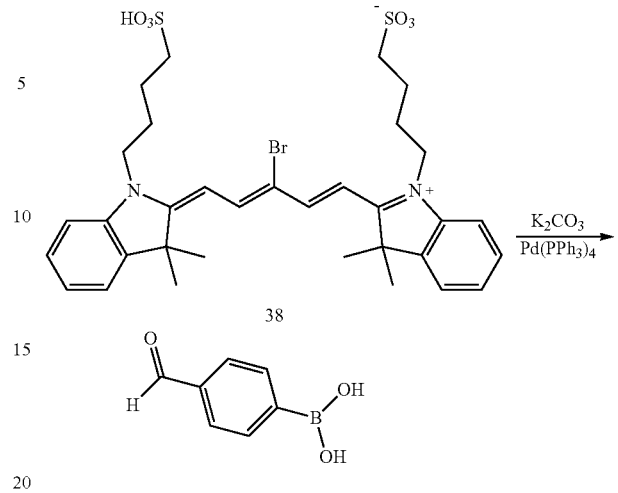

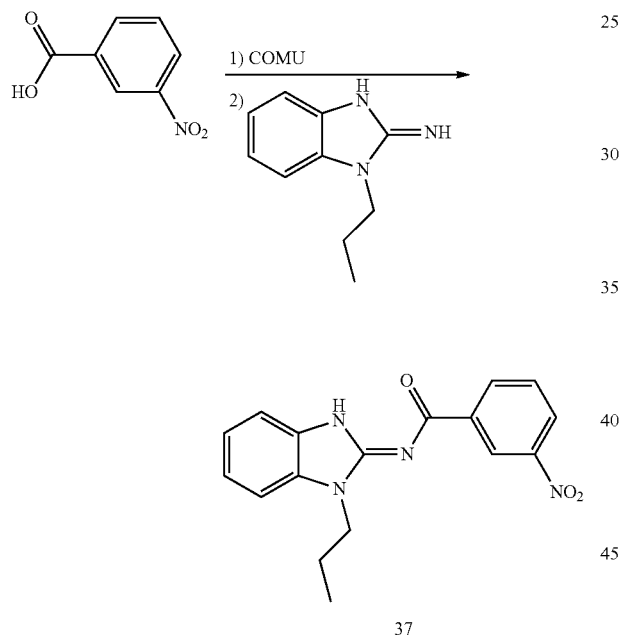

37

HS-243.

COMU (270 mg, 629 mmol) and 3-nitrobenzoic acid (100 mg, 599 mmol) were combined in DMF (1 mL) and treated with Hunig's base (209 mL) followed by 1-propyl-2-aminobenzimidazole (105 mg, 599 mmol) in DMF (1 mL). After 1 h, the reaction mixture was added to a column and chromatographed (50 g isco C-18, 0.2% formic in water to 100% MeOH) to 37 (72 mg, 37%) as a light yellow fluffy solid. LC/MS gave a single peak with m/z=325.1 for [M+H]$^+$. $^1$H-NMR (dmso-d$_6$) δ 8.95 (s, 1H), 8.64 (d, J=8 Hz, 1H), 8.38 (d, J=8 Hz, 1H), 7.79 (t, J=8 Hz, 1H) 7.58 (d, J=8 Hz, 1H), 7.57 (d, J=8 Hz, 1H), 7.28 (t, J=8 Hz, 1H), 7.25 (t, J=8 Hz, 1H), 4.28 (t, J=7 Hz, 2H), 1.86 (hex, J=7 Hz, 2H), 0.95 (t, J=7 Hz, 3H).

The dye 38 (300 mg, 425 mmol) and 4-formylphenyboronic acid (64 mg. 425 mmol) along with Pd(0)(PPh$_3$)$_4$ (49 mg, 42.5 mmol) and potassium carbonate (117 mg, 850 mmol) were dissolved in water/dioxane (5 mL ea.). The mixture was bubbled with N$_2$ for 30 m and then heated at 100 C for 1 h. TLC (4/0.9/0.1:CH$_2$Cl$_2$/MeOH/NH$_4$OH, 3 times) showed clean formation of a new product. The mixture was concentrated, dissolved in DMSO/water and loaded onto a column and chromatographed (130 g isco C18 column, 0 to 100% MeOH in water, both with 0.2% formic acid.) to give 39 (236 mg, 76%) as a crunchy bronze blue solid. $^1$H-NMR (dmso-d$_6$) d 10.08 (s, 1H), 8.48 (d, J=14 Hz, 2H) 8.17 (d, J=7 Hz, 2H), 7.65 (d, J=7 Hz, 2H) 7.58 (d, J=7 Hz, 2H), 7.42 (d, J=7 Hz, 2H), 7.38 (t, J=7 Hz, 2H), 7.26 (t, J=7 Hz, 2H), 5.69 (d, J=14 Hz, 2H), 3.78 (t, J=7 Hz, 4H), 2.38 (t, J=7 Hz, 4H), 1.76 (s, 12H), 1.64 (m, 4H), 1.49 (m, 4H).

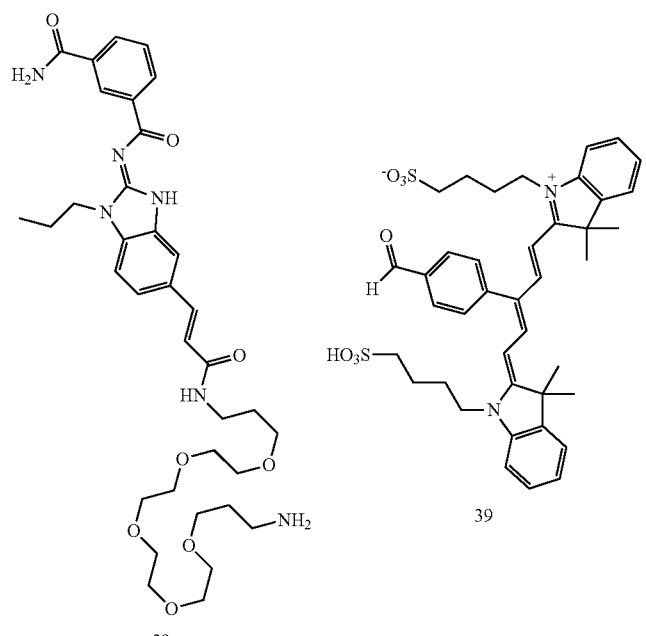

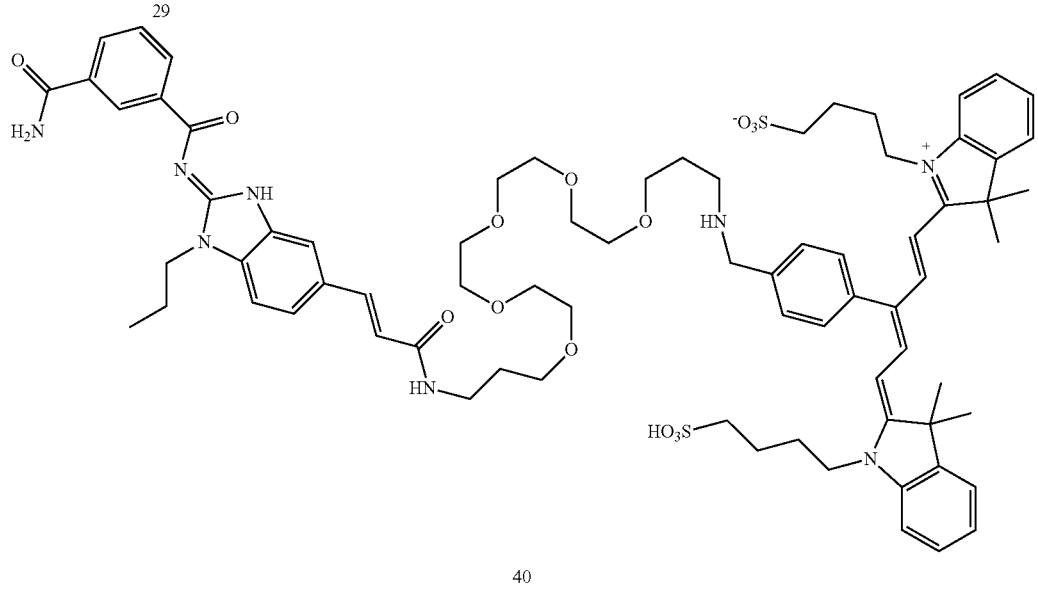

HS-241.

The dye 39 (53 mg, 72 μmol) and amine 29 (49 mg. 72 μmol) were dissolved in methylene chloride (2 mL) and treated with acetic acid (34 mg) and stirred at RT for 30 m. Sodium triacetoxy borohydride (65 mg, 0.3 μmol) was added in three portions over 1 day. The reaction mixture was treated with methanol (2 mL) and concentrated. The residue was added to a column and chromatographed (50 g isco C-18, 0.2% formic in water to 100% MeOH) to 40 (10 mg, 10%) as a blue solid. LC/MS gave a major peak with m/z=1397.3 [M+H]$^+$ and 699.3 [M+2H]$^{2+}$.

Compound 40 may have use as a fluorescent dye to reversibly label TAK1 in vivo or in vitro. Thus, compound 40 may have use to track TAK1 in a cell under a microscope and determine its location in a cell. It may also be useful to aid in isolating the protein from some mixture by following fluorescence.

Reference Example 1

Materials.

HEK293 and HepG2 cells were obtained from the Duke Cell Culture Facility. Cells were cultured in Dulbecco's modified Eagle's medium (DMEM) (Life Technologies) supplemented with 10% FBS (Sigma) and 1% antibiotic-antimycotic (Life Technologies) and maintained in a standard tissue culture incubator (37° C., 5% $CO_2$). ATP-sepharose beads were synthesized in house according to a previously published procedure. *Plasmodium berghei* ANKA infected *Anopheles stephensi* mosquitoes were purchased from the New York University Langone Medical Center Insectary.

Primary Small-Molecule Screen.

A small-molecule screen was performed similar to a previously reported fluorescence linked enzyme chemoproteomic strategy (FLECS). Briefly, HEK293-GFP-PfPK9 cells were grown in 182-cm² tissue culture flasks (Genesee Scientific) and harvested at ~80% cell confluency. Before assays the culture medium was aspirated, cells were rinsed with ice cold PBS and then they were removed with a cell scraper. Cells were pelleted by centrifugation (2,000 rpm, 4° C., 2 min) and immediately lysed for assays. The pellet was suspended in buffer A (25 mM HEPES, pH 7.4, 150 mM NaCl, 60 mM $MgCl_2$, 1 mM DTT) with 1 µM microcystin, 0.1% Triton X-100 plus a Roche Complete protease inhibitor tablet and then placed on ice for 30 min to facilitate lysis. The supernatant was collected after centrifugation (4,300 rpm, 4° C., 5 min) and used in subsequent screening and titrations experiments. For screening, the supernatant was added to ATP-sepharose beads (1:1) and incubated with agitation at 4° C. for at least 1 hr to allow binding. Following this incubation, the mixture was centrifuged, the ATP resin was washed with 9 column volumes of buffer A with 1 M NaCl and then 9 column volumes of buffer A. The ATP-sepharose medium was reconstituted as a 1:1 slurry with buffer A and then added to 96-well filter plates (50 µL/well) (Corning #3505) using a multichannel pipette (Rainin). The filter plate was on top of black 96-well catch plates (Corning #3915). An ATP dilution series (1-200 mM) was added to each plate as a positive control and DMSO was the negative control. Compounds and controls were all added to 50 µL per well in buffer A. For screening, compounds were tested in singlicate at 500 µM. The final DMSO concentration in every well was 5%. The fluorescence intensity in each well was measured on an EnVision system. Data analyses of screens were carried out in EXCEL (Microsoft, Corp.) and actives were identified as 2×background signal.

Secondary Assays.

All screening positives were verified with Western blot analysis. SDS gel loading buffer was added to filtrates after fluorescence measurement, samples were loaded onto 4-20% Tris-Glycine polyacrylamide gels (Novex, Life Technologies) and then wet-transferred to nitrocellulose membranes. Membranes were blocked with 3% BSA and then probed with primary rabbit eGFP antibodies (CAB4211, Pierce) and secondary Alexa Fluor 488® goat anti-rabbit IgG antibodies (A-11034, Life Technologies). Precision Plus Protein™ (Bio-Rad) was used as a protein ladder and the blots were imaged using Image Lab Software (Bio-Rad).

All screening positives that were verified with Western blot analysis were purchased from Enamine or Vitas-M laboratory. The purity of compounds 1-5 (shown below) was verified by high-resolution MS (Agilent). Compounds were tested in 8-point dose-response (0-500 µM) experiments in duplicate, essential as described above. The fluorescence intensity in each well was measured using an EnVision system. Dose-response analysis was performed with GraphPad Prism to acquire $EC_{50}$ values. Determined $EC_{50}$ values were used to calculate the observed PfPK9 $K_d$ and reported values are the average of 2-3 independent experiments.

Cell-Based Anti-*Plasmodium* Assays.

For liver stage assays, 15,000 HepG2 or 8,000 Huh7 cells/well were added to 384-well microtiter plates using a multichannel pipette (Rainin). After 2 hours at 37° C., compounds (0-100 µM) were added to cells in duplicate or triplicate in a final concentration of 1% DMSO. DMSO was used as the negative control. Following compound incubation at 37° C. for ~1 hr, harvested luciferase-expressing *P. berghei* ANKA sporozoites were added to the plates at a density of 3,000 sporozoites/well. *P. berghei* ANKA sporozoites were obtained from harvesting the salivary glands of infected *A. stephensi* mosquitoes. The plates were spun for 10 min at 1,000 rpm, and then incubated at 37° C. for ~45 hrs. The final assay volume post-infection was 30 µL and all wells had a final concentration of 1% DMSO. After ~45 hours at 37° C., liver cell viability was assessed using CellTiter-Fluor (Promega) and then parasite load was determined using Bright-Glo (Promega). The relative fluorescence and luminescence signal intensity of each well was evaluated with an EnVision System. The luminescence signal in the presence of compounds was normalized to the negative control (DMSO). Dose-response analysis was performed with GraphPad Prism to yield the reported $EC_{50}$ values.

Stable Cell Line Generation.

The *P. falciparum* PK9 gene (PlasmoDB accession #PF3D7_1315100) was cloned into the pEGFP-C1 mammalian expression vector (Clontech) in frame with a C-terminal GFP tag. For screening, HEK293 cells were transfected with the resulting PfPK9-pEGFP-C1 vector to generate HEK293-GFP-PfPK9 expressing cells using X-tremeGENE HP transfection reagent (Roche) per the manufacturer instructions. Briefly, the culture medium was replaced at 48 hours post-transfection with medium supplemented with 1 mg/mL G418 sulfate (Life Technologies) to select for stably transfected cells. Following stable cell selection, fluorescence activated cell sorting (FACS) was used to enrich for GFP-PfPK9 expressing cells. Subsequently, FACS sorted HEK293-GFP-PfPK9 cells were cultured with medium supplemented with 0.5 mg/mL G418 sulfate for all following experiments. Protein expression was verified by Western blot analysis probing for anti-GFP and by fluorescence intensity using an EnVision (PerkinElmer) system.

Recombinant Protein Expression and Enzyme Activity Assay.

Recombinant GST-tagged PfPK9 was expressed in *E. coli* BL21(DE3) cells, purified to homogeneity, and the GST tag was cleaved with PreScission Protease (GE Healthcare). To test for inhibition of PfPK9, the ADP detection assay ADP-Glo (Promega) was used to determine ATPase activity of PfPK9 in the presence of the PfUBC13 protein substrate when treated with compounds 1 and 5. Approximately 500 nM PfPK9 was incubated with either compound (10 µM or 500 µM) for 5 min at RT in buffer containing 40 mM Tris, pH 7.5, 20 mM $MgCl_2$, 2 mM $MnCl_2$ and 1 mM DTT prior to assay initiation with 100 µM ATP. The assay was performed in white low-volume 384-well plates (Corning #3824) in triplicate. The assay plate was sealed and subsequently incubated for 8 hrs at 37° C. before ADP detection per manufacturer instructions. The final assay volume was 5 µL with a final concentration of 1% DMSO. A negative control was performed in 1% DMSO and heat inactivated PfPK9 (80° C. for 5 min) was used as a positive control. The luminescence intensity in each well was measured on an EnVision system. Data were normalized to the average luminescence signal of the negative control to provide relative ADP concentrations and graphs were constructed in GraphPad Prism. Data analyses were conducted from three independent experiments. An unpaired two-tailed t-test was used to determine statistical differences between control and sample reactions.

Gene Expression Analysis.

For gene expression of PbPK9 during the liver stage, HepG2 cells were seeded in a 12-well plate (Costar #3513) and infected with *P. berghei* ANKA sporozoites at 0.3 multiplicity of infection. At four hours post-infection, the culture medium was changed with fresh medium to control for non-invading sporozoites. Thereafter, the total RNA was isolated or the plate further incubated at 37° C. until sample collection. Total RNA was isolated from HepG2 cells at 4, 24 and 48 hours post-infection and from $1\times10^5$ sporozoites used for infection. First strand cDNA was synthesized from total RNA (20 ng) with random hexamers and GoScript™ Reverse Transcription System according to manufacturer protocol (Promega). Quantitative real-time PCR (qPCR) was performed using cDNA as a template, gene-specific primers, and SYBR green I Master Mix (Roche) on a LightCycler® 480 System (Roche). The relative PbPK9 mRNA levels were normalized against the levels of Pb 18S rRNA and firefly luciferase (luc) used as reference genes. The relative gene expression of PbPK9 over time in infected cells was compared to P. berghei ANKA sporozoites (reference time point). Data analyses were performed from four biological experiments. PCR amplification was performed as follows: 10 minutes at 95° C. followed by 45 cycles of three-step amplification of 95° C. for 10 s, 53° C. (60° C. for firefly luciferase primers) for 20 s and 72° C. for 10 s. The primer sequences used for qPCR were as follows: PbPK9, AATTATGGGCCGCTTATTGG (SEQ ID NO: 1), TGACTCAAGGTTACCCACCA (SEQ ID NO: 2); Pb 18S rRNA, GGTTTTGACGTTTATGTGGGCAT (SEQ ID NO: 3), GGCATGTCGTAAACGCAAGAA (SEQ ID NO: 4); firefly luciferase (luc gene), CGGGCGCGGTCGGTAAAGTT (SEQ ID NO: 5), GTCGGGAAGACCTGCCACGC (SEQ ID NO: 6).

Immunofluorescence Analysis of EEFs.

For immunofluorescence analysis of EEFs, Huh7 cells were fixed with 4% paraformaldehyde for 10 min at room temperature (RT), washed thrice with PBS, permeabilized with cooled methanol for 10 min at −20° C. and blocked with 3% BSA in PBS for 30 min at RT. Thereafter, cells were incubated with a primary antibody, mouse anti-PbHSP70 (clone 2E6; 1:1000) diluted in blocking buffer overnight at 4° C. Following incubation, samples were washed with PBS and incubated for 1 hr at RT with a secondary antibody, goat anti-mouse AlexaFluor 488 (1:400, Life Technologies). Finally, nuclei were stained with DAPI for 15 min at RT. For evaluation of fluorescence intensity from EEFs after infection with GFP-expressing P. berghei sporozoites, DAPI nucleus staining was performed following cell fixation. After five washes with PBS, ~40 µl PBS was left in wells and images were acquired on a Zeiss Axio Observer widefield fluorescence microscope.

P. falciparum Asexual Blood-Stage Culture.

P. falciparum 3D7 isolate was maintained under standard conditions in complete culturing medium [10.44 g/L RPMI 1640 (Invitrogen), 5.94 g/L HEPES (Invitrogen), 50 mg/L hypoxanthine (Sigma), 2.02 g/L sodium bicarbonate (Sigma), 5 g/L albuMAX II (Invitrogen), 25 mg/L gentamicin (Sigma), pH 7.2]. Parasite cultures were supplied with human red blood cells (Gulf Coast Regional Blood Center) at 1% hematocrit. To obtain synchronous cultures, Plasmodium parasites (at least 50% parasites were at the early-ring stage) were pelleted at 300×g for 7 min using a low brake setting and treated with 25 volume 5% D-sorbitol (Sigma) at 37° C. for 10 min. Treated parasites were then harvested and washed with 25 volume of complete culturing medium using the aforementioned centrifugation protocol, and diluted with the complete medium to 1% hematocrit to maintain the parasite culture at 37° C. and 5% $CO_2$.

Protein Extraction and Western Blot for K63-Linked Ubiquitination in Plasmodium Blood Stage.

Synchronized ring-stage P. falciparum parasites (10 h post-reinvasion) at 10% parasitemia, 1% hematocrit were exposed for 24 hr with either compound 1 (6 points dose-response; 0.001-100 µM), compound 5 (single concentration; 30 µM) or ≤0.1% DMSO. Following compound exposure, P. falciparum cultures were harvested and sequentially treated with 0.03% saponin lysis buffer to remove host cytosolic proteins and uninfected red blood cells followed by sonication in parasite lysis buffer [10 mM HEPES pH 7.4, 150 mM NaCl, 1 mM EDTA, 0.25% Triton X-100, 0.1% 2-Mercaptoethanol, 1 mM Benzamidine, Complete protease inhibitor cocktail]. Total protein lysates were heated in SDS loading buffer for 5 min at 80° C., analyzed on 4-20% Tris-Glycine polyacrylamide gels (Novex, Life Technologies) and subsequently transferred to nitrocellulose membranes. A ubiquitin antibody specific for K63 linkages (Abcam ab179434) was used to probe changes in protein ubiquitination between control and treated samples. Anti-actin antibody (Abcam ab3280) was used to monitor actin levels as a loading control. Antibody-bound proteins were visualized using the BioRad ChemiDoc MP imager.

Example 4. Compounds Tested

| Cmpd | Structure | $K_{d,\ app}$ (µM) | IC$_{50}$ (µM) Liver stage (HepG2) | IC$_{50}$ (µM) Liver stage (Huh7) |
|---|---|---|---|---|
| HS-206 (1) | 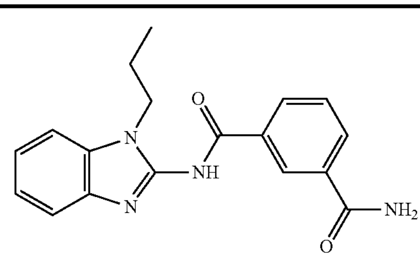 | 0.2 | 6.6 (5.6-7.8) | 7.3 (6.4-8.4) |

-continued

| Cmpd | Structure | $K_{d, app}$ (µM) | IC$_{50}$ (µM) Liver stage (HepG2) | IC$_{50}$ (µM) Liver stage (Huh7) |
|---|---|---|---|---|
| 2 | (structure) | 7.0 | 4.5 (2.6-7.9) | 0.090 (0.01-0.6) |
| 3 | (structure) | 0.6 | 7.3 (4.2-13) | 4.0 (3.9-4.2) |
| 4 | (structure) | 3.2 | 54.5 (44-68) | 33.3 (15-74) |
| 5 | (structure) | ND$^a$ | 9.7 (7.6-12) | 8.5 (7.3-10) |

Example 5. Cell-Based Anti-*Plasmodium* Assays

Anti-*Plasmodium* activity was evaluated in the parasite's liver stage using a previously reported high-throughput assay. In this assay, luciferase-expressing *P. berghei* (murine) parasites are used to infect human hepatoma cells (HepG2) and parasite load is assessed with a luminometer subsequent to evaluating HepG2 viability using a commercially available quantification kit that measures intracellular protease activity. Among the 14 compounds tested none inhibited HepG2 viability ≥50% at 30 µM, indicating relatively low cytotoxicity, but five compounds reduced parasite load ≥50% (FIG. 2A). These compounds termed 1-5 were selected for further analyses.

Example 6. Recombinant Protein Expression and Enzyme Activity Assay

All 14 positive molecules were also tested for their binding affinity to PfPK9 using an optimized ATP-competitive binding assay. EC$_{50}$ values ranging from low µM to low mM were observed and these EC$_{50}$ values were used to derive dissociation constants as described previously. Among the compounds exhibiting anti-*Plasmodium* activity, benzimidazole compound 1 exhibited the highest binding affinity for GFP-PfPK9 with an apparent K$_d$ (K$_{d(app)}$) of ~0.2 µM (FIG. 2B), while compound 2 exhibited the lowest binding affinity with an apparent K$_d$ ~7 µM. To enable comparisons of these binding constants to PfPK9's native substrate, the apparent K$_d$ of ATP for GFP-PfPK9 (~0.4 mM, was determined. Compounds 1, 2 and 3 are structural analogs containing a benzimidazole scaffold whereas compounds 4 and 5 contain a quinoline scaffold (FIG. 2C).

The potency of compounds 1-5 was evaluated in several cell-based assays. Specifically, their ability to inhibit *P. berghei* infection in two human hepatoma cell lines (HepG2 and Huh7) as well as cytotoxicity against HepG2 and Huh7 cells was determined as described above. Liver cell cytotoxicity was evaluated with two different commercially available assays, one that tests for intracellular protease activity with a fluorescence reporter and another that relies on the luminescent detection of total ATP. Compounds 1-3, which share a benzimidazole scaffold, inhibited liver stage parasites with $IC_{50}$ values in the low micromolar range (5-7 M) and with similar potencies regardless of the host cell line tested. Compound 1 exhibited an $IC_{50}$ value of ~7 µM against parasite infection in both HepG2 and Huh7 yet did not affect liver cell viability even at 200 µM based on three independent cytotoxicity assays (FIG. 3A). Despite a weak binding affinity for PfPK9 ($K_{d(app)}$=7 µM), compound 2 showed the highest inhibition of parasite load in liver cells with $IC_{50}$ values of 4.5 µM and 0.09 µM in HepG2 and Huh7 cells, respectively. However, assessment of cell viability revealed a significant cytotoxic effect of compound 2 at 30 µM in both hepatoma cell lines (ANOVA P=0.0050 for HepG2 and ANOVA P=0.0060 for Huh7) when compared to the DMSO control. Compound 3 ($K_{d(app)}$=0.6 µM) inhibited parasite load with $IC_{50}$ values of 7.3 µM and 4.0 µM in HepG2 and Huh7 cells, respectively, and showed moderate cytotoxicity in HepG2 cells (ANOVA P=0.0050). Compound 4, a 4-aminoquinoline derivative, had weak inhibitory activity on parasite load with $IC_{50}$ values of 55 µM and 33 µM, respectively in HepG2 and Huh7 cells. The 8-aminoquinoline derivative compound 5, whose affinity for PfPK9 was not determined using fluorescent readout, exhibited parasite inhibition $IC_{50}$ values of 9 µM and 10 µM, respectively, in Huh7 and HepG2 cells. In contrast to the benzimidazole structural analogs, neither compound 4 or 5 had any significant effects on cell viability at concentrations up to 200 µM.

Example 7. Gene Expression During *Plasmodium* Liver Stage

To probe the biological function of PfPK9 in *Plasmodium*, the gene expression profile of the murine *P. berghei* protein kinase 9, PbPK9, was measured throughout liver stage development. *P. berghei*-infected HepG2 cells were collected at various times post-infection (4-48 hr) and extracted total RNA was analyzed with quantitative real-time PCR using primers for PbPK9, Pb18S rRNA and luc (firefly luciferase) genes. Freshly dissected parasites (sporozoites) that were not used for infection were used to normalize samples collected at 4, 24 and 48 hours post-infection. Samples at each time were also normalized to Pb18S rRNA and luc to control for parasite numbers. As shown in FIG. 3B, PbPK9 is expressed throughout *Plasmodium* liver stage development and exhibits a time dependent increase post-infection. PbPK9 levels are greatest in the exo-erythrocytic form (EEF) that was evaluated at 48 hours post-infection (ANOVA P=0.0154) when compared to four hours post-infection. Since a single *Plasmodium* parasite develops into 10,000-30,000 over the course of liver stage infection, the transcript levels of Pb18S rRNA and luc genes were also evaluated as markers that would be proportional to parasite numbers. These markers exhibited a time dependent decrease in Ct values post-infection (ANOVA P=0.0012 and ANOVA P<0.0001, respectively for Pb18S rRNA and luc genes), suggesting proper maturation and division of parasites during the experiment.

Example 8. Inhibition of PfPK9 Autophosphorylation In Vitro

PfPK9 activity in the presence of the compounds was also evaluated. PfPK9 requires autophosphorylation at threonine residues (T082, T265, and T269) for optimal kinase activity and this requirement was exploited for our assay design. Purified recombinant PfPK9 was used and measured the generation of ADP from ATP in the presence and absence of compounds 1 and 5 using a commercially available luminescence assay. As shown in FIG. 3C, compound 1 significantly reduced the generation of ADP by approximately 40% at 500 µM (P=0.002), but not 10 µM. Compound 5, which has a quinoline scaffold, reduced PfPK9 activity by approximately 70% and 30% at 500 µM and 10 µM, respectively (P=0.0007 and 0.009, respectively).

Example 9. Effect of HS-206 During Malaria's Liver Stage

Figure 10:
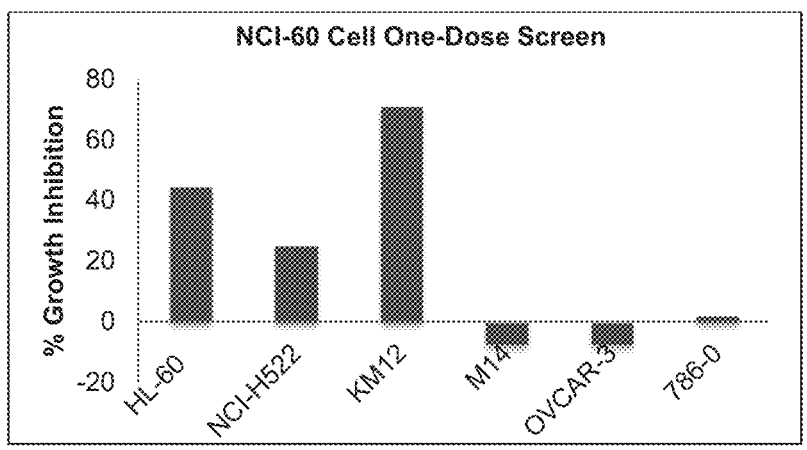
FIG. 10 shows results of NCI-60 Cell One-Dose Screen.

To further investigate the effect of compound 1 during malaria's liver stage, immunofluorescence assays were performed. Infected Huh7 cells were treated with 10 µM or 30 µM compound 1 for various period of time ranging from 0-24 h post-infection (hpi), 24-48 hpi and 0-48 hpi, and subsequently labeled with *P. berghei* HSP70 antibodies at 48 hpi. As shown in FIGS. 4A and 4E, 10 µM compound 1 treatment significantly increased P. b. EEF size as compared to DMSO treated cells at all time periods tested (One-way ANOVA P<0.0001). The number of P.b. EEFs was not affected by 10 µM compound 1 as compared to DMSO treatment (FIG. 4B; One-way ANOVA P=0.0804). Similarly, treatment of infected cells with 30 µM compound 1 led to increased P.b. EEF size when added either for 0-24 hpi or 24-48 hpi. (FIGS. 4C and 4E; One-way ANOVA P<0.0001). Interestingly, the number of P. b. EEFs only decreased when compound 1 was added for 0-24 hpi or 0-48 hpi whereas treatment from 24-48 hpi did not significantly decreased EEF number (FIG. 4D; One-way ANOVA P<0.0001). Moreover, total fluorescence signal from GFP-expressing P.b. EEFs decreased with compound 1 when added for a period of 48 h post-infection. Specifically, a decreasing trend in fluorescence signal was observed with 10 µM compound 1, which was further exacerbated by a higher concentration of 30 µM post-infection; whereas P.b. EEF size was increased by 10 µM compound 1 as compared to DMSO treated cells. These observations suggest that compound 1 while potentially modulating parasite growth during infection has a detrimental effect on parasite viability.

Example 10. PfPK9 Inhibitors Decrease K63-Linked Protein Ubiquitination In Vivo Given that the *P. falciparum* E2 ubiquitin-conjugating enzyme (PfUBC13), which is involved in K63-linked ubiquitination, was shown previously to be regulated by PfPK9[13], it was investigated whethere compound 1 would affect its ubiquitin-conjugating activity. Hence, ring-form blood stage *P. falciparum* parasites were treated for 24 hrs with increasing concentrations of compound 1 and anti-UbK63 was used to assess levels of K63-linked ubiquitination in total parasite protein extracts. A dose-dependent decrease was observed in the levels of K63-linked ubiquitinated proteins after compound 1 treatment compared to DMSO treated blood stage parasites (FIG. 5A-B). Similarly, compound 5 (30 µM) also decreased K63-linked ubiquitination in blood stage parasites albeit to a lesser extent than compound 1.

Lastly, to ensure that our in vivo results were primarily due to PfPK9 inhibition, the effect of compounds 1 and 5 on UBC13 phosphorylation in vitro was investigated. Using a commercially available luminescence assay as aforementioned to monitor ADP generation from purified PfPK9 and UBC13 proteins, UBC13 phosphorylation by PfPK9 was significantly decreased by both inhibitors as compared to DMSO, vehicle control.

Taken together, these results indicate that the tested PfPK9 inhibitors (i.e. compounds 1 and 5) decrease UBC13-mediated K63 protein ubiquitination in *Plasmodium* parasites through a mechanism impairing PfPK9 functions.

Example 11. Kinase Screening

Kinase Selectivity Profiling.

Figure 6:
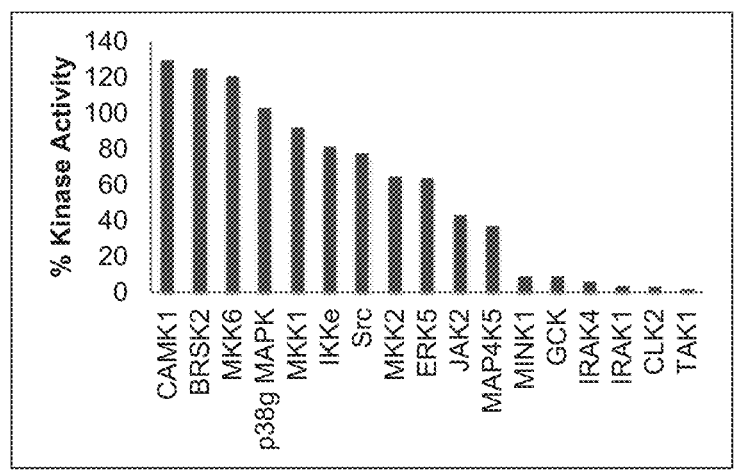
FIG. 6 shows the structure of HS-206 and results of kinase inhibition assay performed at MRC Dundee (shown are representatives of the 140 kinases assayed).

The selectivity profile of HS-206 to inhibit mammalian kinases was tested against a panel of 140 kinases at a single concentration of 10 µM. Tests were performed using a radiolabeld ($^{33}$P-ATP) filter-binding assay at the International Centre for Kinase Profiling at the University of Dundee, UK (http://www.kinase-screen.mrc.ac.uk/). See FIG. 6.

This panel contains members of all major kinase families, including tyrosine kinases (TK), tyrosine kinase-like (TKL), sterile serine/threonine (STE), and CDK/MAPK/GSK/CLK (CMGC). The strongest kinase inhibition was found for TAK1 (STE/TKL family), IRAK4 (TKL), IRAK1 (TKL), CLK2 (CMGC), GCK (STE), and MINK1 (STE), indicating that members of several kinase families were targeted. For these kinases, IC50 values were determined (Table 1).

TABLE 1

| Kinase | IC50 (µM) |
| --- | --- |
| TAK1 | 0.0095 ± 0.002 |
| CLK2 | 0.43 ± 0.04 |
| IRAK1 | 0.39 ± 0.05 |
| IRAK4 | 0.12 ± 0.03 |
| GCK | 0.43 ± 0.04 |
| MINK1 | 1.9 ± 1 |

Figures 7, 8:
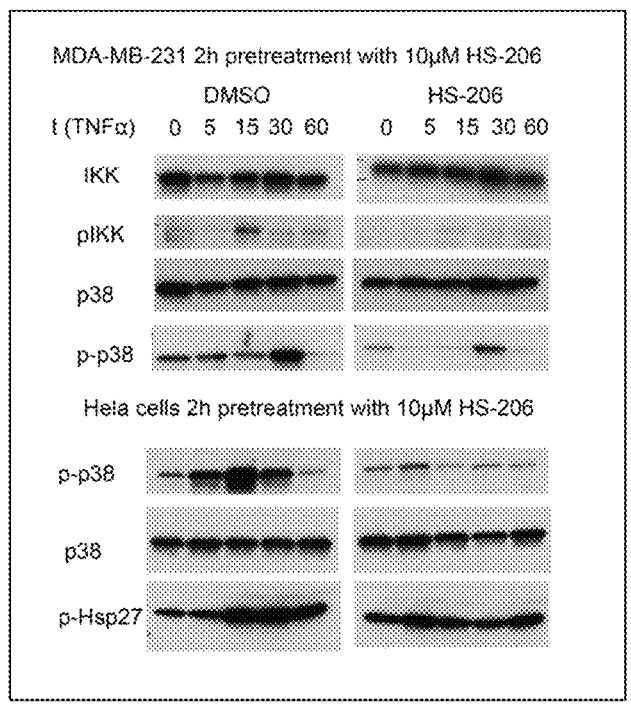
FIG. 7 shows the sequence alignment from the activation loop of IRAK4, TAK1, PfPK9, and IRAK1. Shown is the alignment of the activation loop (TAK1: residues 178-190). Dark grey indicates high conservation, red box highlights activation loop.
FIG. 8 shows that HS-206 inhibits TNFα dependent signaling in MDA-MB-231 and Hela cells.

Compound 1 significantly decreased (≥80% inhibition) the activity of only 11 of the 140 kinases when tested at 10 M. Of the top kinase hits identified, the activity of six kinases (MINK1, GCK, IRAK4, IRAK1, CLK2, TAK1) was inhibited by greater than 90%. Remarkably, TAK1, IRAK4, and IRAK1 are part of the ubiquitin signaling pathway in mammalian cells, which demonstrates functional similarities in the identified kinase hits. However, these kinases show no significant sequence similarities, which is demonstrated in the sequences of the activation loop of these kinases (FIG. 7). It is believed that HS-206 inhibits TAK1 in the nM range.

Kinase Assay.

Activity of purified TAK1-TAB1 protein was measured as previously described (Hastie et al., Nat. Protoc. (2006) 1, 968-971). In brief, TAK1-TAB1 (50 ng/well) was incubated with 5 µM ATP containing radiolabeled [$^{32}$P]-ATP in the presence of 300 µM substrate peptide (RL-GRDKYKTLRQIRQ) in a final volume of 40 µl in the presence of buffer (containing 50 mM Tris pH 7.5, 0.1 mM EGTA, 0.1% β-Mercaptoethanol, 10 mM magnesium acetate, 0.5 mM MnCl) and indicated compounds. The reaction was let go for 10 min and stopped with 10 µl concentrated H$_3$PO$_4$. The remaining activity was measured using a scintillation counter. Dose-response curves were repeated 3 times. For kinetic mechanistic studies, experiments were repeated two times and averaged.

Figures 12A, 12B:
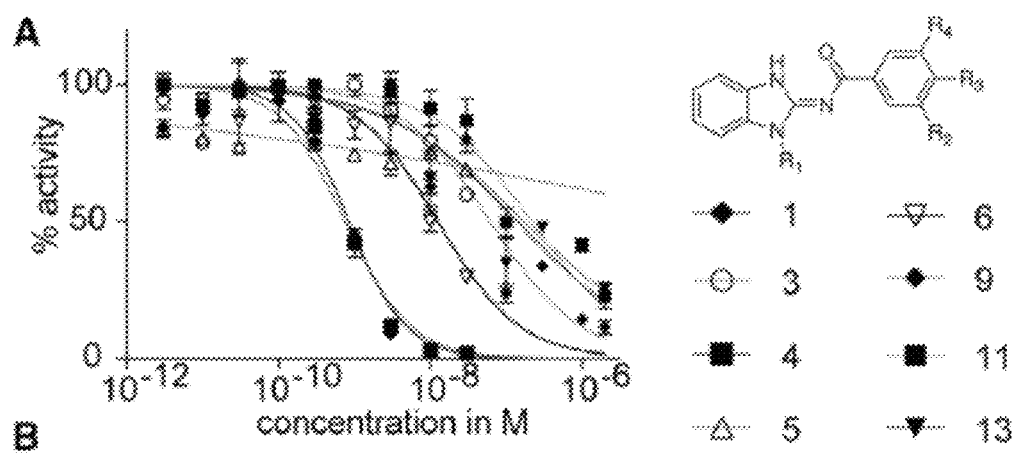
FIG. 12A shows dose-response curves for TAK1 inhibition.
FIG. 12B shows TAK1 $IC_{50}$ values.

Further TAK1 activity is illustrated for compounds in FIGS. 12A-12B.

Example 12. Effects of HS-206 on Cellular Signaling

Figure 9:
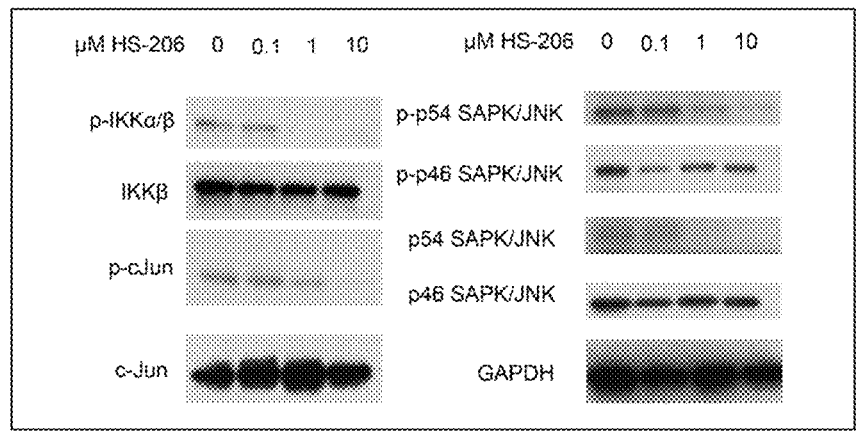
FIG. 9 shows dose-dependent inhibition of JNK and NFκB signaling by HS-206 in Hela cells.

In order to investigate the effects of HS-206 on cellular signaling, MDA-MB-231 and Hela cells were pretreated with 10 µM HS-206 for 2 h and stimulated with TNFα (FIG. 8). In this study, HS-206 inhibited activation of IKK and p38, demonstrating the inhibition of TAK1 downstream signaling. Additionally, HS-206 was found to inhibits p38 and NFκB signaling in a dose-dependent manner in Hela cells upon TNFα stimulation (FIG. 9).

Example 13. Selectivity of HS-206

The selectivity of compound 1 was also evaluated using ATP-beads to identify potential off-target binding proteins in mammalian cells. This method has been successfully used to assess the specificity of small molecule inhibitors of purine binding proteins. Whole-cell lysates from uninfected HepG2 cells were added to ATP-bound sepharose beads and eluted with increasing concentrations of compound 1. DMSO was used as the negative control and the positive control was the heat-shock protein 90 (Hsp90) inhibitor geldanamycin. Addition of compound 1 up to 1 mM did not lead to any significant elution of ATP-binding proteins when compared to the DMSO control. In contrast, addition of geldanamycin to the cell extract on ATP-beads resulted in a dose-dependent elution of a band at 90 kDa corresponding to Hsp90, as confirmed by matrix-assisted laser desorption ionization (MALDI). Based on band intensity quantification of Hsp90 as a function of geldanamycin concentrations, a K$_{d(app)}$ value of 5.5 nM (95% Cl: 4.5-6.8 nM) was calculated.

Example 14. Effects of HS-206 on Cell Viability

Figure 11:
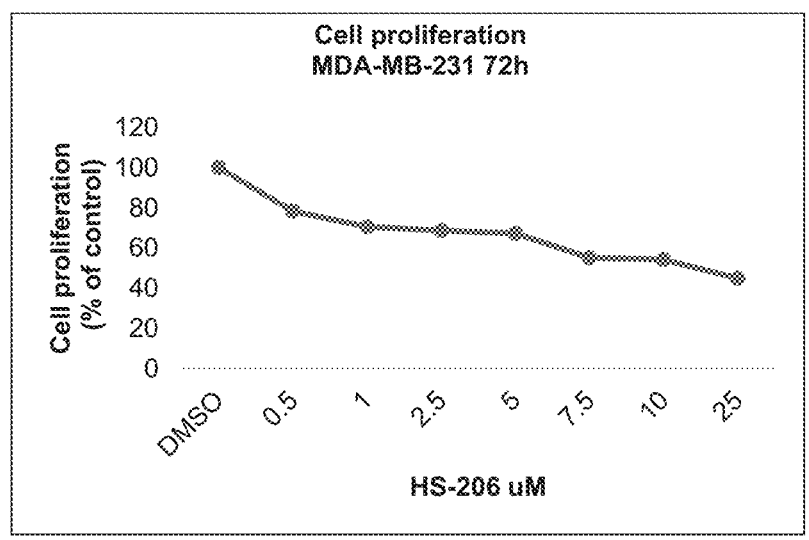
FIG. 11 shows that HS-206 inhibits cell proliferation in a dose-dependent manner.

In order to examine the effect of HS-206 on cell viability of different cancers, a screen of 60 cell lines was performed at the NCI, called the NCI-60 Cell One-Dose Screen. Cancer types most affected by a single dose of 10 µM HS-206 included colorectal (KM12), leukemia (HL-60), and non-small cell lung cancer (NCI-H522), whereas cancers like melanoma (M14), renal (786-0), and ovarian cancer (Ovcar-3) showed little effect (FIG. 10). This screen determined growth inhibition as an effect of HS-206 treatment over a period of 24 h. Viability and proliferation assays on multiple breast cancer cell lines were performed over 48 h and 72 h and found a significant reduction in cell proliferation in the cell line MDA-MB-231 (FIG. 11).

Example 15. Functionalizing Takinib

Figure 14:
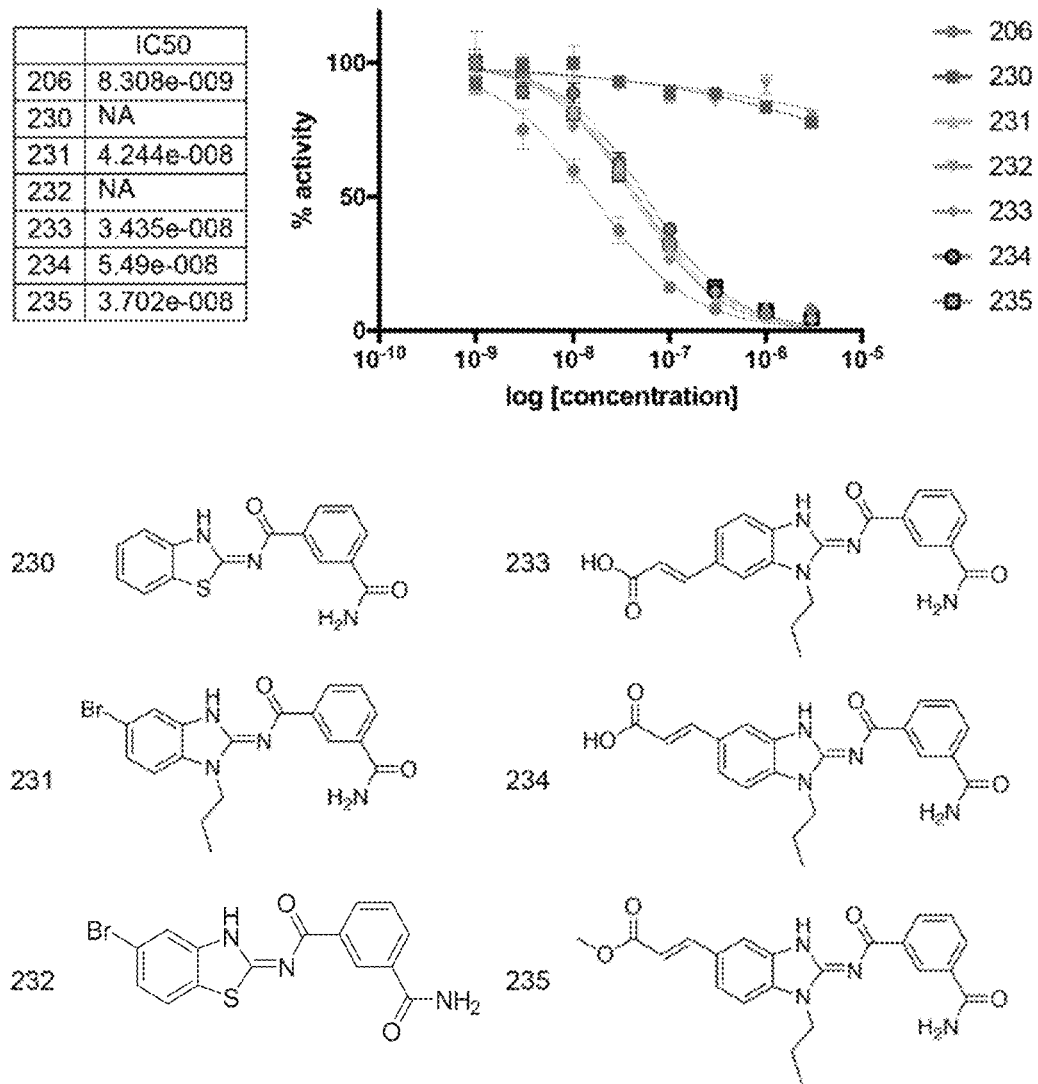
FIG. 14 shows the identification of modifiable residues on Takinib (also 206).

A challenge in designing chemical biology probes lies in choosing an appropriate ligand for a protein target and developing chemistry that allows attachment of a linker without disrupting activity of the ligand. The crystal structure shows solvent-exposed residues on Takinib (FIG. 13). Chemical modifications of these residues are likely to be tolerated with a limited loss in potency. The focus was on modifying the aminobenzimidazole moiety. The analogs 230 to 235 were synthesized and tested in a kinase assay as previously described (FIG. 14). Aminobenzothiazoles 230 and 232 did not show activity. Modifications on the solvent-exposed regions of Takinib was tolerated and only showed a slight reduction in potency (compare 206 to 231, 233, 234, 235). Both the 4 and 5 positions can be modified in future applications (compare 233 and 234).

Example 16. Affinity Resin Chromatography

Affinity chromatography is a method to separate target molecules from a mixture based on selective interactions of the target in the soluble phase with a stationary phase. The basic principle of adding a mixture to a solid phase followed by washing and elution provides the basis for high purity protein purification necessary for many functional enzyme assays including the kinase assay. Various affinity media (i.e. Avidin-Biotin, Glutathione-GST) have been developed to enable protein purification based on protein tag recognition and allow for purification of recombinant proteins. While commercially available affinity media allow researchers to purify recombinant proteins in a fast and reproducible manner, they utilize expensive ligands and often are limited due to nonspecific adsorption and leakage of ligand. Additionally, the use of a tag can change the biological function of a protein. One way to alleviate the disadvantages of commercially available affinity media could be to utilize small molecules as a ligand for the target protein to enable selective purification of native proteins. Elution of the target protein can be performed by free ligand competition or cleavage of the linker.

Despite the advantages of affinity chromatography for purification of native proteins, few strategies for selective kinase purification have been published. These approaches focus on creatinine kinase, casein kinase, and GSK-3 and demonstrated the necessity for highly potent affinity ligands. Utilizing substrate peptides proved inefficient due to a general low binding affinity to kinases. The Km of these substrates is in the low mM concentrations range, rendering them inadequate as ligands for affinity chromatography. High affinity small molecule inhibitors could circumvent this issue.

Previous efforts to develop kinase inhibitor beads provide datasets for potential affinity chromatography ligands. Identifying off-target effects of small molecule kinase inhibitors provide a dataset of potential ligands for affinity chromatography. Individual small molecule kinase inhibitors like Purvalanol B, Sunitinib, and Gefitinib were attached to beads and tested for their ability to bind to proteins. While many of the tested compounds bound a number of protein kinases (i.e. Purvalanol B, PD 173955), some inhibitors showed selective binding of only a few kinases (i.e. Imatinib, Lapatinib). These findings indicate that kinase affinity chromatography could be developed efficiently with commercially available ligands.

Example 17. Resin Ligands

Figure 15:
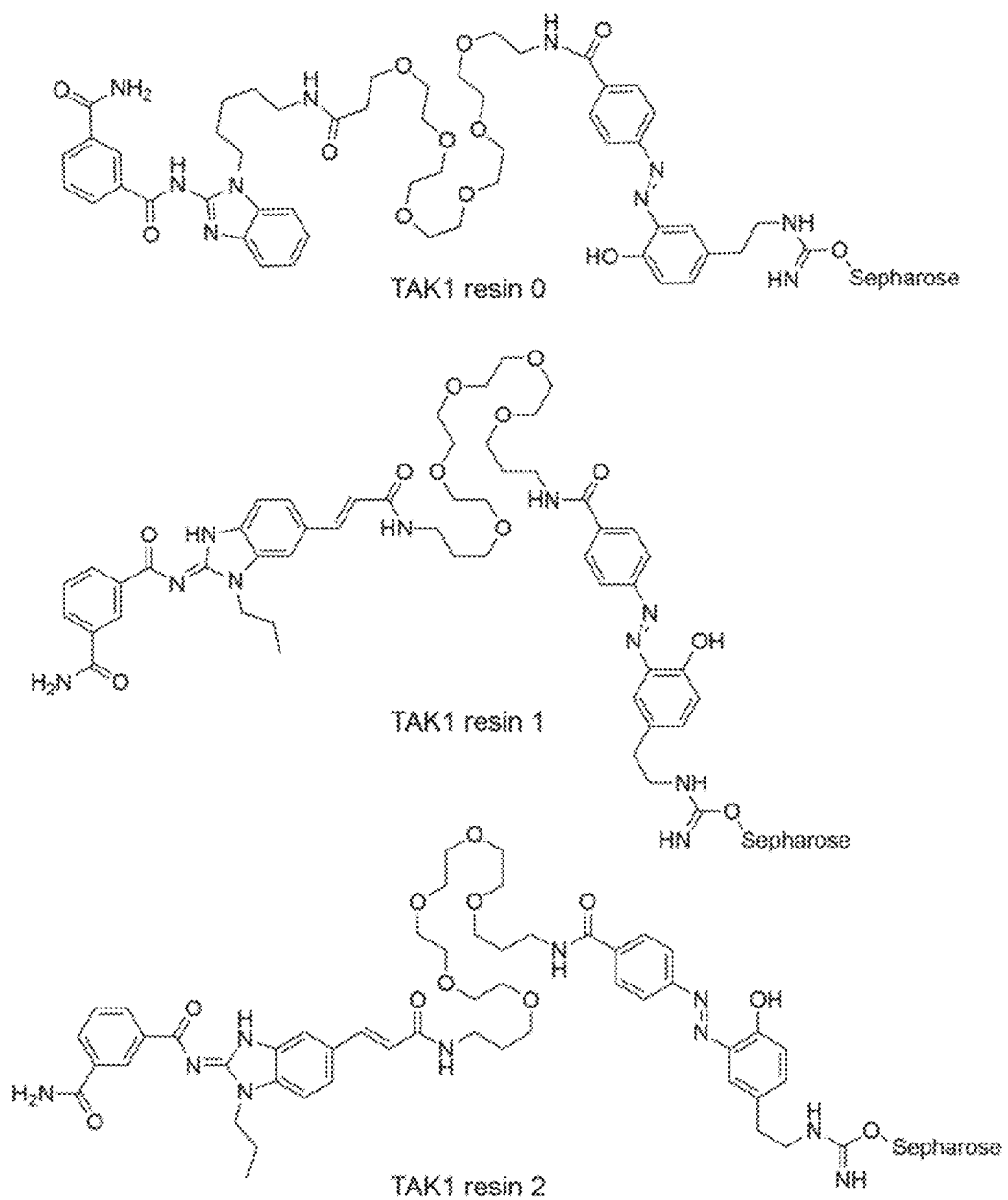
FIG. 15 shows TAK1 resin structures.

Ligands for TAK1 affinity chromatography were chosen as a result of previous SAR studies. Based on the activities of ligands 230-235 in the kinase assay, Takinib was modified at the respective positions analogous to 233 and 234 (FIG. 15). In order to allow linker cleavage under mild non-denaturing conditions, an azo cleavable linker was introduced. The azo linkage can be cleaved using a 25 mM sodium thiosulfate solution. TAK1 resin 0, 1, and 2 were synthesized and vary based on linker attachment sites.

Example 18. TAK1 Purification

Figure 17:
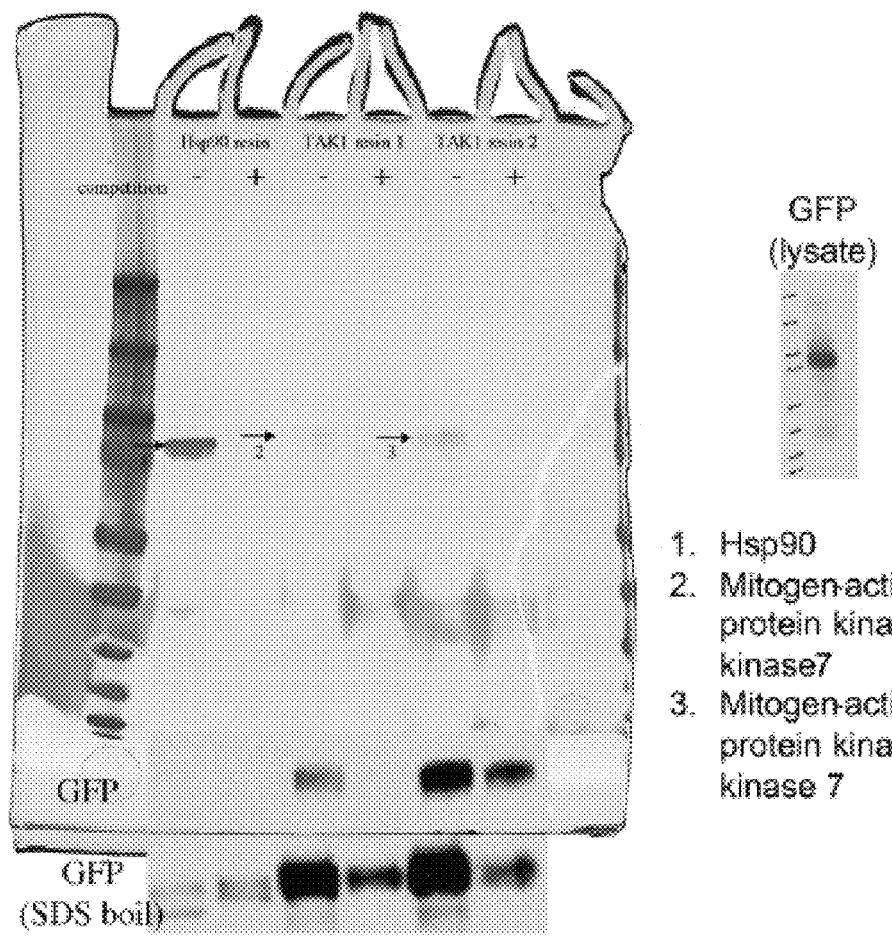
FIG. 17 shows affinity chromatography results with TAK1 resin 1 and 2.

The synthesized resins were tested with pig mammary gland extracts and cell lysates. Initial studies with native lysate from pig mammary gland using TAK1 resin 0 are shown in FIG. 16. Previous SAR studies demonstrated that substitution of the propyl chain with a butyl amine lead to a significant potency decrease. In these initial experiments, pig mammary gland was ground up and split into two groups: DMSO and 10 M Takinib treated extracts. This setup allows for ligand-selective interactions, which should not be retained in the Takinib-treated sample. Following incubation of the extracts with TAK1 resin 0, elution with 25 mM sodium thiosulfate took place. In the DMSO sample, the maximum amount TAK1 should stick to the resin. The Takinib-treated sample should contain less TAK1 bound to the resin due to free ligand competition. Following elution, resin beads were boiled with SDS sample buffer to determine how much protein was retained by the beads following elution. Samples were run on an SDS PAGE, silver stained, and western blotted for TAK1. The silver stained samples did not show a detectable amount of TAK1. However, the Western Blot showed increased TAK1 bound to the resin for DMSO-treated lysate compared to competed lysate. Following synthesis of TAK1 resin 1 and 2, these resins were compared side by side (FIG. 17). Due to low endogenous expression levels of TAK1, we overexpressed TAK1-TAB1-GFP fusion protein for proof-of-concept studies. As for TAK1 resin 0, lysate competition with either DMSO or 10 M Takinib was performed to investigate resin specificity. After incubation of the lysate with the resin, sodium thiosulfate was used to cleave off resin-bound protein. We utilized a selective cleavable Hsp90 resin as a control for proper cleavage. For this resin, the Hsp90 inhibitor HS-10 was used for lysate competition. To determine the remaining amount of protein in the resin, the beads were boiled in SDS sample buffer. All samples were run on SDS PAGE, silver stained, and blotted for GFP. In direct comparison of TAK1 resin 1 and 2, we found that TAK1 resin 2 had a larger quantity of TAK1 bound, which was detectable by silver stain, Western Blot of elutions, and Western Blot of SDS boil. However, this difference in protein binding between TAK1 resin 1 and 2 could also be due to a difference in ligand loading during resin synthesis. The silver stained bands were analyzed by mass spec and confirmed the identity of Hsp90 and TAK1 as eluted proteins in the Hsp90 resin and TAK1 resins, respectively.

Example 19. IRAK Purification

Figure 18:
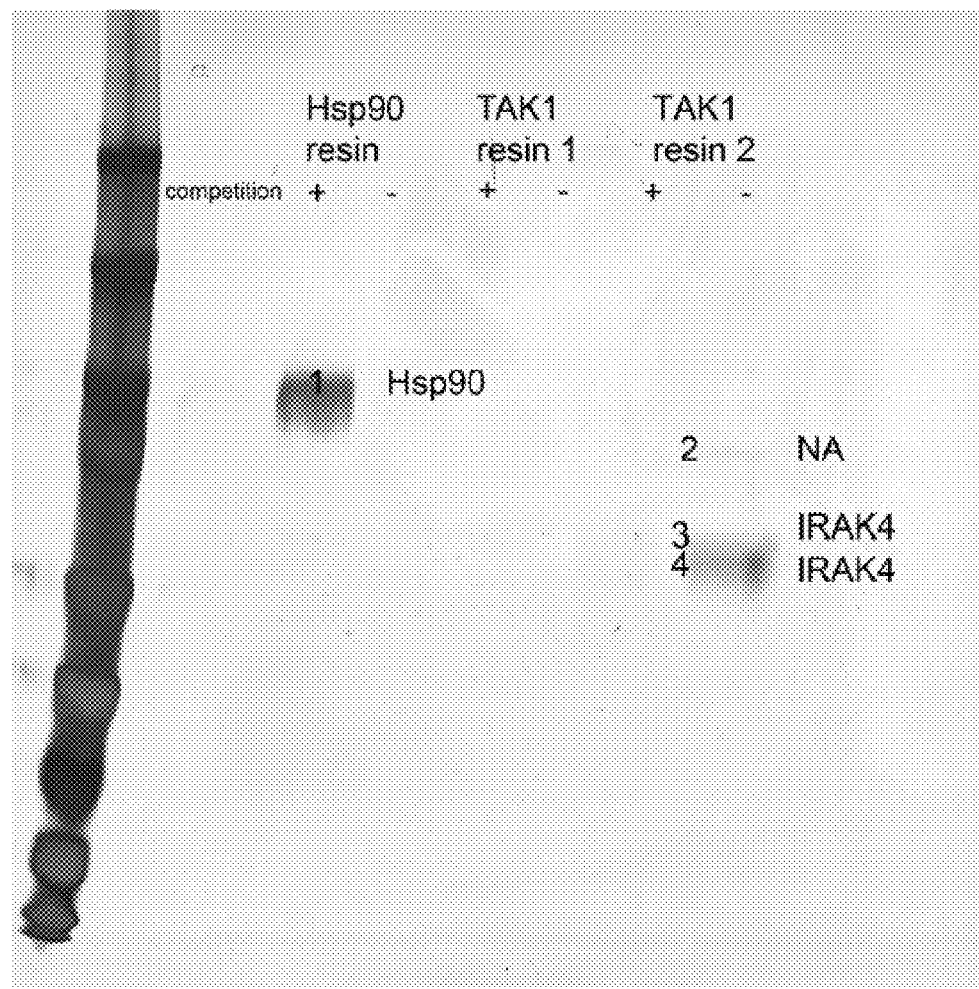
FIG. 18 shows IRAK4 purification silver stain.
Figure 19:
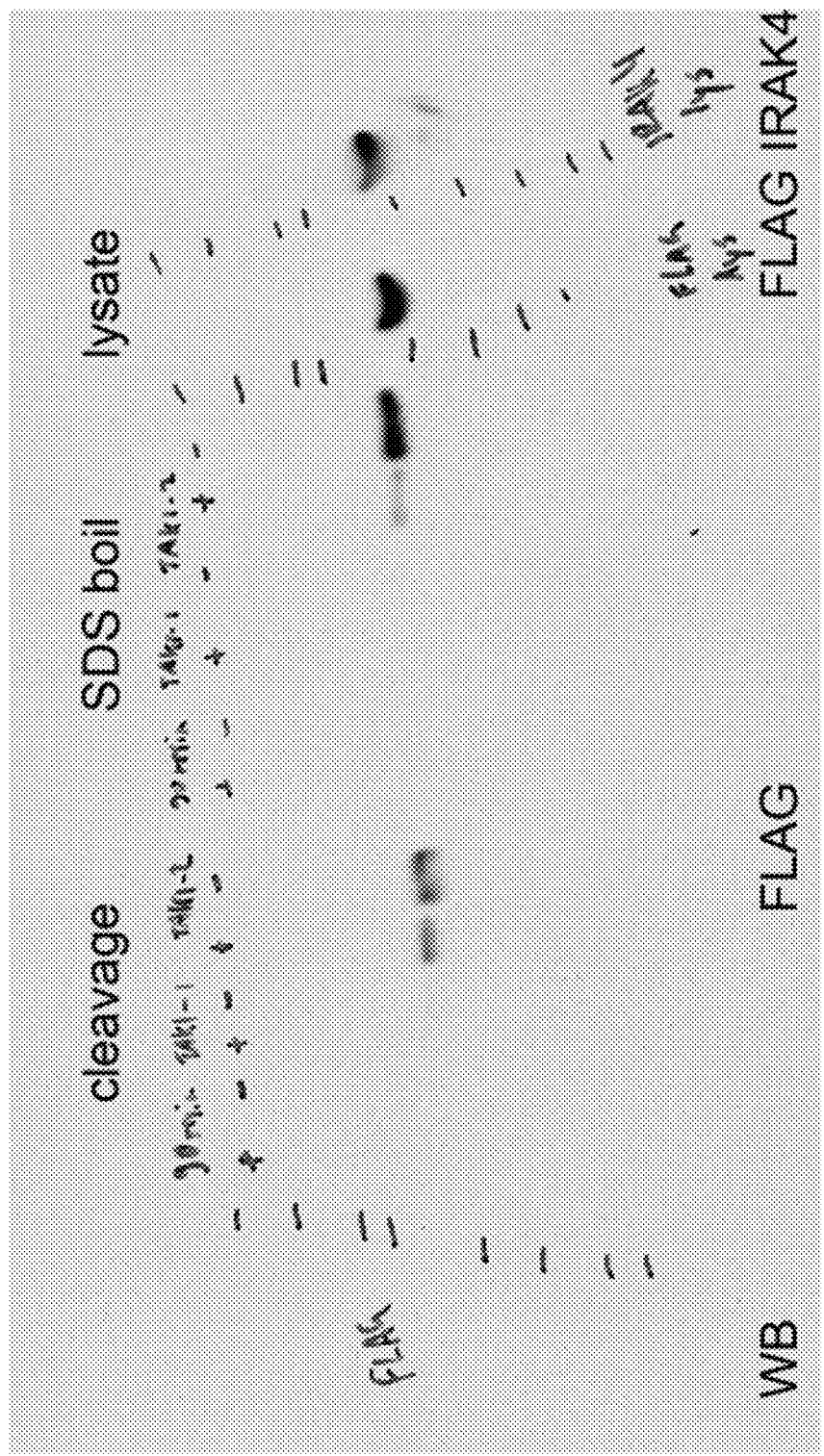
FIG. 19 shows IRAK4 protein expression.

Because Takinib showed moderated potency for IRAK4 in the initial selectivity screen, we tested whether TAK1 resin 1 or 2 could be used to purify IRAK4. In similar fashion as in the TAK1 purification experiment, FLAG-IRAK4 was expressed in HEK293T cells and competition experiments were performed with Takinib. The Hsp90 resin and HS-10 served as control as described above. All samples were run on an SDS PAGE, silver stained and western blotted for FLAG (FIG. 18). FLAG-IRAK4 protein expression in the cell lysate was confirmed by Western Blot (FIG. 19). The silver stained gels showed bands for the Hsp90 resin and TAK1 resin 2, while no bands were observed for TAK1 resin 1. Western Blot analysis confirmed this result. This study suggests differential affinity of IRAK4 to the structural modifications of Takinib that do not affect binding of Takinib to TAK1.

Example 20. Analysis of Proteolysis Targeting Chimera

Proteolysis targeting chimera (PROTAC) are bifunctional molecules that allow for targeted protein degradation through recruitment of a E3 ubiquitin ligase to a target protein. This interaction results in K48-linked polyubiquitination of the target protein and subsequent proteolysis of the target protein by the proteasome. PROTACs consist of two small molecules connected by a linker moiety: one targeting the E3 ubiquitin ligase and the other one targeting the protein of interest. Seminal studies identified several small molecule inhibitors targeting a variety of E3 ligases. For example, the E3 ligase Cereblon can be targeted by thalidomide, lenalidomide, and pomalidomide.

Targeted protein degradation combines advantages of small molecules and knockdown genetic approaches. For example, due to the rapid kinetics of polyubiquitination of the target protein upon PROTAC binding, protein degraders can be efficacious even in the presence of high affinity ligands like ATP or natural hormone ligands. Since PROTAC-protein complexes only need to exist transiently, small molecules with fast off-rates can be utilized. Therefore, previously discarded and low efficacy small molecule inhibitors could be repurposed into PROTACS. Further, PROTACS can act catalytically in their mode of action if the small molecule inhibitor is reversible. This allows for sub-stoichiometric drug administration, which means a lower therapeutic index and less off-target toxicities. Another issue of small molecule inhibitors that could be circumvented by targeted protein degradation is the fact that small molecules sometimes lead to target stabilization due to protein-inhibitor interaction. PROTAC could resolve the resulting target accumulation and reduce half-life. Hsp90 and TAK1 PROTAC molecules were developed based on the previously described Hsp90 inhibitor HS-10 and Takinib (FIG. 20).

Figure 21:
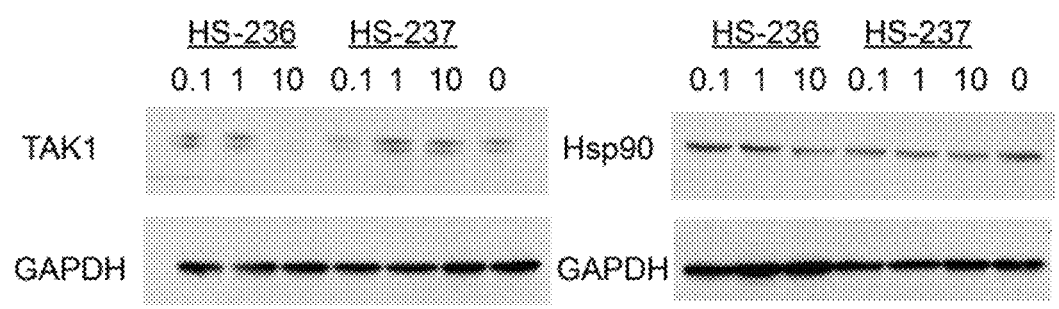
FIG. 21 shows Western Blot analysis of PROTAC-treated MDA-MB-231 cells.

HS-236 treatment showed a reduction in Hsp90 and TAK1 levels after 24 h treatment (FIG. 21). TAK1 is an Hsp90 client protein, which is why its expression is likely affected in these samples. The TAK1 PROTAC HS-237 showed a reduction in protein levels at 0.1M, but no effect on the higher concentrations. This effect has previously been described as prozone effect. At high PROTAC concentrations, both E3 ligase and protein are saturated individually with PROTAC, so that the complex of ligase and protein can no longer be formed.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

The invention claimed is:

1. A compound according to Formula (II):

(II)

or a pharmaceutically acceptable salt or tautomer thereof, wherein:

X is $NR_1$;

$R_1$ is $C_{1-6}$ alkyl or $-L_1-G_1$, wherein the $C_{1-6}$ alkyl is optionally substituted by halogen, $NH_2$, $NH(C_{1-4}$ alkyl), $N(C_{1-4}$ alkyl$)_2$, or OH;

$R_2$ is H, halogen, or $-L_2-R_6$;

$R_3$ is $C(O)R_5$;

$R_4$ is H, halogen, $C_{1-4}$ alkyl, or $OC_{1-4}$ alkyl, wherein the $C_{1-4}$ alkyl is optionally substituted by halogen, $NH_2$, $NH(C_{1-4}$ alkyl), $N(C_{1-4}$ alkyl$)_2$, or OH;

$R_5$ is $NH_2$, $NH(C_{1-4}$ alkyl), $N(C_{1-4}$ alkyl$)_2$, OH, or $OC_{1-4}$ alkyl;

$R_6$ is $C(O)NH_2$, $C(O)NHC_{1-4}$ alkyl, $C(O)N(C_{1-4}$ alkyl$)_2$, $C(O)NH-C_{2-6}$ alkylene-$NH_2$, $C(O)NH-C_{2-6}$ alkylene-$NH(C_{1-4}$ alkyl), $C(O)NH-C_{2-6}$ alkylene-$N(C_{1-4}$ alkyl$)_2$, $C(O)N(C_{1-4}$ alkyl)-$C_{2-6}$ alkylene-$NH_2$, $C(O)N(C_{1-4}$ alkyl)-$C_{2-6}$ alkylene-$NH(C_{1-4}$ alkyl), $C(O)N(C_{1-4}$ alkyl)-$C_{2-6}$alkylene-$N(C_{1-4}$ alkyl$)_2$, $C(O)NH-L_3-G_2$, $C(O)NH-L_4-G_3$, $C(O)OH$, or $C(O)OC_{1-4}$ alkyl;

$G_1$ is H, $C(NH)O$-agarose resin, or $C(O)OC_{1-4}$ alkyl;
$G_2$ is H, $C(NH)O$-agarose resin, or $C(O)OC_{1-4}$ alkyl;
$G_3$ is H; or $G_3$ is:

or

;

$L_1$ is:

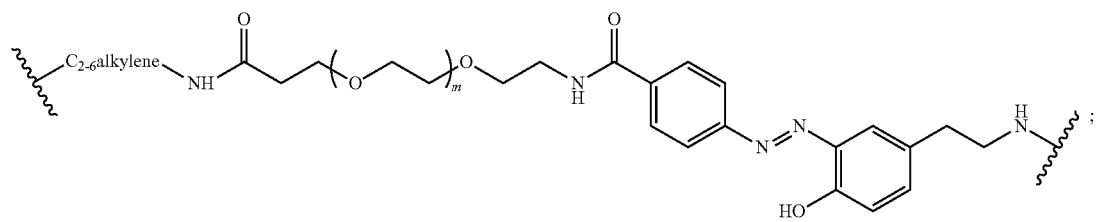

$L_2$ is —CH$_2$CH$_2$- or —CH=CH—;
$L_3$ is:

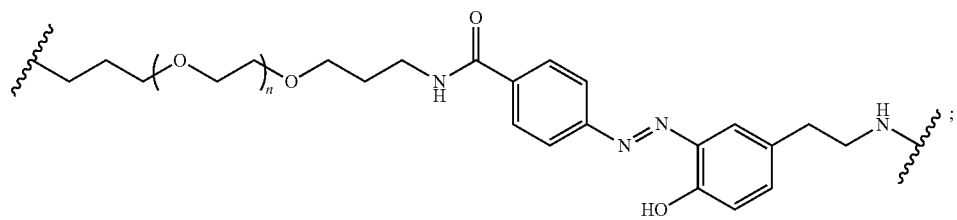

$L_4$ is:

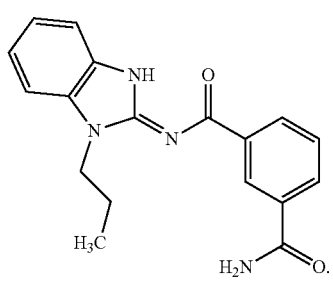

m is 1, 2, 3, 4, or 5; and
n is 1, 2, 3, 4, or 5;
with the proviso that the compound of Formula (II) is not:

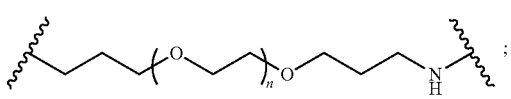

2. The compound of claim 1, or a pharmaceutically acceptable salt or tautomer thereof, wherein:
R$_1$ is C$_{1-6}$ alkyl, wherein the C$_{1-6}$ alkyl is optionally substituted by halogen, OH, NH$_2$, NH(C$_{1-4}$ alkyl), or N(C$_{1-4}$ alkyl)$_2$; and
R$_6$ is C(O)OH, C(O)OC$_{1-4}$ alkyl, C(O)NH$_2$, C(O)NHC$_{1-4}$ alkyl, C(O)N(C$_{1-4}$ alkyl)$_2$, C(O)NH-C$_{2-6}$ alkylene-N(C$_{1-4}$ alkyl)$_2$, C(O)NH-C$_{2-6}$ alkylene-NH(C$_{1-4}$ alkyl), C(O)NH-C$_{2-6}$ alkylene-NH$_2$, C(O)N(C$_{C1-4}$ alkyl)-C$_{2-6}$ alkylene-N(C$_{1-4}$ alkyl)$_2$, C(O)N(C$_{1-4}$ alkyl)-C$_{2-6}$ alkylene-NH(C$_{1-4}$ alkyl), C(O)N(C$_{1-4}$ alkyl)-C$_{2-6}$ alkylene-NH$_2$, C(O)NH-L$_3$-G$_2$, or C(O)NH-L$_4$-G$_3$; or
(ii) R$_1$ is -L$_1$-G$_1$; and
R$_6$ is C(O)OH, C(O)OC$_{1-4}$ alkyl, C(O)NH$_2$, C(O)NHC$_{1-4}$ alkyl, C(O)N(C$_{1-4}$ alkyl)$_2$, C(O)NH-C$_{2-6}$ alkylene-N(C$_{1-4}$ alkyl)$_2$, C(O)NH-C$_{2-6}$ alkylene-NH (C$_{1-4}$ alkyl), C(O)NH-C$_{2-6}$ alkylene-NH$_2$, C(O)N(C$_{1-4}$ alkyl)-C$_{2-6}$ alkylene-N(C$_{1-4}$ alkyl)$_2$, C(O)N (C$_{1-4}$ alkyl)-C$_{2-6}$ alkylene-NH(C$_{1-4}$ alkyl), or C(O)N (C$_{1-4}$ alkyl)-C$_{2-6}$ alkylene NH$_2$.

3. The compound of claim 2, wherein the compound is of Formula (II-A):

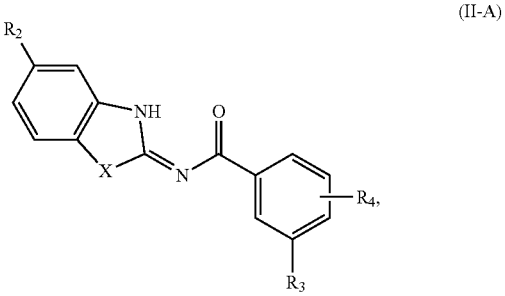

or a pharmaceutically acceptable salt or tautomer thereof.

4. The compound of claim 2, wherein the compound is of Formula (II-B):

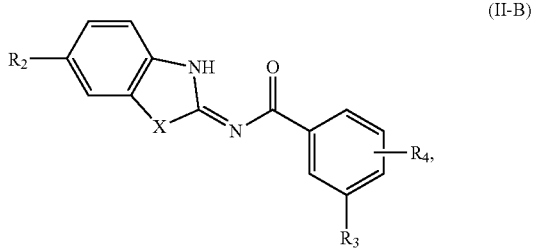

or a pharmaceutically acceptable salt or tautomer thereof.

5. The compound of claim 2, or a pharmaceutically acceptable salt or tautomer thereof, wherein:
R$_1$ is -L$_1$-G$_1$; and
R$_6$ is C(O)NH$_2$, C(O)NHC$_{1-4}$ alkyl, C(O)N(C$_{1-4}$ alkyl)$_2$, C(O)NH-C$_{2-6}$ alkylene-NH$_2$, C(O)NH-C$_{2-6}$ alkylene- NH($C_{1-4}$ alkyl), C(O)NH-$C_{2-6}$ alkylene-N($C_{1-4}$ alkyl)$_2$, C(O)N($C_{1-4}$ alkyl)-$C_{2-6}$ alkylene-NH$_2$, C(O)N($C_{1-4}$ alkyl)-$C_{2-6}$ alkylene-NH($C_{1-4}$ alkyl), C(O)N($C_{1-4}$ alkyl)-$C_{2-6}$ alkylene-N($C_{1-4}$ alkyl)$_2$, C(O)OH, or C(O)O$C_{1-4}$ alkyl.

6. The compound of claim 5, or a pharmaceutically acceptable salt or tautomer thereof, wherein $R_2$ is H.

7. The compound of claim 2, or a pharmaceutically acceptable salt or tautomer thereof, wherein $R_2$ is halogen.

8. The compound of claim 2, or a pharmaceutically acceptable salt or tautomer thereof, wherein:
$R_2$ is -$L_2$-$R_6$; and
$R_6$ is C(O)NH$_2$, C(O)NH$C_{1-4}$ alkyl, C(O)N($C_{1-4}$ alkyl)$_2$, C(O)NH-$C_{2-6}$ alkylene-NH$_2$, C(O)NH-$C_{2-6}$ alkylene-NH($C_{1-4}$ alkyl), C(O)NH-$C_{2-6}$ alkylene-N($C_{1-4}$ alkyl)$_2$, C(O)N($C_{1-4}$ alkyl)-$C_{2-6}$ alkylene-NH$_2$, C(O)N($C_{1-4}$ alkyl)-$C_{2-6}$ alkylene-NH($C_{1-4}$ alkyl), C(O)N($C_{1-4}$ alkyl)-$C_{2-6}$ alkylene-N($C_{1-4}$ alkyl)$_2$, C(O)OH, or C(O)O$C_{1-4}$ alkyl.

9. The compound of claim 8, or a pharmaceutically acceptable salt or tautomer thereof, wherein $R_1$ is $C_{1-6}$ alkyl.

10. The compound of claim 2, or a pharmaceutically acceptable salt or tautomer thereof, wherein:
$R_1$ is $C_{1-6}$ alkyl, wherein the $C_{1-6}$ alkyl is optionally substituted by halogen, NH$_2$, NH($C_{1-4}$ alkyl), N($C_{1-4}$ alkyl)$_2$, or OH;
$R_2$ is -$L_2$-$R_6$; and
$R_6$ is C(O)NH-$L_3$-$G_2$.

11. The compound of claim 2, or a pharmaceutically acceptable salt or tautomer thereof, wherein:
$R_1$ is $C_{1-6}$ alkyl, wherein the $C_{1-6}$ alkyl is optionally substituted by halogen, NH$_2$, NH($C_{1-4}$ alkyl), N($C_{1-4}$ alkyl)$_2$, or OH;
$R_2$ is -$L_2$-$R_6$; and
$R_6$ is C(O)NH -$L_4$-$G_3$.

12. The compound of claim 1, wherein the compound is selected from the group consisting of:

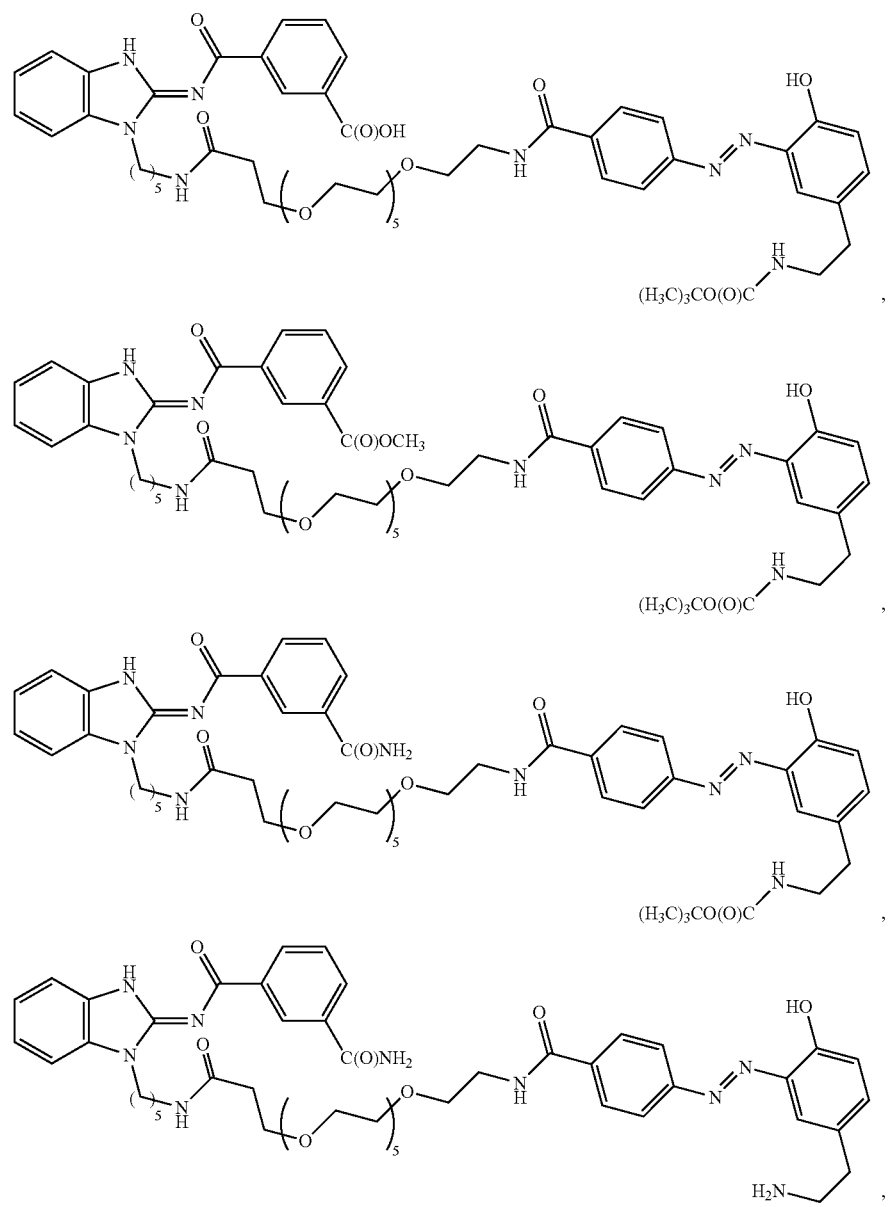

-continued
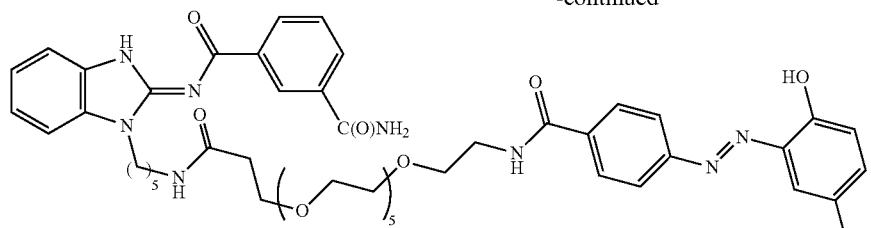
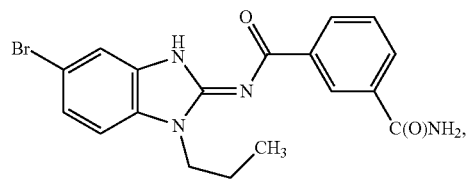
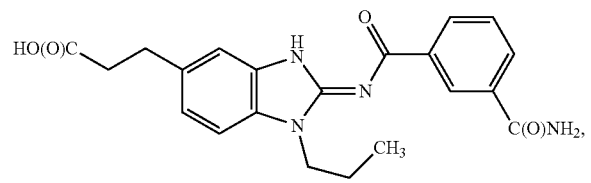
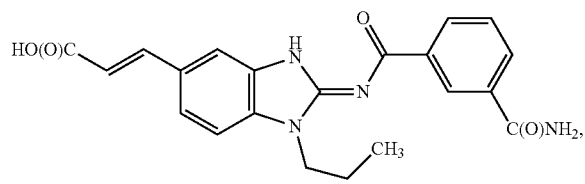
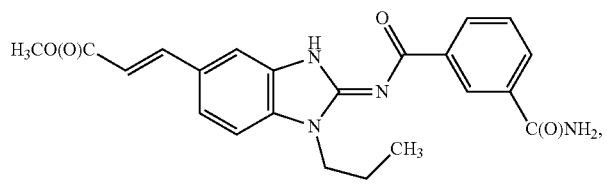
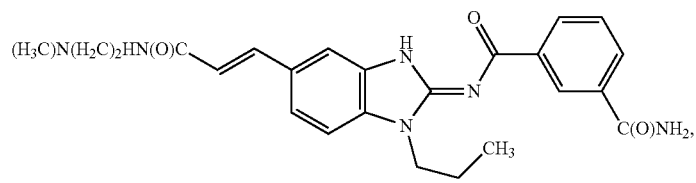
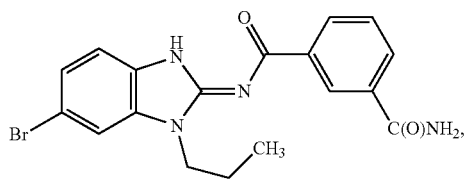
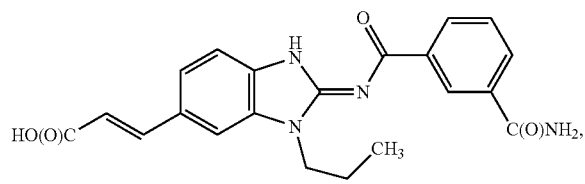
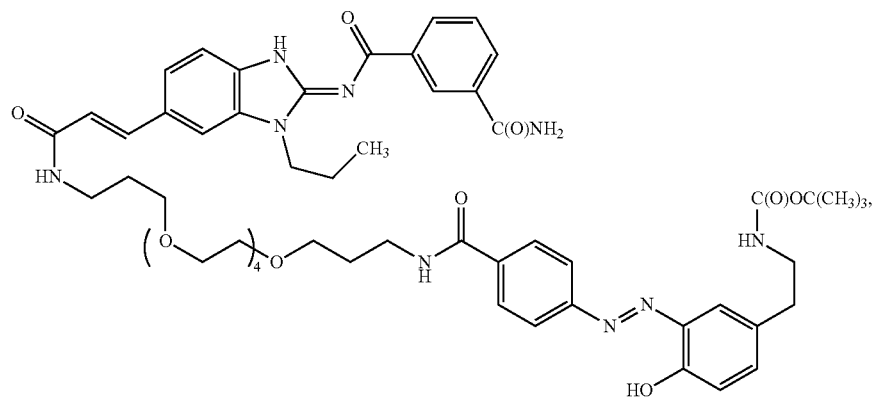

-continued
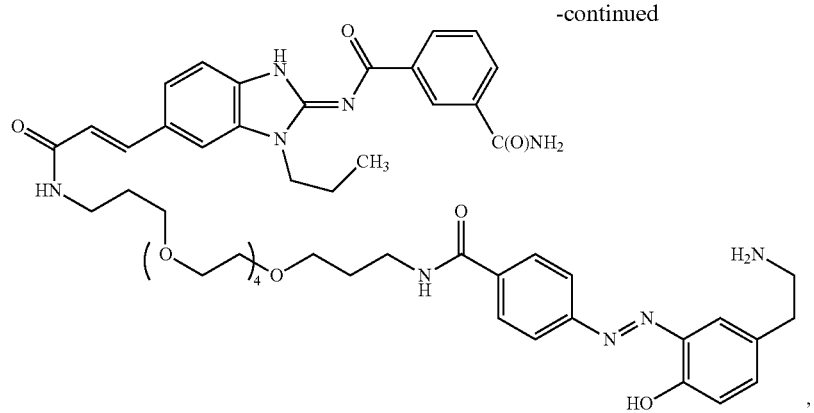
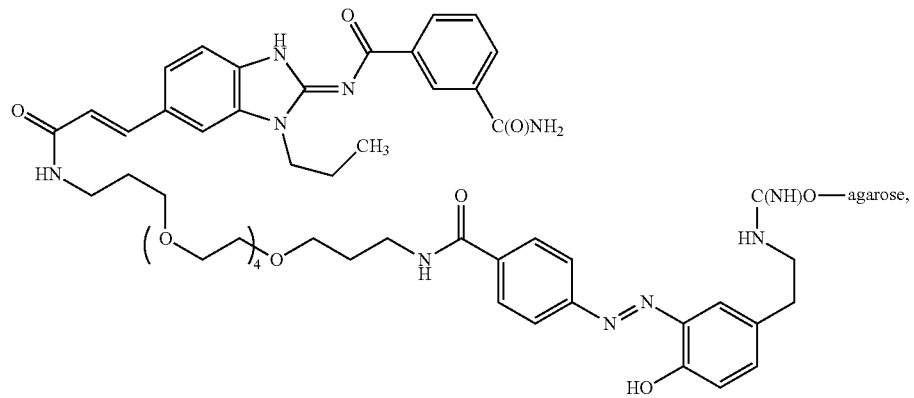
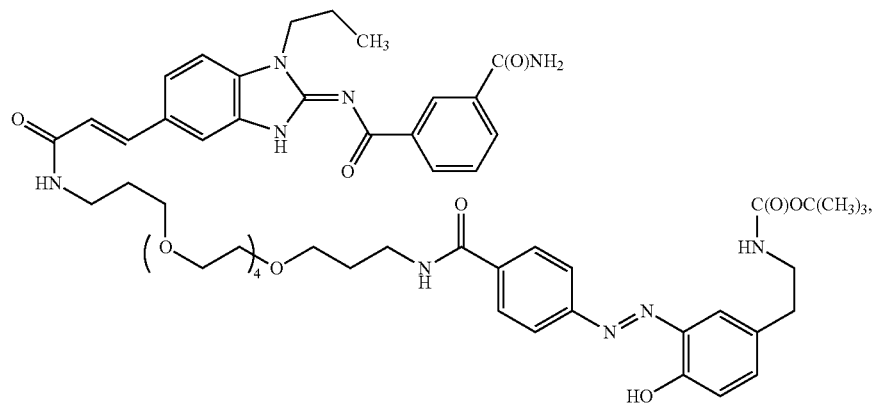
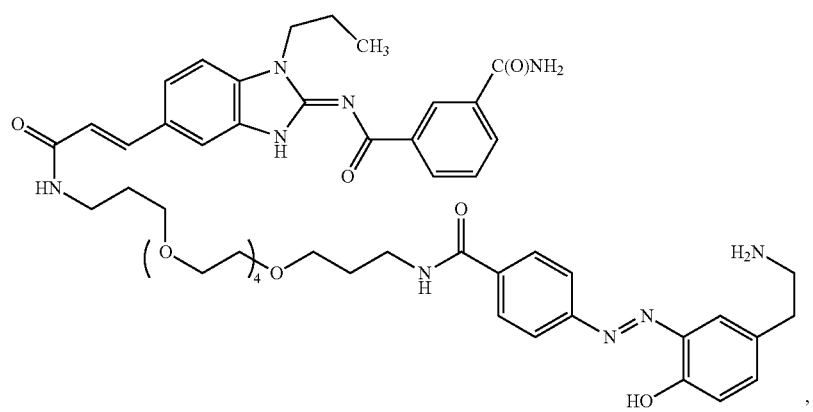

-continued
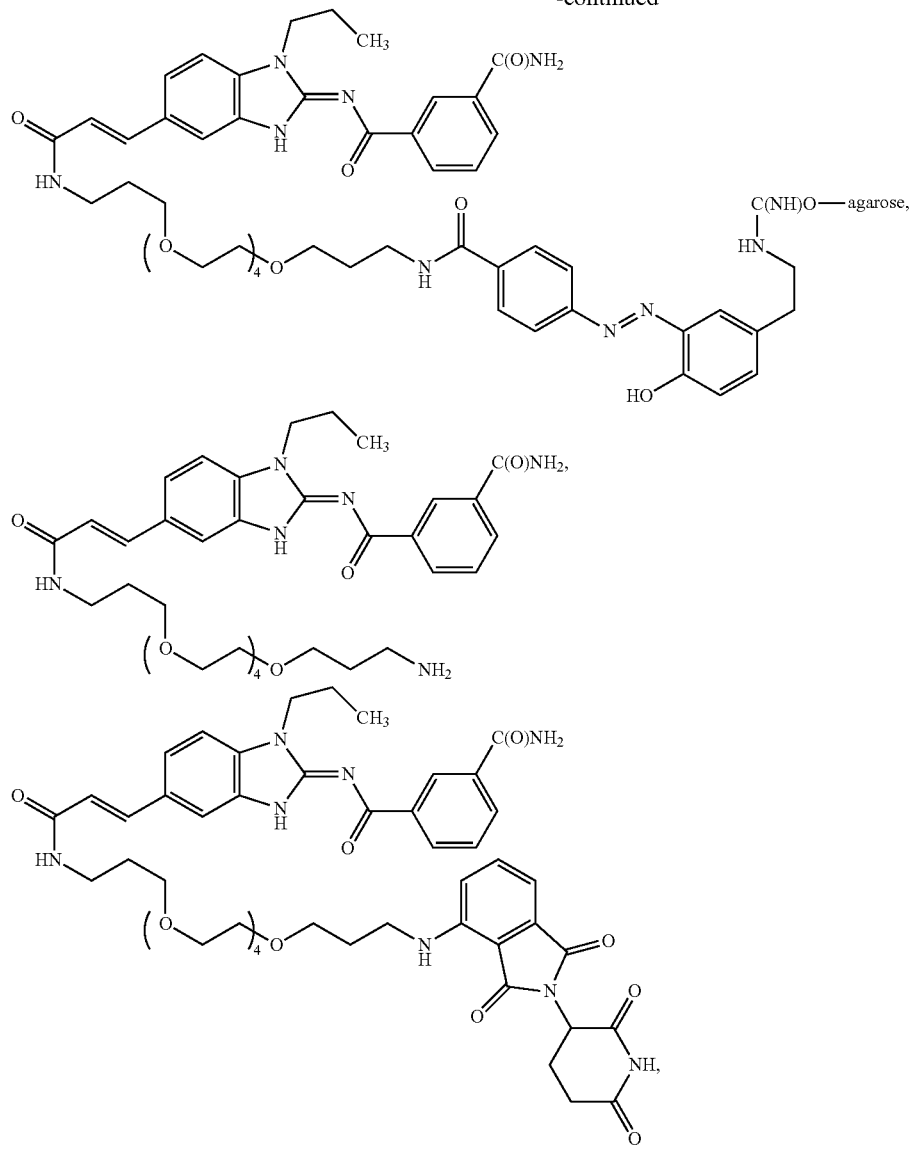
or a pharmaceutically acceptable salt or tautomer thereof.
13. A kit comprising the compound of claim 1, or a pharmaceutically acceptable salt or tautomer thereof, and instructions for treating a disease modulated by transforming growth factor β activated kinase 1 (TAK1).
* * * * *